US008637040B2

(12) United States Patent
Whittum-Hudson et al.

(10) Patent No.: US 8,637,040 B2
(45) Date of Patent: Jan. 28, 2014

(54) GENUS-WIDE CHLAMYDIAL PEPTIDE VACCINE ANTIGENS

(75) Inventors: Judith Whittum-Hudson, Novi, MI (US); Alan P. Hudson, Novi, MI (US)

(73) Assignee: National Institute of Health (NIH), U.S. Dept. of Health and Human Services (DHHS), Washington, DC (US)

( * ) Notice: Subject to any disclaimer, the term of this patent is extended or adjusted under 35 U.S.C. 154(b) by 0 days.

(21) Appl. No.: 13/120,071

(22) PCT Filed: Sep. 21, 2009

(86) PCT No.: PCT/US2009/057700
§ 371 (c)(1),
(2), (4) Date: Jun. 6, 2011

(87) PCT Pub. No.: WO2010/033923
PCT Pub. Date: Mar. 25, 2010

(65) Prior Publication Data
US 2011/0236484 A1      Sep. 29, 2011

Related U.S. Application Data

(60) Provisional application No. 61/098,769, filed on Sep. 21, 2008.

(51) Int. Cl.
*A61K 39/118*      (2006.01)
(52) U.S. Cl.
USPC ....... 424/185.1; 514/2.2; 514/21.6; 514/21.7; 530/327
(58) Field of Classification Search
None
See application file for complete search history.

(56) References Cited

U.S. PATENT DOCUMENTS

| | | | |
|---|---|---|---|
| 5,656,271 A | | 8/1997 | MacDonald et al. |
| 5,840,297 A | * | 11/1998 | MacDonald et al. ...... 424/131.1 |
| 5,882,645 A | * | 3/1999 | Toth et al. .................. 424/194.1 |
| 2002/0001597 A1 | | 1/2002 | Stuart et al. |
| 2007/0065387 A1 | * | 3/2007 | Beck et al. ................. 424/70.13 |

FOREIGN PATENT DOCUMENTS

| | | |
|---|---|---|
| WO | 9421291 A1 | 9/1994 |
| WO | 9524922 A1 | 9/1995 |
| WO | 03037172 A2 | 5/2003 |
| WO | 2005116234 A2 | 12/2005 |

OTHER PUBLICATIONS

Krause A. et al; "Complete genome of the mutualistic, N2 fixing grass endophyte *Azoarcus* sp. strain BH72." Nat. Biotech (2006) 24 (11) p. 1385-1391.*
NCBI reference sequence YP_935155.*
Meola A. et al; "Derivation of vaccines from mimotopes: Immunologic properties of human hepatitis b virus surface antigen mimotopes displayed on filamentous phage." J. Immun. (1995) 154(7) p. 3162-3172).*
Nurminen, M. et al; "Chemical characterization of Chlamydia trachomatis lipopolysaccharaide." Infection and immunity (1985) p. 573-575.*
Harmsen M. M. et al; "Properties, production, and applications of camelid single-domain antibody fragments." Appl. Microbiol. Biotechnol. (2007) 77 p. 13-22.*
Benmansour A. et al; "Antigenicity of rabies virus glycoprotein." J. Virol. (1991) p. 4198-4203.*
Nurminen, Marjatta et al; "Chemical characterization of chlamydia trachomatis lipopolysaccharade." Infection and immunity (1985) p. 573-575.*
Benmansour, A. et al; "Antigenicity of rabies virus glycoprotein." J. Virology (1991) 65(8) p. 4198-4230.*
Mitchell, D. J. et al; "Polyarginine enters cells more efficiently than other polycationic homopolymers." J. Peptide Res (2000) 56(5) p. 318-325.*
Meola, Annalisa et al; Derivation of vaccines from mimotopes. J. Immun. (1995) 154(7) p. 3162-3172.*
Clackson et al., "Making antibody fragments using phage display libraries," Nature, 352:624-628, Aug. 15, 1991.
Stuart et al., "Examination of chlamydial glycolipid with monoclonal antibodies: cellular distribution and epitope binding," Immunology 74:740-747, 1991.
Whittum-Hudson et al., "The anti-idiotypic antibody to chlamydial glycolipid exoantigen (GLXA) protects mice against genital infection with a human biovar of Chlamydia trachomatis," Vaccine 19:4061-4071, 2001.
Extended European Search Report and Opinion (relevant parts) (Mar. 6, 2012) (adding 3 references to those cited in the International Search Report).

* cited by examiner

*Primary Examiner* — Cecilia J Tsang
*Assistant Examiner* — Fred Reynolds
(74) *Attorney, Agent, or Firm* — Browdy and Neimark, PLLC

(57) ABSTRACT

Peptides generated from a random library that are bound by a monoclonal antibody to Chlamydial glycolipid exoantigen (GLXA) and thus mimic this antigen are disclosed. Peptides that correspond to antigen-binding regions of an anti-idiotypic antibody (mAb2) specific for anti-GLXA antibody (Ab1) which act as molecular mimics of GLXA are also disclosed used as immunogens to induce broadly reactive genus-specific anti-chlamydial antibodies. These peptides and immunogenic DNA encoding the mAb2-like peptides, microparticle or nanoparticle formulations and other formulations of these peptides are disclosed as are methods for immunizing subjects to obtain genus-specific anti-chlamydial antibodies and to treat or prevent *Chlamydia*-associated or induced rheumatoid arthritis.

26 Claims, 13 Drawing Sheets

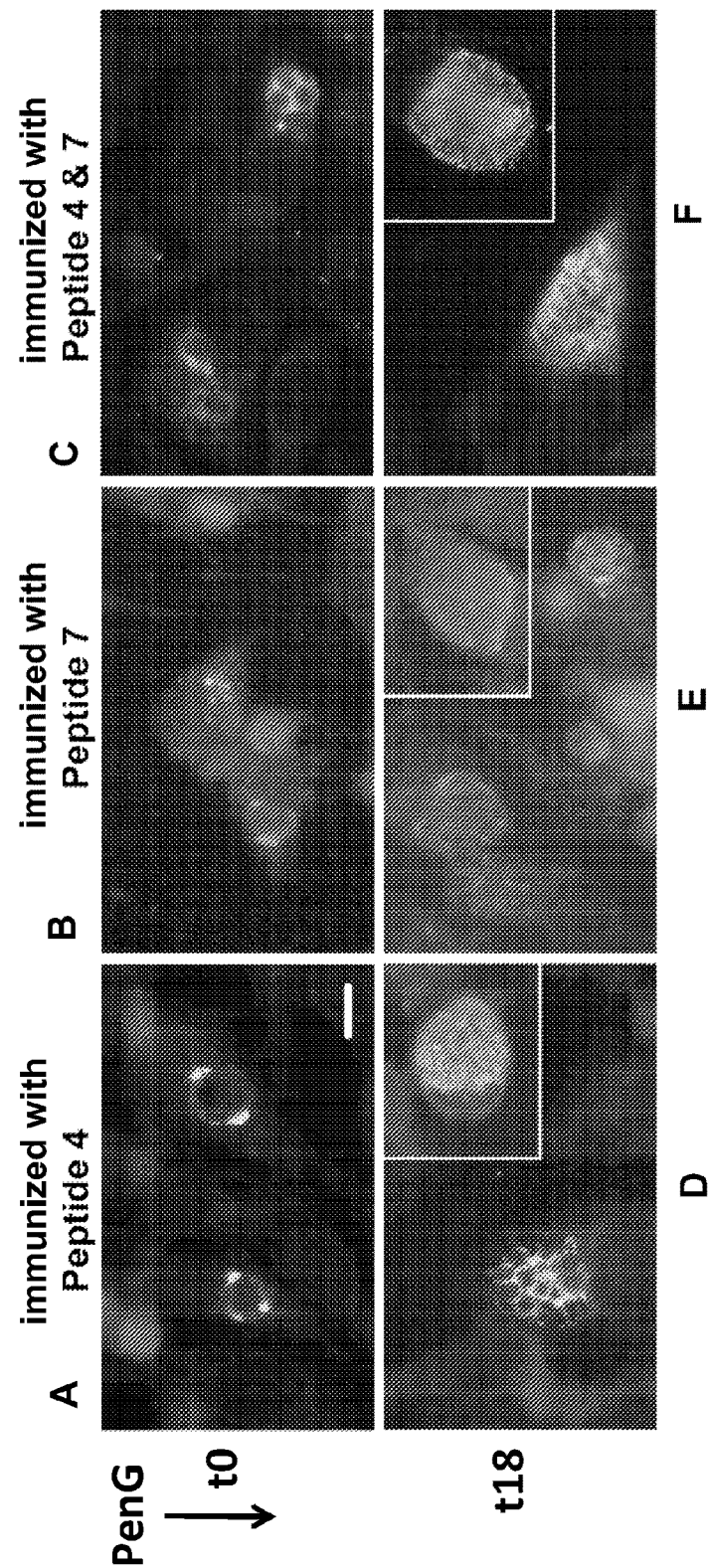

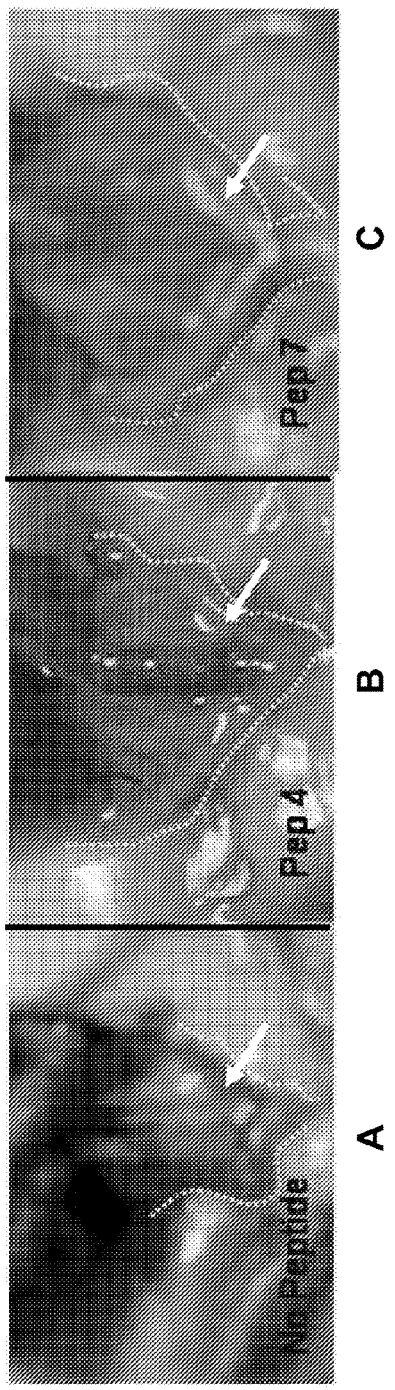
Fig. 15
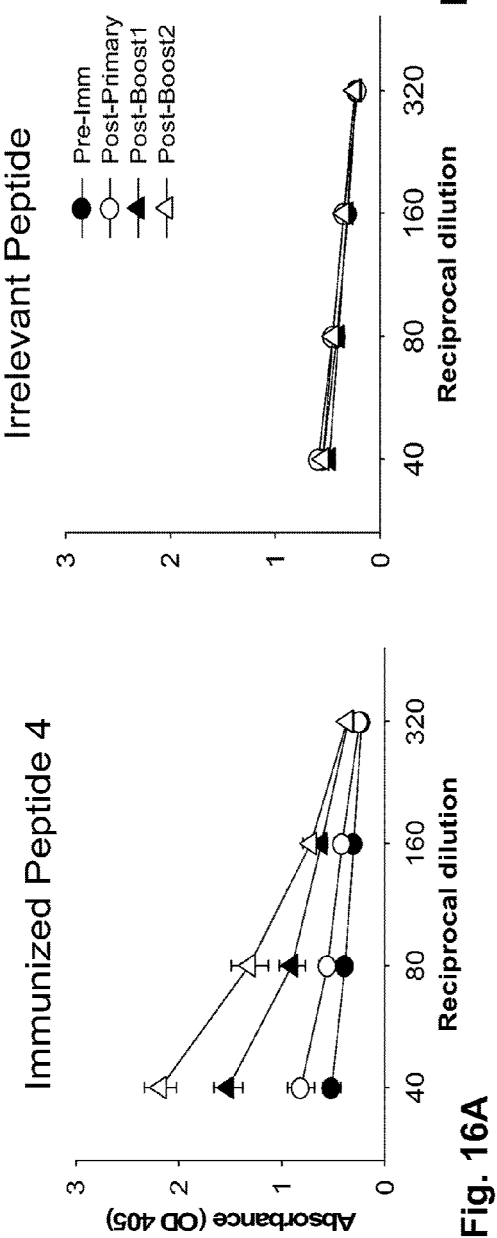
Fig. 16A
Fig. 16B

Fig. 18
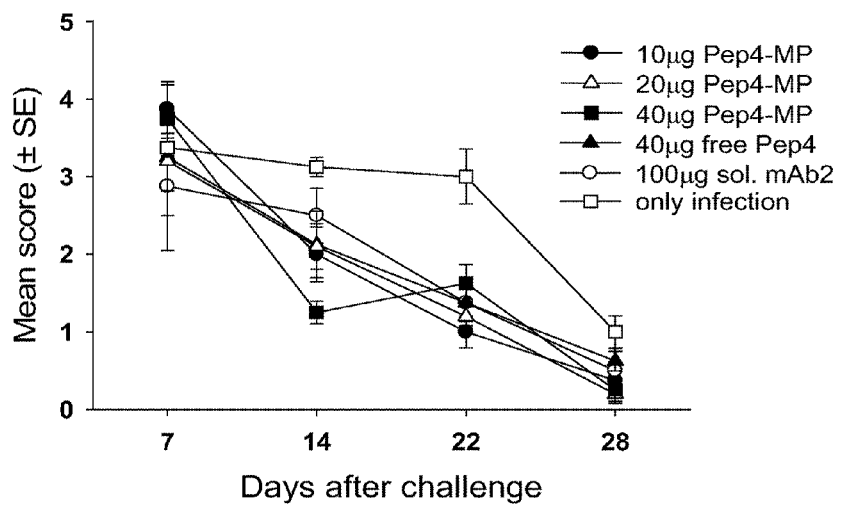
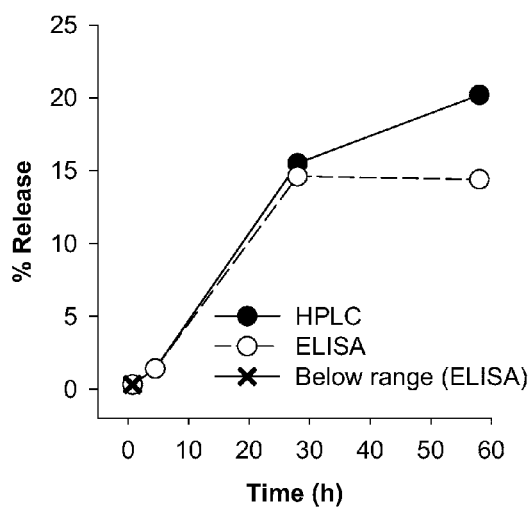
Fig. 19A
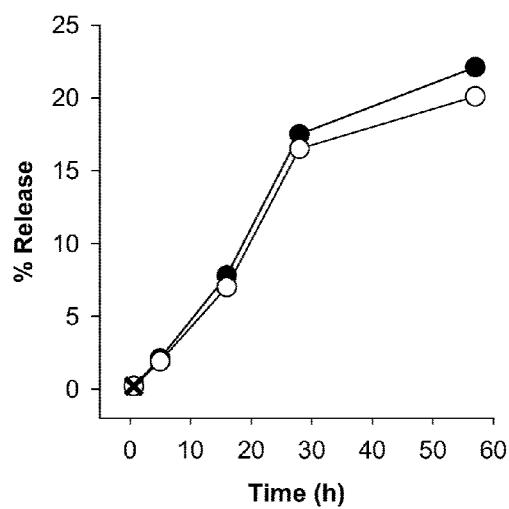
Fig. 19B

GENUS-WIDE CHLAMYDIAL PEPTIDE VACCINE ANTIGENS

STATEMENT OF RIGHTS TO INVENTIONS MADE UNDER FEDERALLY SPONSORED RESEARCH

This invention was funded in part by grants and contracts from the National Institute of Health, Department of Health and Human Services, which provides to the United States government certain rights in this invention.

BACKGROUND OF THE INVENTION

1. Field of the Invention

The invention in the field of immunology and infectious disease relates to novel peptide immunogens from a random library selected by an antibody against a Chlamydial glycolipid exoantigen (GLXA) or corresponding to antigen-binding regions of an anti-idiotypic antibody (mAb2) specific for an anti-GLXA antibody (Ab1) and which serves as a molecular mimic of GLXA, and their use in inducing antibodies against GLXA—a genus-wide ("genus-specific") chlamydial antigen.

2. Description of the Background Art

More than 1 million new cases of chlamydial infection were reported in 2006, and cost the economy over $1 billion dollars. Despite increased surveillance and treatment, chlamydial sexually transmitted disease (STD) infections continue to rise. *Chlamydia trachomatis* is the leading cause of tubal infertility and pelvic inflammatory disease (1,2). Asymptomatic and undiagnosed chlamydial infections are estimated to double the reported rate of infections. Chlamydial genital tract infection is more than 5 times more common than gonorrhea (3) and has been correlated with increased risk of infection with HIV and other STD pathogens (4). Chlamydial genital infection occurs in 5-15% of pregnant women, and 50% of their babies will develop inclusion conjunctivitis or respiratory infections (5) making *C. trachomatis* the most common ocular pathogen in infants (6). In sexually transmitted chlamydial infections, other factors such as repeated exposure, asymptomatic (unapparent) and/or persistent infections make diagnosis difficult. Although antibiotics can clear many chlamydial infections, they do not prevent re-infection.

In vitro antibiotics can drive Chlamydiae into a persistent, nonculturable state (7). Persistently infected cells in vitro are resistant to azithromycin (8). Animal studies suggest (9) that early antibiotic treatment may interfere with the development of some natural protective immunity, and thus pre-dispose patients to more extensive pathology associated with pelvic inflammatory disease and worse sequelae. Genital infections also predispose to development of a significant proportion of reactive arthritis cases in which viable, metabolically active organism is present in synovium (10, 11). For recent reviews on Chlamydiae, see, for example, Ref 12).

Trachoma, the leading cause of infectious blindness in humans (13, 14), is caused by repeated ocular infection with ocular biovars of *C. trachomatis*. Of the tens of millions of people suffer from trachoma, up to one-fourth become blind. Trachoma has largely disappeared from North America and Europe, where extraocular chlamydial infections remain of great importance. *Chlamydia pneumoniae* (Cpn), a cause of community-acquired pneumonia in adults, has been associated with atherosclerosis (15,16); seroepidemiologic studies suggest that the majority of adults have been exposed to Cpn. Cpn has been associated with other chronic inflammatory diseases including late onset Alzheimer's disease (17, 18), one or more forms of multiple sclerosis (19, 20), and temperomandibular joint disease (TMJD) (21, 22, 23) A link between atherosclerosis and Alzheimer's disease (AD) is suspected in some cases (e.g., 24).

*C. psittaci* infects avian species and can have major economic impact on the poultry industry, affecting not only production, but also endangering poultry handlers (25). Thus, the public health significance of chlamydial infection is enormous. A genus-specific protective vaccine with broad protective capacity beyond selected serovars of *C trachomatis* would have great value.

Nanoencapsulation and Delivery of Vaccine Candidates.

Novel delivery methods for vaccine candidates have been developed over the past decade. With the advent of nanotechnology and "nanomedicine," therapeutic uses for nanoparticles (NP) has rapidly expanded. The present inventors and colleagues reported on their use of poly(lactic-co-glycolic acid (PLGA) microsphere-encapsulated protective antibodies as a chlamydial vaccine which was delivered orally and intranasally (26, 27). The present inventors and colleagues have recently found that nanoparticles are rapidly taken up into *Chlamydia*-infected cells in vitro, and that nanoparticles can be targeted to infected tissues (e.g., 28,29,30). Others have shown that PLGA nanoparticles can be used to deliver peptides, oligomers (DNA) or drugs in vivo (31-36). NP formulations with alternative polymers such as chitosan or alginate have been successful for mucosal delivery (31,37). The effects of the size and surface characteristics of the NPs have been investigated, (38, 39)

The present inventors and colleagues originally tested their first vaccine candidate in microspheres in part because nanosized materials for similar drug and peptide delivery were not yet available. Encapsulation has at least two major advantages: (1) an encapsulated vaccine antigen ("Ag") such as a monoclonal antibody (mAb) or a peptide or polynucleotide could be delivered orally without loss of function because of protection from gastric acids. Alternatively, intranasally or trans-tracheally delivered antigens in NPs would remain in the nasopharynx or lungs long enough to enter local antigen-presenting cells such as lung macrophage or dendritic cells (DC).

The 1990's dogma was that uptake of particle-based vaccines/antigens to mucosally immunize via uptake at Peyer's patches required particles with diameters of 1-10 μm (40, 138). Since then, Amidi et al., (31), Saltzman and others have demonstrated that NPs (<500 nm diameter) could not only successfully be delivered mucosally and immunize against the Ag delivered, but could be more efficient. Part of the latter success is due to Ag-loaded NPs inducing DC maturation (36); NPs are efficiently taken up both by DCs and macrophages (141). NP size delivery vehicles remain under study (38, 41, 137) and the potential for newer materials and NP designs have broadened their appeal as vaccine delivery vehicles.

PLGA co-polymer is FDA-approved for human use (dissolving sutures) and acts as a slow delivery device compared to free Ag, besides its adjuvant properties (42). PLGA NPs can be (a) fluorescently labeled to follow uptake in cells and tissues, (b) targeted to specific types of cells, and (c) conjugated to polyethylene glycol (PEG), also known as "pegylation" to sustain their circulating half life. Presumably nanosized particles containing vaccine candidates can be taken up at sites other than the Peyer's patches, probably by pinocytosis into enterocytes or DCs which locally sample the gut or other mucosal surface for foreign Ags. Upon recognition and uptake by DC, these Ag-presenting cells travel to the regional draining lymph nodes; Ag released from NPs inside the DC will be presented to T lymphocytes. This activates T cells which respond upon subsequent exposure to the immunizing Ag (or the whole organism, in this case, *C. trachomatis*). Such responses are required to clear infectious organisms from the mucosal sites.

Chlamydial Biology and Vaccine Targets

Figure 1:
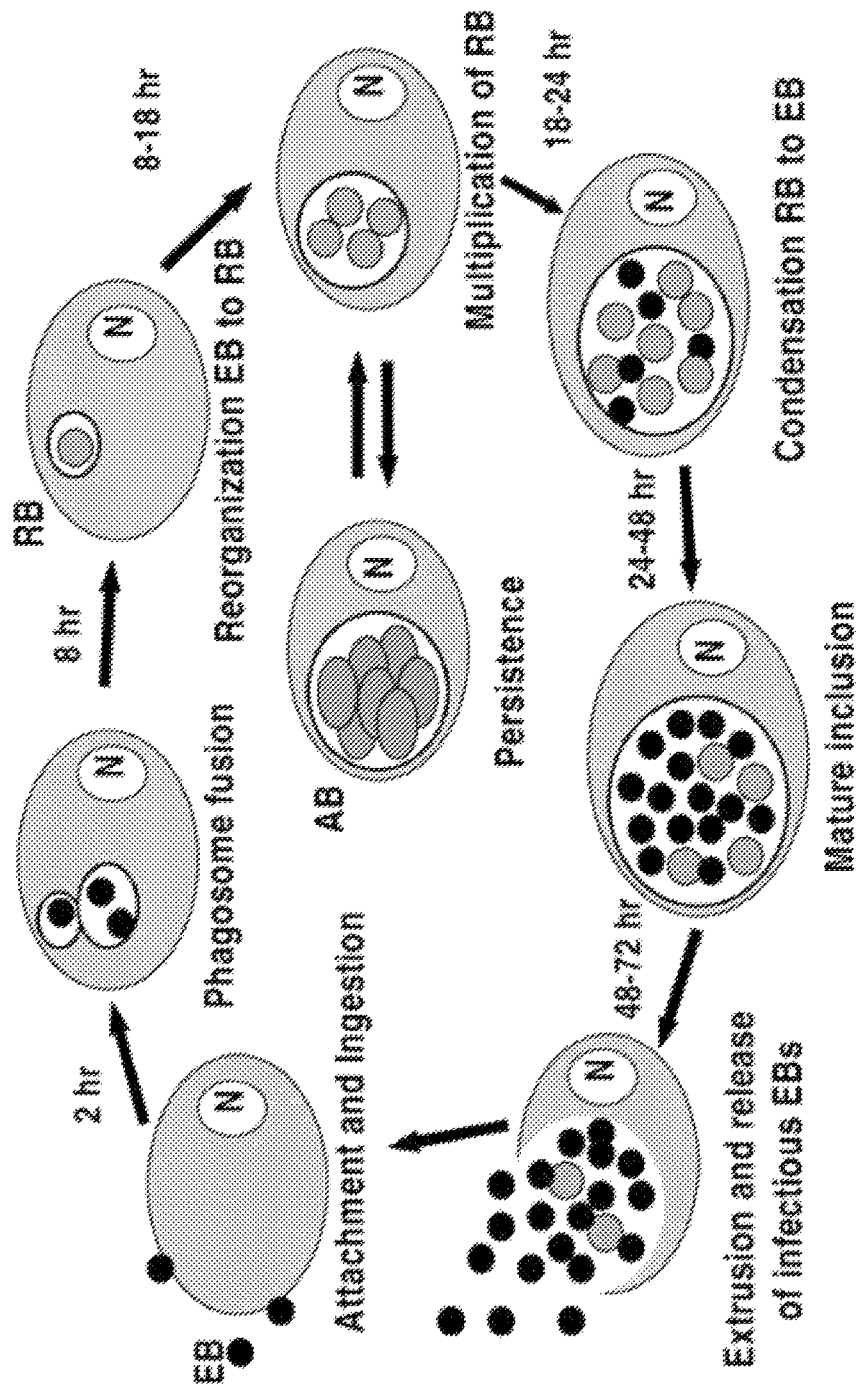

Chlamydiae are complex, obligate intracellular bacteria with a biphasic developmental cycle: (a) the elementary body (EB) which is infectious but metabolically inactive like a spore and (b) the reticulate body (RB) which is non-infectious but metabolically active. A schematic representation of the developmental cycle is shown in FIG. 1. A simple view is that immune responses to both the extracellular EB via antibody ("Ab") and intracellular stages (RB and EB), plus responses to the persistent form of "aberrant bodies" ("AB") via potent CD4 T cell responses and perhaps CD8 cytotoxic T cells are required for the "perfect" vaccine.

Figure 2:
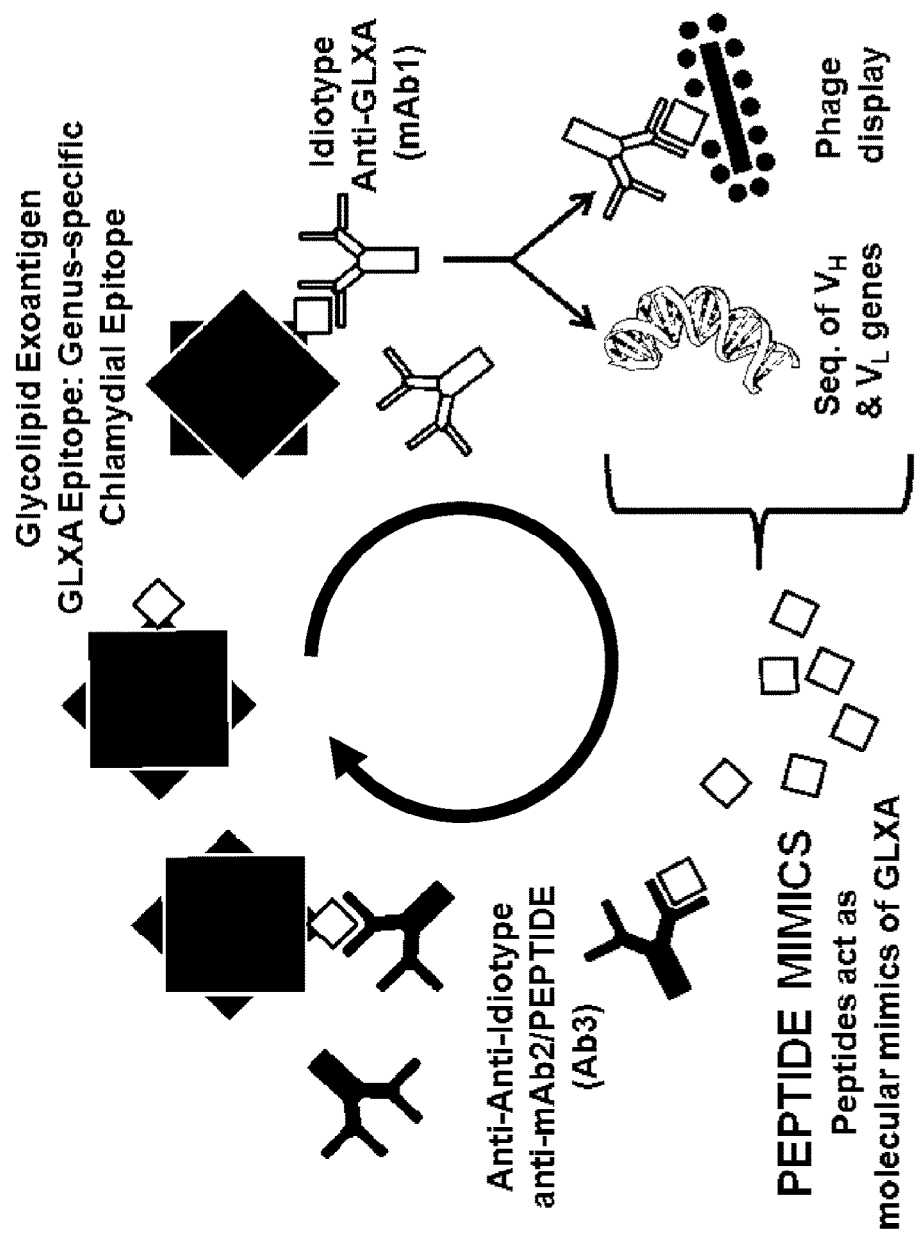

FIG. 2 is a schematic drawing depicting the earlier mAb2 vaccine candidate which was delivered in microparticles (26, 27) and its replacement by peptide mimetics.

Novel vaccine strategies are needed for chlamydial infections as traditional approaches with purified Ag or recombinant peptides have failed to protect, despite their immunogenicity (46, 47). Some of the difficulty in designing a protective vaccine approach relates to the use of a variety of different animal models. Newer molecular and biochemical methodologies have provided highly immunogenic Ag constructs/peptides which may induce protective cytotoxic T lymphocyte (CTL) responses (48), allow novel DNA vaccine constructs for the "major outer membrane protein" (MOMP) Ag or tests of new adjuvants such as CpG, (47, 49, 50)). An alternative approach adopted by the present inventors, is to use peptides derived by standard, accepted methods as vaccine candidates. During the past 10 years, peptides with sequences derived from anti-idiotypic (Anti-Id) Abs (which include mAbs) or conventional mAbs were shown to immunize or protect against several infectious agents and have been used extensively for cancer vaccine development (142-144).

Anti-Chlamydial Immunity can be Protective or Pathogenic

Primary chlamydial infection does not lead to lasting immunity against subsequent re-infection (51-53). The immunopathogenic responses to infection complicate vaccine development. After primary infection, part of the local immune response to re-infection appears to be a destructive local CD4+ T cell-mediated delayed-type hypersensitivity (DTH) response to hsp60 or to another chlamydial Ag (54-58).

The complex immunology of chlamydial infection has been extensively studied in several models (60), but the cellular and molecular requirements for protective immunity remain largely unelucidated. DCs pulsed with MOMP peptides appeared immunogenic, but failed to protect against *C. muridarum* (MoPn) genital challenge even though DC delivery of killed MoPn was protective (59, 60). Igietseme et al. (61) showed protection in mice immunized with EB-pulsed DC obtained from IL-10 knockout (KO) donors, and that DC with the IL10KO more rapidly stimulated Th1 responses in an IFNγ-dependent manner. This group showed earlier that chlamydial Ag-Ab complexes increased DC uptake of Ag via engagement of the cells' FcR to generate better effector responses in vitro and in vivo (62, 103). These results complement other studies showing that Ags directed to APCs via FcR engagement can shift pro-inflammatory immune responses to anti-inflammatory immune responses to those same Ags (63, 64). Coupled with recent results of Morrison (79) regarding an important B cell component to CD4-mediated clearance of infection, it is now clear that both T and B cells are required for anti-chlamydial protective immunity.

Mucosal immune responses to *Chlamydia*, including neutralizing Ab, are believed to be required for protection from infection although presence of neutralizing Ab alone does not assure protective immunization, presumably in part because of the chlamydial Ag targeted. Vigorous Ab responses to numerous chlamydial Ags, such as MOMP, a *Chlamydia*-secreted protease factor designated CPAF and lipopolysaccharide (LPS), measured in sera or secretions of infected individuals supported the vaccine potential of one or more of the latter, and most of these have been tested with varying success, e.g., (47, 49, 65. 66). An LPS-based vaccine was not protective although LPS is genus-specific (145). MOMP based vaccines are serovar-specific, in contrast to the genus-wide protective immunogens of the present invention, and would require cocktail vaccine approaches.

The genus-specific, secreted chlamydial glycolipid exoantigen ("GLXA"), which is distinct from LPS (67-74), is an immunogenic and also an immunologically relevant a target. Abs from patients infected with *C. trachomatis, C. psittaci,* and Cpn react to GLXA (81). Many anti-chlamydial immune responses are T cell-dependent. Specific T cell responses to MOMP and other Ag have been shown, and CD4 cells have a role in clearance (75-80).

Recent new chlamydial Ags include those identified by proteomic screening of patient samples (81). Barker et al. (82) recently showed a chlamydial T cell antigen, NrdB representing a ribonucleotide reductase small chain protein. Karunakaran et al. (83) used immunoproteomics to identify novel peptides bound by MHC Class I or II molecules with the *C. muridarum* mouse model. Cytokine/chemokine responses to the MoPn and other serovars suggest that activation of both Th1 and Th2 CD4 cells are important in clearance (84-87)). However, higher levels of IL-10 have been related to susceptibility to MoPn (88). Shifts in dominant Th have been associated with protection against other intracellular pathogens such as *Leishmania* and *Mycobacteria* (89-91), but this effect has yet to be been shown for any chlamydial vaccine candidate. The mAb2-induced isotype shifts in anti-GLXA Ab3 suggest the anti-Id vaccine induces both Th1 and Th2 cell-mediated anti-GLXA responses which are profoundly affected by the route of immunization.

According to the present invention, the protective peptide vaccine candidates with the appropriate Th and CTL epitopes will induce both Th1 and Th2 responses and probably CD8$^+$ CTL responses, respectively.

Most of the expected responder/effector cells and their cytokines have been found during chlamydial infection and clearance (85, 92). However, these immunohistochemical (IHC) approaches have been focused on innate and adaptive immune responses to infection rather than on responses to vaccination. Studies with transgenic (Tg) and KO mice have suggested that MHC Class II+ T cells are critical in chlamydial (MoPn) clearance, whereas T cells involved in MHC Class I pathway are not (93). It is more likely that a continuum of Th1 vs Th2-associated responses occurs (94, 95)), and many factors including Ag-processing pathway(s) (96) influence the outcome.

A potential protective mechanism in chronic chlamydial inflammatory disease is mediated by regulation of pro-inflammatory Th1 cell and monocyte/macrophage/DC responses. Roles for CD8+ T cells in responses to this intracellular pathogen have long been suggested, and evidence for CD8+ CTL against both *C. trachomatis* and Cpn has been published (48,97-99). However, immunogenic and protective peptides that induce CD8 responses across serovars or species have not yet been demonstrated. Manipulation of APC, particularly DCs pulsed with (UV)-EB induced varying levels of protective immunity. For example, DC exposed to live EB acquired a more mature DC phenotype than that seen with UV-EB and produced higher levels of IL-12 which would enhance CD4 Th1 responses (113, 114).

Development of chlamydial vaccines development requires
 (1) identification of one or more target Ags,
 (2) induction of better protective responses to overcome pathogenic immune responses, and
 (3) lasting protection against primary, secondary, and heterologous infections in one or more animal models.

Real clinical exposures to *Chlamydia* are presumably low dose and thus minimally immunogenic (until in vivo replication begins). So care is required in interpreting evidence of immune responses to large challenge doses in animal models as these may reflect multiple pathways of stimulation which differ from more subtle responses to natural infection. Since previous infection alone does not induce fully protective immunity in humans, and because single infections are usually self-limited, it is even more important to identify and induce immune responses which go beyond those described above without exacerbating the inflammatory component. A new question has been articulated recently in response to the observation that early antibiotic treatment of chlamydial infections may abrogate development of some natural protective immunity, and in this way could lead to worse late sequelae such as infertility (146, 147).

On the other hand, natural clearance of organism may not represent the required response(s) for protective immunity. Do highly immunodominant Ags obscure potentially protective responses to other Ags? Achieving a balance between protective and pathogenic immunization is important for a vaccine for human populations that are continuously re-exposed or were previously exposed to *Chlamydia*. Understanding how to inhibit dissemination and establishment of chronic infections at nonmucosal sites, and the effect of any antichlamydial vaccination on these events are critically important. The present invention identifies the effect of peptide immunogens, such as those derived from the sequence of mAb2 variable regions on such a balance and on disseminated chlamydial infection which reflects human disease.

*Chlamydia trachomatis* and Animal Models of Disseminated Infection

A new appreciation has emerged recently about the dissemination phase of chlamydial infections. Circulating cells (probably monocytes and/or monocyte-derived DCs) traffic and collect, or are trapped, at one or more sites. A common site for *C. trachomatis* dissemination is the synovium, and indeed, a subset of patients develops reactive arthritis (ReA). Chlamydiae are the only viable and metabolically active bacteria in ReA synovium, and are in a molecularly-defined persistent form (as to morphology and gene expression) when patients present to the rheumatologist (10, 100-107).

The synovium has been postulated to be a site of entrapment of infectious organisms, circulating particulates, etc. IHC and immunoelectron microscopic studies showed that both intact *Chlamydia* and chlamydial Ags are present in the ReA synovium, ((110, 11)). However, isolation of culturable *Chlamydia* from joints was reported only once (112); most attempts failed (106)). Under some conditions, *C. trachomatis* generates persistent infection (10, 101, 107, 113-116), though very low levels of EB are produced, and a number of genes encoding MOMP, chsp60, ftsK, ftsW, etc. are either down- or up-regulated.

Many groups, including the present inventors have developed PCR-based *Chlamydia* detection systems, (117-122). With the publication of genomes for several *C trachomatis* serovars, PCR/qPCR for additional chlamydial gene transcripts has become possible. The *C. trachomatis* genome project has enabled the present inventors' own studies of selected chlamydial genes expected to be aberrantly expressed when the organism enters a persistent state. Targeting selected genes involved in specific stages of chlamydial development and differentiation indicates that chlamydial gene expression in actively infected cells differs significantly from that observed in ReA synovial tissues and in persistently infected human monocytes in vitro (118,123). Remarkably few animal studies have investigated *Chlamydia*-associated ReA.

The present inventors and colleagues were the first to show vaccine-mediated reduction in experimental ReA in mice. Initially, ocular infection of mouse conjunctivae (an ocular mucosal tissue) resulted in chlamydial dissemination to synovium (124). More recently, the present inventors focused on a genital infection model—more representative of human *Chlamydia*-associated ReA cases in the US and Europe. In the latter models *C. trachomatis* dissemination to synovial tissues and consequent knee pathology were documented.

An overview of the synovial inflammation induced in the present inventors' murine ocular and genital infection models has been published (124-126). Chlamydial dissemination occurs in other animal models: Cpn was shown (127), to disseminate to distant sites after intranasal challenge of mice or after transfer of infected PEC, but neither synovium nor the CNS was assayed. Studies (128) with MoPn-induced genital infection resulted in an acute arthritis. The latter studies utilized either presensitization or intra-articular chlamydial challenge, making them a poorer mimic of natural dissemination from a genital infection. The same group (129) showed dissemination of GPIC (*Chlamydiophila pecorum*) from genital tract to joint in guinea pigs. A recent inbred rat model of chlamydial ReA (130) utilizes intra-articular injection of synoviocytes infected with *C. trachomatis*. While allowing examination of some questions relevant to ReA, it differs fundamentally from natural human infections in which the initial infected cell is not fibroblastic, nor would this be the host cell involved in chlamydial dissemination to joints. Therefore, the present inventors' model for *C. trachomatis*-associated ReA is advantageous for developing and testing of the vaccines of the present invention, and most particularly for study-mediated reduction of chlamydial ReA and synovial infection because of its noninvasive mode of disease generation.

The present inventors' Identification of an effective vaccine coupled with an effective delivery strategy to protect against chlamydial infections should have enormous public health impact worldwide. The encapsulation of immunogenic peptides into biodegradable NPs will facilitate better mucosal vaccination, help reduce cold chain requirements This invention represents novel approaches to prevention of *Chlamydia*-associated diseases, as nanotechnology has not been applied previously to studies of *Chlamydia*. Further, the approaches developed in accordance with this invention will serve as a basis for the development of vaccine formulations for other intracellular human pathogens.

There currently is no protective chlamydial vaccine. Sexually transmitted infections are largely asymptomatic in women and this can lead to ascending infections, pelvic inflammatory disease, ectopic pregnancies and infertility. Despite widespread screening and treatment programs, the numbers of cases of chlamydial sexually transmitted infections (STI) are still increasing and represent over one million new STI cases/year in 2007. Because these antigenic epitopes are genus-specific (genus-wide), not serovar-specific or supposedly biovar-specific (*C. trachomatis* vs. *C. pneumoniae* vs *C. psittaci*) the present vaccine compositions should protect against STI, cardiovascular disease, chlamydial pneumonia, some subsets of Alzheimer's disease and multiple sclerosis, not to mention chronic inflammatory disease sequelae like infertility.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present inventors have identified and/or deduced the sequences of peptides representing antigenic epitopes as well as peptides representing part or all of the combining region of the anti-Id mAb2 specific for antibodies specific for chlamydial GXLA antigens. As described herein, various peptides were tested and found to induce antibodies which recognize EB and RB, and components of inclusions (matrix material and/or inclusion membrane) in infected cells. Importantly, these peptides manifest protective activity against challenge with infectious *Chlamydia* and represent genus-specific antigens with broader potential as anti-chlamydial vaccines across *C trachomatis*, *C pneumoniae*, *C psittaci*, *C pecorum*, etc.

The present inventors conceived that the hypervariable or complementarity determining regions (CDR) of the H- and L-chains of the IgG molecules of mAb2 are candidate vaccines because together they represent the Ag combining region of these mAb2 IgG molecules. Anti-Id vaccines have been studied extensively as anti-cancer vaccine candidates (43-45).

The present invention is directed to novel immunogenic peptides and their encapsulation into biodegradable NPs to facilitate better mucosal vaccination. The invention provides novel compositions and methods for prevention of *Chlamydia*-associated disease and applies nanotechnology to the prevention and treatment of *Chlamydia* infections. The present invention provides a new composition that is a conceptual leap forward from an earlier discovery of one of the present inventors and colleagues (see U.S. Pat. Nos. 5,656,271 and 5,840,297 and Ref 27) of an anti-Id mAb termed "mAb2" made against an anti-GLXA mAb (mAb1) which serves as a molecular mimic of one or more GLXA epitopes (which structures have not yet been biochemically defined).

GLXA is difficult to purify and requires large amounts of *chlamydia* for adequate material. Because of this, this Ag has never been adequately characterized so its exact nature remains unknown. What is known that it is a "genus-specific" (also termed "genus-wide") antigen, meaning that it is present in organisms of the *chlamydia* genus, across known species. It is distinct from chlamydial lipopolysaccharide (LPS), the only other known genus-wide antigen in *chlamydia* (26, 27, 68-74, 126).

The present inventors' novel approach is designed to avoid the need for GLXA characterization and purification by focusing on advantageous peptide immunogens. They are easily produced in mass quantities economically. They can be conjugated to immunogenic carriers and/or encapsulated in a variety of delivery vehicles including microspheres, NPs and virus-like particles (VLP) for more efficient delivery and immunization and/or conjugated to other nanomaterials such as dendrimers/dendritic polymers (which terms are used interchangeably).

According to the present invention, the immune sera induced by peptide immunization recognize persistently infected cells and bind to Chlamydiae which are in a persistent state. Therefore, immunity to one or more of the peptides would have the potential to clear persistent infection and thereby prevent chronic chlamydial infections.

More specifically, the present invention is directed to an immunogenic peptide of at least about 10 amino acids in length, but shorter than the length of an antibody $V_H$ or $V_L$ domain or a single chain antibody (scFv) chain. This peptide is characterized in that it mimics immunologically the structure of the *Chlamydia* genus-specific glycolipid exoantigen (GLXA) so that when the peptide is administered to a mammalian subject in an adequate amount and in immunogenic form, it induces an antibody response that is measurable using, for example:

(a) an immunoassay against the immunizing peptide,
(b) an immunoassay against GLXA, and/or
(c) an immunoassay or biological assay that measures binding to, or inhibition of function. growth or survival of, *Chlamydia* organisms of multiple chlamydial species (preferably all).

The above immunogenic peptide preferably does not exceed about 11 or 12 or 13 or 14 or 15 or 16 or 17 or 18 or 19 or 20 or 25 or 30 or 35 or 40 or 45 or 50 of 60 of 70 or 80 of 90 or 100 amino acid residues in length (and all values in between), and most preferably does not exceed about 30 amino acids.

The immunogenic peptide may be derived from a phage display peptide library by selection for binding with an anti-GLXA antibody Ab1. One defined anti-GLXA antibody Ab1 is a mAb produced by a hybridoma cell line deposited in the ATCC as accession number HB-11300

In one set of embodiments, the above immunogenic peptide is selected from the group consisting of (as defined in more detail below): (a) Pep1, SEQ ID NO:1; (b) Pep2, SEQ ID NO:2; (c) Pep3, SEQ ID NO:3; (d) Pep1, SEQ ID NO:4; (e) Pep4, SEQ ID NO:5; (f) Pep5, SEQ ID NO:6; (g) Pep6, SEQ ID NO:7; (h) Pep11, SEQ ID NO:11; (i) Pep12, SEQ ID NO:12; (j) Pep13, SEQ ID NO:13; (k) Pep14, SEQ ID NO:14; and (l) a conservative amino acid substitution variant or addition variant of any of the peptides of (a)-(k) that retains the antibody reactivity and immunogenicity of the peptide.

The immunogenic peptide may also be a cyclic peptide in which an N-terminal and a C-terminal residue is added to introduce a Cys residue at both termini or a cross-linkable Lys (K) at one terminus and Glu (E) at the other terminal. Preferred examples of such peptides are those with linear sequences selected from SEQ ID NO:14; SEQ ID NO:15; SEQ ID NO:16; SEQ ID NO:17; SEQ ID NO:18; SEQ ID NO:23; SEQ ID NO:24; SEQ ID NO:25; SEQ ID NO:26; SEQ ID NO:27; SEQ ID NO:28; SEQ ID NO:20; SEQ ID NO:30; SEQ ID NO:34; SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; SEQ ID NO:50; SEQ ID NO:51; SEQ ID NO:52; SEQ ID NO:53; SEQ ID NO:54; SEQ ID NO:55; SEQ ID NO:56; SEQ ID NO:57; and SEQ ID NO:58.

In a preferred embodiment, the immunogenic peptide is one with an amino sequence of a V region domain of an anti-Id antibody Ab2 that is specific for an anti-GLXA antibody Ab1, which peptide binds to an anti-GLXA antibody in an immunoassay. The anti-GLXA antibody Ab1 may be a mAb; a preferred example is the mAb produced by a hybridoma cell line deposited in the ATCC as accession number HB-11300. The anti-Id Ab2 antibody is preferably a mAb (a mAb2), a preferred example of which is the mAb produced by a hybridoma cell line deposited in the ATCC as accession number HB-11301. Preferred peptides derived from this mAb2 are (a) Pep8, SEQ ID NO:8; or (b) Pep9, SEQ ID NO:9; or (c) Pep10, SEQ ID NO:10; or (d) a conservative amino acid substitution variant or addition variant of any of the peptides of (a)-(c) that retains the antibody reactivity and immunogenicity of the peptide.

The immunogenic peptide that is derived from, or is similar to, a peptide sequence of a mAb2 is a cyclic peptide in which an N-terminal and a C-terminal residue, such as Cys residues at both termini or a cross-linkable Lys at one terminus and Glu at the other terminus. Preferred cyclic peptides of this group are those with a linear sequence which is selected from the group consisting of SEQ ID NO:22, SEQ ID NO:23; SEQ ID NO:24; SEQ ID NO:25; SEQ ID NO:38; SEQ ID NO:39; SEQ ID NO:40; SEQ ID NO:52; SEQ ID NO:53; and SEQ ID NO:54.

Also provided is an immunogenic linear oligomeric or multimeric peptide or polypeptide that comprises between about two and about 20 repeats of the peptide of any of the above peptides (monomeric units). Such oligomers or multimers may comprise one or more linker peptides, each between any two adjacent repeating "basic" units of the peptide. The oligomer or multimer may be cyclized.

Another preferred embodiment is an immunogenic tandem oligomeric peptide that comprises two or three repeats of the above peptide monomer linked in tandem (side-by-side).

One embodiment is a dendritic polymer built on a core molecule which is at least bifunctional so as to provide branching and contains up to 16 terminal functional groups wherein a peptide monomer (or oligomer or multimer) is covalently linked to the functional groups of the dendritic polymer.

The present invention is also directed to an immunogenic pharmaceutical composition comprising
  (a) the immunogenic peptide, oligomer or multimer or dendritic polymer above; and
  (b) an immunologically and pharmaceutically acceptable carrier or excipient.

The immunogenic composition preferably further comprises microspheres or nanoparticles comprising a solid matrix formed of a pharmaceutically acceptable polymer which microspheres comprise the peptide. Preferred polymers are polylactic acid (PLA) or PLGA.

In the above composition, the peptide (or the oligomer or multimer) may be linked to a filamentous bacteriophage.

The peptide oligomer or multimer may be linked to, or associated with, or mixed with a targeting moiety. The targeting moiety is preferably a polypeptide that promotes binding to, or selective targeting to, a the surface of a desired cell type or a desired milieu. Most preferably, the targeting moiety is an antibody (or antigen-binding portion or variant of an antibody) that binds to a cell surface antigen of a cell being targeted. Most preferred is an antibody that promotes binding/targeting and processing of the immunogenic moiety to an antigen-presenting cell, most preferably a dendritic cell (DC) (or an immature DC or DC precursor).

The above immunogenic composition may further comprise an adjuvant, an immunostimulatory protein (different from the immunogenic peptide/polypeptide), or a CpG oligonucleotide. Examples of preferred immunostimulatory proteins are cytokines, such as interleukin-2 or GM-CSF.

Examples of preferred adjuvants are
(a) ISAF-1 (5% squalene, 2.5% pluronic L121, 0.2% Tween 80) in phosphate-buffered solution with 0.4 mg of threonyl-muramyl dipeptide;
(b) de-oiled lecithin dissolved in an oil;
(c) aluminum hydroxide gel;
(d) a mixture of (b) and (c)
(e) QS-21; and
(f) monophosphoryl lipid A adjuvant.

The immunogenic composition may comprise both an adjuvant and an additional immunostimulatory moiety, such as a cytokine, preferably IL-2.

The present invention is also directed to an immunogenic DNA molecule. Preferably, the immunogenic DNA encodes one or more of the above peptides of the invention.

The immunogenic DNA molecule may encode a polypeptide that comprises, in any order, one, two or three CDRs (CDR1, CDR2 or CDR3) of a $V_H$ or $V_L$ region of an Ab2 anti-Id antibody specific for an Ab1 that is an anti-GLXA antibody. The anti-Id antibody is preferably a mAb, for example, the mAb produced by the hybridoma cell line deposited in the ATCC under accession number HB-11301. Preferred examples of DNA molecules are those that comprise SEQ ID NO:59 or SEQ ID NO:61, or at least one CDR coding region of SEQ ID NO:59 or SEQ ID NO:61. One preferred embodiment are the DNA molecules SEQ ID NO:59 or SEQ ID NO:61, or a fragment of these sequences that encode at least one CDR.

When the DNA molecule comprises SEQ ID NO:59, the molecule preferably does not exceed about 411 nucleotides in length, though it may be significantly shorter. When the DNA molecule comprises SEQ ID NO:61, the molecule preferably does not exceed about 387 nucleotides in length, though it may be significantly shorter.

In one embodiment, the immunogenic DNA molecule encodes a linear peptide oligomer or multimer as above. In another embodiment, the immunogenic DNA molecule encodes a single chain fusion polypeptide which polypeptide comprises (a) as a first fusion partner, a peptide as above, (b) optionally linked in frame to a linker or spacer peptide, which, if present, is linked in-frame to (c) a second fusion partner. When a subject is immunized with this chimeric DNA molecule, the antibody response against the peptide is augmented compared to an antibody response induced by the same peptide that is administered without being linked to the second fusion partner (with or without a linker/spacer).

The immunogenic DNA molecule is preferably in the form of an expression vector expressible in cells of the intended subject of the immunogen, preferably a human. Such an expression vector comprises (a) the DNA molecule as set forth above; and (b) operatively linked thereto, a promoter and, optionally, one or more transcriptional regulatory sequences that promote expression of the DNA in the intended cell or subject.

The present invention also provides a method of immunizing a mammalian subject, preferably a human, against *Chlamydia* infection. The method comprises administering to the subject an effective immunogenic amount of
  (a) the above immunogenic peptide, or
  (b) the above oligomeric or multimeric peptide or polypeptide or polymer, or
  (c) the above fusion polypeptide; or
  (d) the above DNA molecule or expression vector; or
  (e) the above immunogenic composition
that induces an antibody response specific for chlamydial GLXA antigen, which antibody response is *Chlamydia* genus-side (genus-specific). The above method preferably induces an antibody response which is a neutralizing antibody response that prevents or inhibits infectivity, growth, or spread of, or pathogenesis by, the *Chlamydia* in the subject (e.g., reactive arthritis).

BRIEF DESCRIPTION OF THE DRAWINGS

FIG. 1 shows a schematic representation of the developmental cycle of *Chlamydia* infection. RB: reticulate body—a non-infectious but metabolically active form of the organism. The prime purpose of RBs is intracellular replication by binary fission using host metabolites. EB: Chlamydial elementary bodies, a spore-like, spherical particle, about 300 nm in diameter (infectious but metabolically inactive).

FIG. 2 is a schematic representation depicting the earlier mAb2 vaccine candidate and the idiotype network as it applies to antibody responses to chlamydial antigen GLXA.

FIG. 3 is a series of graphs showing antibody responses (measured in ELISA) of peptide-immunized mice against individual peptides. Each group of mice exhibited increasing antibody responses to the respective immunizing peptide with successive immunizations; prebleed control values were subtracted from each mouse's serum Absorbance (or OD) at respective dilutions.

FIG. 4 is a series of graphs showing cross-reactivity between peptides in ELISA.
Im#—mice immunized with Pep4, Pep7 or Pep8; "X-Rx": cross reactivity with noted in the panels. Sera from mice immunized with Pep4 or Pep7 were cross-reactive with Pep7 and Pep4, respectively. Pep8 did not cross-react with Pep10 (since the latter peptides represent distinct H-chain CDR.

FIGS. 5 and 6 show the results of adoptive transfer of spleen cells from mAb2-immunized donors to immunocompromised SCID mice that were subsequently challenged with *Chlamydia trachomatis* (K serovar). FIG. 5 shows the resulting infectious bacterial load which increased without immune cell transfers. FIG. 6 shows antibody responses (in ELISA) against four of the peptides of this invention. Symbols are as follows: □-□: transfer of mAb2-immune lymphocytes (including T cells); ●-●: transfer of T cell-depleted mAb2-immune lymphocytes; ○-○ transfer of normal (control) lymphocytes; these three groups were challenged with *Chlamydia*. ▲-▲: transfer of normal (control) lymphocytes; recipients were not infected and no anti-peptide antibody responses were detected.

FIGS. 7 and 8 show results with mice that had been immunized with the earlier mAb2 vaccine in microencapsulated form after challenge with *C. trachomatis*, serovar E. FIG. 7 shows viral shedding 14 days after bacterial challenge; several mice have overlapping values. FIG. 8 shows antibody responses of the same animals against the indicated peptides measured in ELISA. The groups were immunized (or not) either subcutaneously (SC), orally (PO) or by both routes and infected (or not) with Serovar E *C trachomatis*. Only groups K, L, M and P were tested in the initial anti-peptide ELISA.

| Group (n = 4-5) | Immunization | Infection (E serovar) |
|---|---|---|
| K | SC × 3 | Yes |
| L | None | No |
| M | None | Yes |
| N | PO, SC × 2 | Yes |
| O | SC, PO × 2 | Yes |
| P | PO × 3 | Yes |

FIGS. 9A-9F show that peptide-immune sera recognize *C trachomatis*-infected HEp-2 cells. Micrographs of HEp2 cells infected with *C. trachomatis* are immunostained (by indirect immunofluorescence) with sera (1:40 dilution) from mice immunized with the designated peptides (A-E) or soluble. mAb2 (F). FITC anti-mouse IgG was the detecting antibody. Arrows point to distinct differences in targets of the immune sera. Antibodies in panels A-C recognized EB and RB and possibly some matrix material in the inclusion. Antibodies in D-E also recognized targets in the inclusion matrix and inclusion membrane, similar to immune sera raised against the older vaccine candidate, the entire mAb2 (F). 40× original magnification. Samples are counterstained with Evans blue.

FIGS. 10 and 11 are graphs showing the results of immunostaining of chlamydial organism in vaginal smear cells (direct fluorescence) at 7 days (FIG. 10) and 14 days (FIG. 11) after infection.

FIG. 12 is a photomicrograph of PLGA NPs loaded with the peptide Pep4 viewed by scanning electron microscopy. Length scale is shown FIGS. 13A and 13B are graphs showing release profiles of peptide 4 from NPs. In FIG. 13A, release was determined by reverse phase HPLC (NPs in phosphate buffered saline (PBS) or carbonate buffer. FIG. 13B shows results of immunochemical analysis of released peptide 4 (in carbonate buffer) examined by ELISA with known positive anti-Pep4 antiserum.

FIG. 14A-14F are photomicrographs of McCoy cells (148) persistently infected with *Chlamydia trachomatis* as a result of Penicillin G (PenG) addition at 1 hr ($t_0$) (A-C) or at 18 hrs ($t_{18}$) (D-F) after infection with the organisms. Cells were fixed in methanol 48 hrs post infection and stained with antisera form animals immunized with Pep4 (A,D), Pep7 (B,E) or a mixture of Pep4 and Pep7 (C,F). Insets in panels D-F show a representative "control" infected cell (no PenG).

FIG. 15A-15C is a set of three photographs showing the gross morphology of tissues of the female reproductive tract of mice immunized and then challenged 28 days earlier with Pep4 or Pep7. Mice had been primed and boosted twice SC, as above, and were challenged with *chlamydia* 2 weeks later, rechallenged and sacrificed 4 weeks after re-challenge. Inflamed genital tracts outlined in dashed lines. At the arrow point is the uterine horn and it is very dark (inflamed, purple in situ) whereas those of Peptide 4 or 7 immunized mice were not nearly as inflamed and were lighter in color.

FIG. 16A-16B is a set of graphs showing results (ELISA) of repeat experiment of that shown in FIG. 3, of immunization of BALB/c mice (n=4-5) with Pep4 or an irrelevant peptide and testing reactivity of the animals' sera with Pep4.

FIG. 17A-17F show results in ELISA of sera of mice immunized SC with various doses of the Pep4 as immunogen antigen either as free peptide or encapsulated in PLA microparticles (Pep4-MP). MP's were loaded at levels of between about 7.5 and about 9 μg peptide per mg PLA. Δ-Δ: results of pre-bleeds (before immunization). (▲-▲: results after a single primary immunization. ○-○: results after $1^{st}$ boost. ●-●: results after $2^{nd}$ boost. ▼-▼: results at the time of terminal bleed (day 28). Each point represents the mean absorbance value ($OD_{405}$) for the sera of 4 or 5 individual mice of the designated group.

FIG. 18 shows results of direct fluorescent antibody staining (DFA) of vaginal smears obtained at the times indicated. The assay detected free elementary bodies (EB); the scores (in arbitrary units) indicate relative number of free EB in the smear (minimum of 1000 cells required for valid sample)

FIG. 19A-19B show time course of release of encapsulated peptide by Pep4 microparticles.

DESCRIPTION OF THE PREFERRED EMBODIMENTS

One of the present inventors and colleagues previously discovered that an anti-idiotypic (Id) monoclonal antibody mAb2 specific for an antibody (Ab1) that is itself specific for the "nominal antigen" chlamydial glycolipid antigen (GLXA) could serve as a molecular mimic vaccine that induced anti-anti-Id Abs (collectively Ab3) which recognized GLXA. See U.S. Pat. Nos. 5,656,271 and 5,840,297). This mAb2, made by a hybridoma cell line deposited in the ATCC as Accession No. HB-11301, immunized animals against *Chlamydia* and neutralized *Chlamydia* infection in vivo. Either a polyclonal Ab2 or a different monoclonal Ab2 could be used similarly. Ab1 (specific for GLXA) itself did not have any significant activity in either immunizing against or neutralizing *chlamydia. The preferred (and exemplified) mAb2* was induced by immunization with a mAb1 specific for chlamydial Ag (referred to herein also as "GLXA-mAb1" and made by a hybridoma cell line deposited in the ATCC as Accession No. HB-11300). This Ab1 is an Id Ab bearing one or more idiotypes associated with murine GLXA-specific Abs but does is not itself active in either neutralizing *chlamydia* nor as an immunogen that immunized against *chlamydia.*

The above mAb2, while immunogenic and protective, is a murine Ab so it has known disadvantages as a human vaccine due to the presence of mouse-specific epitopes that generate undesired immune responses in humans. Its potential utility is also compromised by the fact that certain murine (or partially murine) mAbs are in clinical use, and may therefore prime a subject for an undesirable, possibly dangerous, immune (including anaphylactic) response to a mAb2-type immunogen.

The present invention was conceived as a way to overcome these deficiencies by using, instead of a complete murine mAb or a full chain or domain thereof, either DNA encoding the chain/domain or peptides derived from a random phage display library or from antigen-binding regions (CDR's) of the mAb2 that mimic GLXA antigen.

Production and Characterization of Anti-GLXA (Ab1) Anti-Id (Ab2) Antibodies

In the following description, reference will be made to various methodologies known to those of skill in the art of immunology, cell biology, and molecular biology. Publications and other materials setting forth such known methodologies to which reference is made are incorporated herein by reference in their entireties as though set forth in full. Standard reference works setting forth the general principles of immunology include A. K. Abbas et al., *Cellular and Molecular Immunology* ($6^{th}$ Ed.), W.B. Saunders Co., Philadelphia, 2007; C. A. Janeway et al., *Immunobiology. The Immune System in Health and Disease,* $6^{th}$ ed., Garland Publishing Co., New York, 2005; P. Delves et al. (eds.) *Roitt's Essential Immunology* ($11^{th}$ ed.) Wiley-Blackwell, 2006; I. Roitt et al., *Immunology* ($7^{th}$ ed.) C.V. Mosby Co., St. Louis, Mo. (2006); Klein, J et al., *Immunology* ($2^{nd}$ ed), Blackwell Scientific Publications, Inc., Cambridge, Mass., (1997).

Additionally, methods particularly useful for polyclonal and monoclonal antibody production, isolation, characterization, and use are described in the following standard references: Harlow, E. et al., *Antibodies: A Laboratory Manual*, Cold Spring Harbor Laboratory Press, Cold Spring Harbor, N.Y., 1988); Harlow, E. et al., *Using Antibodies: A Laboratory Manual*, Cold Spring Harbor Laboratory Press, Cold Spring Harbor Laboratory Press, Cold Spring Harbor, N.Y., 1998; *Monoclonal Antibodies and Hybridomas: A New Dimension in Biological Analyses*, Plenum Press, New York, N.Y. (1980); H. Zola et al., in *Monoclonal Hybridoma Antibodies: Techniques and Applications*, CRC Press, 1982).

For preparation and partial purification of GLXA, see U.S. Pat. No. 5,716,793 (A. B. MacDonald et al.). The anti-GLXA antibody (Ab1) can be polyclonal or monoclonal. For production of mAb, an Id antibody GLXA-Ab1 is produced by immunizing an animal, typically a mouse, with GLXA or whole *Chlamydia* bacteria as the antigen. The sera of that animal can be a source of a polyclonal Ab1 which can be enriched or purified by any of a number of conventional methods. Immune spleen cells of the animal then are identified, isolated and fused with lymphoma or myeloma cells using conventional procedures. The fused cells then are incubated in a selective medium to prevent growth of unfused tumor cells. The hybridoma cells are cloned, e.g., by limiting dilution and supernatants are assayed for secreted mAb of desired specificity ore reactivity. MAbs antibodies also can be produced by growing hybridoma cells in vivo in the form of intraperitoneal ascites tumors. Alternatively, B lymphocytes producing anti-GLXA Ab can be immortalized by infection by Epstein-Barr virus.

A suitable and preferred hybridoma that produces GLXA-mAb1 is deposited in the American Type Culture Collection and identified as ATCC HB-11300. This mAb reacts with all 15 serovars of *C. trachomatis, C. pneumoniae*, and *C. psittaci* in an ELISA-type Enzyme Immunoassay (EIA), demonstrating recognition of a genus-wide antigen).

According to the present invention, the Id antibody specific for the nominal antigen GLXA GLXA-Ab1, preferably a mAb anti-GLXA Ab, most preferably, the mAb produced by the HB-11300 (see U.S. Pat. Nos. 5,716,793, 5,656,271 and 5,840,297), is used for two primary purposes:

(1) To identify peptides in a library, such as a random phage display library, that share conformation with a GLXA epitope (defined below as "Category 1" peptides); and (2) As a source of peptide sequences of the antigen-binding site, preferably CDR regions of the $V_H$ or $V_L$ domains, which represent idiotopes or "internal images" that are mimics of GLXA epitopes (defined below as "Category 2" peptides). These peptides are defined as being shorter than the length of an antibody $V_H$ or $V_L$ domain or a single chain antibody (scFv) chain (Skerra, A. et al. (1988) *Science,* 240:1038-41; Huston J S et al. (1988) *Proc. Natl. Acad. Sci. USA* 85:5879-83; Pluckthun, A. et al. (1989) *Methods Enzymol.* 178:497-515; Winter, G. et al. (1991) *Nature* 349:293-9; Jost C R et al., *J Biol Chem.* 1994 269:26267-73; U.S. Pat. Nos. 4,704,692, 4,853,871, 4,946,778, 5,260,203, 5,455,030).

The initial peptides that form the basis of the present invention were obtained or deduced in the following ways.

(1) "Category 1" Peptides.

The present inventors obtained peptide sequences from phage display library (PhD-12 peptide library from New England Biolabs, # E8110S) (see also, 131) by screening the library with GLXA-mAb1 (product of HB11300) specific for the GLXA to detect peptides that, by chance, mimicked GLXA. Based on several rounds of panning, a set of peptides bound by mAb1 was identified. Two peptides, Pep4 and Pep7, were initially selected for analysis and synthesized. (see Table 1). While the peptide identified and studied from this group are 12mers based on the way the library was constructed, the same procedure would work to identify peptides of a different size (longer or shorter) that would have similar immunological properties and would be used as immunogens in the same manner.

(2) "Category 2" Peptides

The heavy (H) chain variable domains ($V_H$) and light (L) chain variable domains ($V_L$) of mAb2 produced by hybridoma HB-11300 were cloned and sequenced. The peptides useful as immunogens to induce anti-GLXA/anti-chlamydial Abs includes peptides initially selected for study, and which form the basis for this "class" of peptides come from the $V_H$-chain sequences whereas others disclosed herein come from $V_L$-chain sequences.

The $V_H$ region of this mAb2 has the following DNA and encoded peptide sequences. (Nucleotide sequence is SEQ ID NO:59; amino acid sequence is SEQ ID NO:60. The three CDR regions are underscored and labeled.

```
att caa gta cag ctg gag gag tct gga cct gaa ctg agg aag cct gga
Ile Gln Val Gln Leu Glu Glu Ser Gly Pro Glu Leu Arg Lys Pro Gly gag gca gtc aag atc tcc tgc aag act tct ggt tat acc ttc aca gac
Glu Ala Val Lys Ile Ser Cys Lys Thr Ser Gly Tyr Thr Phe Thr Asp
                                        CDR-1→ tat tca atg cac tgg gtg aag cag gct cca gga aag ggt tta aag tgg
Tyr Ser Met His Trp Val Lys Gln Ala Pro Gly Lys Gly Leu Lys Trp
         ←CDR-1 atg ggc tgc ata agc act gag act ggt gag tca aca tat gca gat gac
Met Gly Cys Ile Ser Thr Glu Thr Gly Glu Ser Thr Tyr Ala Asp Asp
        CDR-2→ ttc aag gga cgg ttt gcc ttc tct ttg gaa acc tct gcc agc aca gcc
Phe Lys Gly Arg Phe Ala Phe Ser Leu Glu Thr Ser Ala Ser Thr Ala
    ←CDR-2 tat ttg cag atc aac aac ctc aaa gat gag gac acg gct aca tat ttc
Tyr Leu Gln Ile Asn Asn Leu Lys Asp Glu Asp Thr Ala Thr Tyr Phe tgt gct aga agg tac gac gtc gga ggc gat cat tac tac ttt act atg
Cys Ala Arg Arg Tyr Asp Val Gly Gly Asp His Tyr Tyr Phe Thr Met
    CDR-3→ gac tac tgg ggt caa gga acc tca gtc acc gtc tcc tca gcc aaa acg
Asp Tyr Trp Gly Gln Gly Thr Ser Val Thr Val Ser Ser Ala Lys Thr
←CDR-3 aca ccc cca tcg tct ata atc act agt
Thr Pro Pro Ser Ser Ile Ile Thr Ser
```

The $V_L$ region of this mAb2 has the following DNA and encoded peptide sequences. (Nucleotide sequence is SEQ ID NO:61; amino acid sequence is SEQ ID NO:62. The three CDR regions are underscored and labeled.

```
gat tgg gag ctc gac att gtg atc aca cag act aca gtt tct ttg gct
Asp Trp Glu Leu Asp Ile Val Ile Thr Gln Thr Thr Val Ser Leu Ala gtg tct cta ggg cag agg gcc acc atg tcc tgc aga gcc agt gaa agt
Val Ser Leu Gly Gln Arg Ala Thr Met Ser Cys Arg Ala Ser Glu Ser
                                                    CDR-1→ gtt gat agt tat ggc aat agt ttt atg tac tgg ttc cag cag aaa cca
Val Asp Ser Tyr Gly Asn Ser Phe Met Tyr Trp Phe Gln Gln Lys Pro
                         ←CDR-1 gga cag cca ccc aaa ctc ctc atc tat cgt gca tcc aat cta gaa tct
Gly Gln Pro Pro Lys Leu Leu Ile Tyr Arg Ala Ser Asn Leu Glu Ser
                                    CDR-2→ ggg gtc cct gcc agg ttc agt ggc agt ggg tct agg aca gac ttc atc
Gly Val Pro Ala Arg Phe Ser Gly Ser Gly Ser Arg Thr Asp Phe Ile
←CDR-2 ctc acc att gat cct gtg gag gct gat gat gct gct acc tat tac tgt
Leu Thr Ile Asp Pro Val Glu Ala Asp Asp Ala Ala Thr Tyr Tyr Cys
                                                          CDR-3→ cag caa aat aat gag gat ccg tgg acg ttc ggt gga ggc acc aag ctg
Gln Gln Asn Asn Glu Asp Pro Trp Thr Phe Gly Gly Gly Thr Lys Leu
                                    ←CDR3
```

-continued

```
gaa atc aaa cgg gct gat gct gca cca act gta tcc gca tgc acc aat
Glu Ile Lys Arg Ala Asp Ala Ala Pro Thr Val Ser Ala Cys Thr Asn cac
His
```

The V region DNA sequences, or fragments thereof that encode at least one CDR region, are themselves anti-Id immunogens and may be used in accordance with the present invention as DNA vaccines to induce anti-anti-Id antibodies that react against GLXA. These DNA immunogens are administered in formulations, at doses, and by routes that are known in the art for inducing immunity against the peptides/polypeptides encoded by such DNA molecules. Preferably, the DNA immunogens are expression vectors that are expressed in cells and tissues of the recipient, preferably humans. Thus, the DNA immunogens preferably utilize preferred codons for the species in which they are to be expressed, and comprise the requisite promoters, enhancers, etc. for optimal expression.

The initial peptides identified are the sequences of $V_H$ CDR1, 2 and 3 (SEQ ID NO:8, 9 and 10, respectively) and $V_L$ CDR1, 2 and 3 (SEQ ID NO:12, 13 and 14, respectively); see Table 1. These were identified using IMGT/V-QUEST (132). The amino acid sequences were deduced from the coding nucleotide sequences. Of these six, a $V_H$ CDR1 (termed Pep8) and a $V_H$ CDR3 peptide (termed Pep10) were initially selected and synthesized.

Also included within the scope of this invention are $V_L$-peptides of mAb2. Though these peptide sequences are not presented here, they too represent relevant epitopes mimicking GLXA because of the way in which the mAb2 antigen-binding region acts as a molecular mimic of the nominal antigen (here GLXA) (114). mAb1 binds specifically to the mAb2 Ag-combining site (which includes CDR1-3 of both $V_H$ and $V_L$).

TABLE 1

Initial Group of Immunogenic Peptides

| Peptide* | Sequence | SEQ ID NO: | Peptide Category# |
|---|---|---|---|
| Pep1 | SFFTPGLTRAPS | 1 | 1 |
| Pep2 | LTSHNPTTRSYE | 2 | 1 |
| Pep3 | LVSKPYSLTKGI | 3 | 1 |
| Pep4 | AFPQFRSATLLL | 4 | 1 |
| Pep5 | SSPSTNQYSGLS | 5 | 1 |
| Pep6 | SMTESRFHPLSL | 6 | 1 |
| Pep7 | HALMPATAVASL | 7 | 1 |
| Pep8 | GYTFTDYSMH | 8 | 2 (H chain CDR1) |
| Pep9 | CISTETGESTY | 9 | 2 (H chain CDR2) |
| Pep10 | RYDVGGDHYYFTMD | 10 | 2 (H chain CDR3) |
| Pep11 | HTQNMRMYEPWF | 11 | 1 |
| Pep12 | SESVDSYGNSFM | 12 | 2 (L chain CDR1) |

TABLE 1-continued

Initial Group of Immunogenic Peptides

| Peptide* | Sequence | SEQ ID NO: | Peptide Category# |
|---|---|---|---|
| Pep13 | YRASNLESG | 13 | 2 (L chain CDR2) |
| Pep14 | CQQNNEDPWTF | 14 | 2 (L chain CDR3) |

*Initial studies were conducted using Pep4, Pep7, Pep8 and Pep10 (shown in bold)
Anchor residues are underscored (see below)
Peptide categories are discussed and defined above.

This structural relationships among nominal antigens, antibodies to the antigen, anti-Id antibodies and anti-anti-Id antibodies are known in the art and are the basis of the idiotypic network conception first developed by Niels Jerne and enhanced by others thereafter. See, for example, Westen-Schnurr, I., ed., *Idiotypes: Antigens on the Inside: Workshop at the Basel Institute for Immunology*, November 1981, Editiones Roche, Basel, 1982; Kohler, H, (ed) *Idiotypy in Biology and Medicine*, Academic Press, New York, 1984; Shoenfeld, Y et al., (eds) *Idiotypes in Medicine: Autoimmunity, Infection and Cancer*, Elsevier Science; 1$^{st}$ Ed., 1997; Jerne, N K, *Ann. Immunol.* 125C:373-389 (1974); Jerne, N K, *Harvey Lectures* 70:93-110 (1976); Jerne, N K *EMBO J.* 1:243-247, 1982; Jerne, N K, *Immunol Rev* 79:5-24 1984; Bona, C and Hiernaux. J. et al., Immune-Response—Idiotype Anti-Idiotype Network, *CRC Crit. Rev. Immunol.*, 2:33-81 (1981); Schreiber, H., *Adv. Canc. Res.* 41:291-321 (1984);); Augustin A A et al., *Surv Immunol Res.* 1983; 2:78-87 Kohler H et al., *Proc Soc Exp Biol Med.* 1985; 178:189-95; Kieber-Emmons T et al., *Int Rev Immunol.* 1986; 1:1-26; Kennedy, R C et al., *Scientific Amer.* 255:48-56, 1986; Kennedy R C et al., *J Clin Invest.* 1987; 80:1217-24; Ertl H C and Bona C A, *Vaccine.* 1988 April; 6:80-4; Bhattacharya-Chatterjee M and Kohler H, *Adv Exp Med Biol.* 1989; 251:113-27: Raychaudhuri S, et al., *Crit Rev Oncol Hematol.* 1989; 9:109-24; Köhler H et al., *Methods Enzymol.* 1989; 178:3-35; Kieber-Emmons T et al., *Int Rev Immunol.* 1987; 2:339-56; Nisonoff A., *J Immunol.* 1991; 147:2429-38; Bhattacharya-Chatterjee M et al., *Int Rev Immunol.* 1991; 7:289-302; Greenspan N S and Bona C A, Idiotypes: structure and immunogenicity. *FASEB J.* 1993, 7:437-44. Bona C A, *Proc Soc Exp Biol Med.* 1996:213:32-42;

The preferred peptides shown in Table 1 are noted as being Category 1 or Category 2 peptides.

Extensive Blast searches for sequence homology of the Category 1 peptides (recognized by mAb1, mimicking GLXA) with known amino acid sequences have yielded essentially no relevant homologies. These peptides are therefore believed to be novel. Other peptides discovered by this same method and approach are similarly evaluated.

As expected the mAb2-based CDR sequences are homologous, to other IgG H-chain or scFv fragment sequences. However, the present peptides are believed to be unique and novel clearly they induce immune responses specific for *Chlamydia* based on immunostaining by immune sera.

The program PRED$^{BALB/C}$ (133) was employed to test for MHC anchor residues. All the peptides in Table 1 include two deduced anchor residues which would be critical for antigen presentation.

The immunogens of the present invention include mixtures of two or more of the peptides or variants disclosed herein, in the various forms and formulations described.

Amino Acid Substitution Variants

All amino acids listed above are L-amino acids unless it is specifically stated that they are D-amino acids. It should be understood that the present invention includes embodiments wherein one or more of the L-amino acids is replaced with its D isomer.

A preferred variant of the peptide of this invention is one in which a certain number of residues in the peptide sequence, preferably no more that about 4 residues, more preferably no more than 3 residues, more preferably no more than 2 residues, or no more than 1 residue is/are substituted conservatively with a different residue. For a detailed description of protein chemistry and structure, see Schulz, G E et al., *Principles of Protein Structure*, Springer-Verlag, New York, 1979, and Creighton, TE, *Proteins: Structure and Molecular Principles*, W.H. Freeman & Co., San Francisco, 1984, which are hereby incorporated by reference.

Conservative substitutions are those that involve exchanges within one of the following groups:

1. Small aliphatic, nonpolar or slightly polar residues e.g., Ala, Ser, Thr, Gly;
2. Polar, negatively charged residues and their amides: e.g., Asp, Asn, Glu, Gln;
3. Polar, positively charged residues: e.g., H is, Arg, Lys;
4. Large aliphatic, nonpolar residues: Met, Leu, Ile, Val (Cys); and
5. Large aromatic residues: Phe, Tyr, Trp.

Tyr (in Group 5), because of its hydrogen bonding potential, has some kinship with Ser, Thr, etc. (Group 1). Pro, because of its unusual geometry, tightly constrains the chain. Thus, the following substitutions in any one of SEQ ID NO: 1-14 may be present:

| Original | Substitutions |
|---|---|
| Arg (R): | Lys (K) or His (H), |
| Asp (D): | Asn (N), Glu (E), Gln (Q) |
| Leu (L): | Ile (I), Val (V), Met (M), Cys (C) |
| Trp (W): | Phe (F), Tyr (Y) |
| Ala (A): | Gly (G), Ser (S), Thr (T), |

Certain commonly encountered amino acids which also provide useful substitutions include, but are not limited to, β-alanine (β-Ala) and other omega-amino acids such as 3-aminopropionic acid, 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); naphthylalanine (Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,4-diaminobutyric acid (Dbu); 2,4-diaminobutyric acid (Dab); p-aminophenylalanine (Phe(pNH$_2$)); N-methyl valine (MeVal); homocysteine (hCys), homophenylalanine (hPhe) and homoserine (hSer); hydroxyproline (Hyp), homoproline (hPro), N-methylated amino acids (e.g., N-substituted glycine).

Covalent Modifications of Amino Acids and the Peptide

Covalent modifications of the peptide are included and may be introduced by reacting targeted amino acid residues of the peptide with an organic derivatizing agent that is capable of reacting with selected side chains or terminal residues.

Cysteinyl residues most commonly are reacted with α-haloacetates (and corresponding amines) to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate (pH 5.5-7.0) which agent is relatively specific for the histidyl side chain. p-Bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents reverses the charge of the lysinyl residues. Other suitable reagents for derivatizing α-amino-containing residues include imidoesters such as methylpicolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, including phenylglyoxal, 2,3-butanedione, 1,2-cyclohexanedione, and ninhydrin. Such derivatization requires that the reaction be performed in alkaline conditions because of the high $pK_a$ of the guanidine functional group. Furthermore, these reagents may react with the groups of lysine as well as the arginine ε-amino group.

Modification of tyrosyl residues has permits introduction of spectral labels into a peptide. This is accomplished by reaction with aromatic diazonium compounds or tetranitromethane. Most commonly, N-acetylimidizol and tetranitromethane are used to create O-acetyl tyrosyl species and 3-nitro derivatives, respectively.

Carboxyl side groups (aspartyl or glutamyl) are selectively modified by reaction with carbodiimides (R'—N═C═N—R') such as 1-cyclohexyl-3-(2-morpholinyl-(4-ethyl) carbodiimide or 1-ethyl-3-(4-azonia-4,4-dimethylpentyl) carbodiimide.

Aspartyl and glutamyl residues are converted to asparaginyl and glutaminyl residues by reaction with ammonium ions. Conversely, glutaminyl and asparaginyl residues may be deamidated to the corresponding glutamyl and aspartyl residues. Deamidation can be performed under mildly acidic conditions. Either form of these residues falls within the scope of this invention.

Derivatization with bifunctional agents is useful for cross-linking the peptide to a water-insoluble support matrix or other macromolecular carrier. Commonly used cross-linking agents include 1,1-bis(diazoacetyl)-2-phenylethane, glutaraldehyde, N-hydroxysuccinimide esters, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane.

Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other chemical modifications include hydroxylation of proline and lysine, phosphorylation of the hydroxyl groups of seryl or threonyl residues, methylation of the α-amino groups of lysine, arginine, and histidine side chains (Creighton, supra), acetylation of the N-terminal amine, and, in some instances, amidation of the C-terminal carboxyl.

Such chemically modified and derivatized moieties may improve the peptide's solubility, absorption, biological half life, and the like. These changes may eliminate or attenuate undesirable side effects of the proteins in vivo. Moieties capable of mediating such effects are disclosed, for example, in Gennaro, A R, *Remington: The Science and Practice of Pharmacy*, Lippincott Williams & Wilkins Publishers; 21$^{st}$ Ed, 2005 (or latest edition).

Production of Synthetic Peptides Complex

In one embodiment, synthetic peptides are used to formulate the immunogen. Synthetic peptides may be commercially produced by solid phase chemical synthesis. They include cyclic peptides such as those shown in Tables 2 and 3, below.

Two different modes of cyclization can be employed. (a) disulfide bonding between two added terminal Cys residues (or alternatively, if a terminal Cys exists as in Pep9, a single Cys at the opposite terminus may suffice. In Table 2 list below, the added terminal Cys residues are underscored

TABLE 2

Linear Sequences of Cyclic Peptides (C-C bonded*)

| Pep Name | Sequence | SEQ ID NO: |
|---|---|---|
| Pep1/CC | CSFFTPGLTRAPSC | 15 |
| Pep2/CC | CLTSHNPTTRSYEC | 16 |

TABLE 2-continued

Linear Sequences of Cyclic Peptides (C-C bonded*)

| Pep Name | Sequence | SEQ ID NO: |
|---|---|---|
| Pep3/CC | CLVSKPYSLTKGIC | 17 |
| Pep4/CC | CAFPQFRSATLLLC | 18 |
| Pep5/CC | CSSPSTNQYSGLSC | 19 |
| Pep6/CC | CSMTESRFHPLSLC | 20 |
| Pep7/CC | CHALMPATAVASLC | 21 |
| Pep8/CC | CGYTFTDYSMHC | 22 |
| Pep9/CC | CCISTETGESTYC | 23 |
| Pep9/_C | CISTETGESTYC | 24 |
| Pep10/CC | CRYDVGGDHYYFTMDYC | 25 |
| Pep11/CC | CHTQNMRMYEPWFC | 26 |
| Pep12/CC | CSESVDSYGNSFMC | 27 |
| Pep13/CC | CYRASNLESGC | 28 |
| Pep14/_C | CQQNNEDPWTFC | 29 |
| Pep14/CC | CCQQNNEDPWTFC | 30 |

*Cys (C) residues added to original peptide is underscored (b) covalent chemical bonding of side chains of Glu and Lys that would be introduced in place of the terminal Cys residues above, resulting in a peptide bounded by N-terminal Glu and a C-terminal Lys or by an N-terminal Lys and a C-terminal Glu (added terminal K and E residues are underscored in Table 3, below.

TABLE 3

Linear Sequences of Cyclic Peptides (K-E or E-K bonded*)

| Pep Name | Sequence | SEQ ID NO: | Pep Name | Sequence | SEQ ID NO |
|---|---|---|---|---|---|
| Pep1/EK | ESFFTPGLTRAPSK | 31 | Pep1/KE | KSFFTPGLTRAPSE | 45 |
| Pep2/EK | ELTSHNPTTRSYEK | 32 | Pep2/KE | KLTSHNPTTRSYEE | 46 |
| Pep3/EK | ELVSKPYSLTKGIK | 33 | Pep3/KE | KLVSKPYSLTKGICE | 47 |
| Pep4/EK | EAFPQFRSATLLLK | 34 | Pep4/KE | KAFPQFRSATLLLE | 48 |
| Pep5/EK | ESSPSTNQYSGLSK | 35 | Pep5/KE | KSSPSTNQYSGLSE | 49 |
| Pep6/EK | ESMTESRFHPLSLK | 36 | Pep6/KE | KSMTESRFHPLSLE | 50 |
| Pep7/EK | EHALMPATAVASLK | 37 | Pep7/KE | KHALMPATAVASLE | 51 |
| Pep8/EK | EGYTFTDYSMHK | 38 | Pep8/KE | KGYTFTDYSMHE | 52 |
| Pep9/EK | ECISTETGESTYK | 39 | Pep9/KE | KCISTETGESTYE | 53 |
| Pep10/EK | ERYDVGGDHYYFTMDYK | 40 | Pep10/KE | KRYDVGGDHYYFTMDYE | 54 |
| Pep11/EK | EHTQNMRMYEPWFK | 41 | Pep11/KE | KHTQNMRMYEPWFE | 55 |
| Pep12/EK | ESESVDSYGNSFMK | 42 | Pep12/KE | KSESVDSYGNSFME | 56 |

TABLE 3-continued

Linear Sequences of Cyclic Peptides (K-E or E-K bonded*)

| Pep Name | Sequence | SEQ ID NO: | Pep Name | Sequence | SEQ ID: NO |
|---|---|---|---|---|---|
| Pep13/EK | EYRASNLESGK | 43 | Pep13/KE | KYRASNLESGE | 57 |
| Pep14/EK | ECQQNNEDPWTFK | 44 | Pep14/KE | KCQQNNEDPWTFE | 58 |

*Glu (E)) or Lys (K) residues added to original peptide is underscored

Cyclization via flanking Glu and Lys residue side chains has an added advantage in that an N- or C-terminal Cys can be introduced to serve as a thiol donor for cross linking via a maleimide moiety.

The synthetic peptides can be made as monomers or conjugated to any appropriate "carrier" molecule that enhances, or permits the manifestation of the immunogenicity of the peptide (see below).

In one embodiment, the synthetic peptides can be conjugated to a branched poly-Lys or Lys dendrimer (4, 8 and 16 residues).

Synthetic peptides are preferably purified at least to 80% purity, for example, by HPLC.

The peptides are examined for their ability to (a) bind efficiently to mAb1 (anti-chlamydial GLXA), and/or (b) induce an antibody response characterized in its specificity to GLXA or to the non-modified peptides (e.g., any of Pep1-Pep11). Again, this can be done most efficiently by ELISA, although the antibody produced in (b) can be tested for binding to *Chlamydia* -infected cells or for biological activity such as *Chlamydia* neutralization or induction of specific responses to the organism such as cytokine release by T and/or B cells obtained from peptide-immunized mice or other mammals.

The peptides may also be displayed on phage using known methods. For the phage-displayed peptides, the phage serves as a "scaffold" that is studded along its length with peptide-. This presentation is extremely efficient for immunogenic activity. Alternatively, synthetic peptides are efficiently expressed as N-terminal maltose binding protein (MBP) fusions, The affinity of a given peptide for Ab1 (or antigen) may be sufficient for a conjugate to be administered as an immunogen without the need for additional cross linking Although crosslinking can denature proteins, crosslinkers are nonetheless used to stabilize immunogens or to inactivate pathogens that are used in vaccines. Therefore, use of crosslinkers is not incompatible with the present immunogens. Crosslinked immunogens are evaluated by testing the binding of the crosslinked complexes with a panel of defining mAb using routine methods.

Multimeric Peptides and Fusion Proteins (Polyproteins)

The present invention also includes longer peptides or polypeptides in which a sequence of the present immunogenic GLXA-mimicking peptide or substitution or addition variant thereof, or a chemical derivative thereof, is repeated from two to about 100 times, with or without intervening spacers or linkers. Such molecules are termed in the art, interchangeably, multimers, concatemers or multiepitope polyproteins and will be referred to herein primarily as peptide multimers. When produced recombinantly, they are also considered to be fusion polypeptides or fusion proteins.

A multimer of the peptide referred to symbolically in this section as "P" is shown by the following formula $(P\text{-}X_m)_n\text{-}P$, wherein m=0 or 1, n=1-100. X is a spacer group, consisting, for example, of 1-20 Gly residues, other known spacers/linkers including cleavable linkers (see below) or chemical cross-linking agents. Thus, when m=0, no spacer is added to the peptide. When n=1, the multimer is a dimer, etc.

These multimers may be built from any of the present immunogenic peptides or variants described herein. Moreover, a peptide multimer may comprise different combinations of peptide monomers (either from the native sequence or variants thereof). Thus a multimer may include several sequential repeats of a first peptide, followed by one or more repeats of a second peptide, etc. Such multimeric peptides can be made by chemical synthesis of individual peptides, recombinant DNA techniques or a combination, e.g., chemical linkage of recombinantly produced multimers.

When produced by chemical synthesis, the multimers preferably have from 2-12 repeats, more preferably 2-8 repeats of the core peptide sequence, and the total number of amino acids in the multimer should not exceed about 110 residues (or their equivalents, when including linkers or spacers).

A preferred synthetic chemical peptide multimer has the formula $P^1_n$ wherein $P^1$ is an immunogenic peptide of the invention (or a substitution or addition variant of such a peptide), and n=2-8, and wherein the peptide alone or in multimeric form has the desired immunologic reactivity.

In another embodiment, a preferred synthetic chemical peptide multimer has the formula $(P^1\text{-}X_m)_n\text{-}P^2$, wherein $P^1$ and $P^2$ are the immunogenic peptides or addition variants of these peptides, and wherein (a) $P^1$ and $P^2$ may be the same or different; moreover, each occurrence of $P^1$ in the multimer may be a different peptide (or variant) from its adjacent neighbor;

(b) X is $C_1$-$C_5$ alkyl, $C_1$-$C_5$ alkenyl, $C_1$-$C_5$ alkynyl, $C_1$-$C_5$ polyether containing up to 4 oxygen atoms, wherein m=0 or 1 and n=1-7; X may also be Gly, wherein, z=1-6, and wherein the peptide alone or in multimeric form has the immunological activity of reacting with anti-GLXA antibodies (Ab1), preferably the mAb produced by HB11300.

When produced recombinantly, spacers are $Gly_z$ as described above, where z=1-6, and the multimers may have as many repeats of the core peptide sequence as the expression system permits, for example from two to about 100 repeats. A preferred recombinantly produced peptide multimer has the formula: $P^1\text{-}Gly_z)_n\text{-}P^2$, wherein:

(a) $P^1$ and $P^2$ are immunogenic, GLXA-mimicking peptide as described herein or substitution or addition variants of these peptides, wherein $P^1$ and $P^2$ may be the same or different; moreover, each occurrence of $P^1$ in the multimer may be different peptide (or variant) from its adjacent neighbor.

wherein n=1-100 and z=0-6; and (b) wherein the peptide alone or in multimeric form has the desired immunologic reactivity.

In the foregoing peptide multimers, $P^1$ and $P^2$ is preferably selected from any one of Pep1-Pep14 (i.e., SEQ ID NO:1 through SEQ ID NO:14). The multimer is optionally capped at its N- and C-termini, It is understood that such multimers may be built from any of the peptides or variants described herein. Although it is preferred that the additional variant monomeric units of the multimer have the biological activity described above, this is not necessary as long as the multimer of which they are part has the activity.

The present invention includes as fusion polypeptide which may comprise a linear multimer of two or more repeats of the above peptide monomers linked end to end, directly or with a linker sequences present between the monomer repeats and further fused to another polypeptide sequence which permits or enhances the activity of the present immunogenic peptides in accordance with this invention. Common examples are conjugates of the peptide with an immunogenic polypeptide, particularly one the induces potent T helper cell activity. Many of these are well-known in the art.

The present multimers and fusion polypeptides may therefore include more than one GLXA-like epitope, and the immunogenic composition may include mixtures of such multimers or fusion proteins, each comprising one or more peptides of the invention.

Also included in the invention are "tandem" oligomeric peptides that comprises two or three repeats of the above peptide that are linked in tandem ("side-by-side").

Peptides and multimers may be further chemically conjugated to form more complex multimers and larger aggregates. Preferred conjugated multimers include Cys and are made by forming disulfide bonds between the —SH groups of these residues, resulting in branched chains as well as straight chain peptides or polypeptides.

In addition to, or as an alternative to the spacers/linkers described above, the present multimers and fusion polypeptides may include linkers that are cleavable by an enzyme, preferably by a matrix metalloproteal se, urokinase, a cathepsin, plasmin or thrombin. Non-limiting examples of these are peptide linkers of the sequence VPRGSD (SEQ ID NO:63) or DDKDWH (SEQ ID NO:64). Any cleavable or non-cleavable linker known in the art may be used, provided that it does not interfere with the immunogenic capability of the peptides in the multimer.

The present peptides may be combined in any of the forms of multimers and fusion polypeptides described above or otherwise known in the art that comprise one or more repeats of a single peptide or mixtures of such peptides fused to other proteins, e.g., carrier molecules or other proteins which would enhance their immunogenicity when used as immunogenic or vaccine compositions.

Adjuvants, Immune Stimulants and Peptide Immunogen Formulations

The immunogenicity of the present peptide immunogen is enhanced in the presence of exogenous adjuvants, immune stimulants, depot materials, etc. Thus in addition to the peptide or peptide conjugate described herein, the present immunogenic composition preferably includes one or more adjuvants or immunostimulating agents. It is well-known in the art that much of what is described below in connection with peptide immunogens is also applicable with DNA immunogens, such as DNA encoding relevant parts of mAb2 V regions chains, domains, or shorter sequences thereof—another embodiment of the present invention.

Examples of adjuvants or agents that may add to the effectiveness of the peptide as an immunogen include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, whole organisms or subcellular fractions of the bacteria *Propionobacterium acnes* or *Bordetella pertussis*, polyribonucleotides, sodium alginate, lanolin, lysolecithin, vitamin A, saponin and saponin derivatives (such as QS21®), liposomes, levamisole, DEAE-dextran, blocked copolymers or other synthetic adjuvants, or CpG oligonucleotides. Another adjuvant is ISAF-1 (5% squalene, 2.5% pluronic L121, 0.2% Tween 80 in phosphate-buffered solution with 0.4 mg of threonyl-muramyl dipeptide (Kwak, L W et al., 1992, *N. Engl. J. Med.*, 327: 1209-1238). Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.), Amphigen® (oil-in-water), Alhydrogel® (aluminum hydroxide), or a mixture of Amphigen® and Alhydrogel®. Aluminum is approved for human use. The vaccine material may be adsorbed to or conjugated to beads such as latex or gold beads, ISCOMs, and the like. General methods to prepare vaccines are described in Gennaro, *Remington's Pharmaceutical Sciences*, supra).

The adjuvant is preferably one or more of (a) Ribi adjuvant; (b) ISAF-1 (5% squalene, 2.5% pluronic L121, 0.2% Tween 80) in phosphate-buffered solution with 0.4 mg of threonyl-muramyl dipeptide; (c) Amphigen®; (d) Alhydrogel; (e) a mixture of Amphigen® and Alhydrogel®; (f) QS21®; or (g) monophosphoryl lipid A adjuvant. A preferred adjuvant is monophosphoryl lipid A.

Liposomes are pharmaceutical compositions in which the active peptide or protein is contained either dispersed or variously present in corpuscles consisting of aqueous concentric layers adherent to lipidic layers. The active peptide is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Adjuvants, including liposomes, are discussed in the following references, incorporated herein by reference: Gregoriades, G. et al., *Immunological Adjuvants and Vaccines*, Plenum Press, New York, 1989; Michalek, S. M. et al., 1989, *Curr. Top. Microbiol. Immunol.* 146:51-8.

Additional discussion of vaccine design, particularly controlled release systems, can be found in Powell, M. F. et al. (eds), *Vaccine Design: The Subunit and Adjuvant Approach*, Powell, M. F. et al. (eds), Plenum Press, New York, 1995, p 389-412. Controlled release systems are already used in humans as "depots" to deliver drugs and hormones (Langer, R., 1990, *Science* 249: 1527-1533). Such systems may have a significant impact on immunization as they can be designed to deliver controlled amounts of the immunogen continuously or in spaced pulses at predetermined rates (Cohen et al., 1991, *Pharm. Res.* 8:713-720; Eldridge et al., 1991a, *Mol. Immunol.* 28:287-294; Gander et al. 1993, in: *Proc. Int'l Symp. Control. Rel. Bioact. Mater.*, Controlled Release Society, Washington, D.C., pp. 65-66), while simultaneously protecting undelivered antigenic material from rapid degradation in vivo.

Microspheres, including controlled release microspheres have considerable potential for oral immunization (Edelman et al., 1993, *Vaccine* 11:155-158; Eldridge et al., 1990, *J. Control. Rel.* 11:205-214; McQueen et al., 1993, *Vaccine* 11:201-206; Moldoveanu et al., 1989, *Curr Top. Microbiol.*

Immunol. 146:91-99; O'Hagan et al., 1993b, Vaccine 11: 149-154; Reid et al. 1993, Vaccine 11:159-167 Panyam J and Labhasetwar V (2003) Adv Drug Deliv Rev 55:329-47; and Panyam J and Labhasetwar V (2004) Mol Pharm. 1:77-84, 2004). Other potential advantages of polymeric controlled release systems include: lower dosage requirements leading to decreased cost; localized or targeted delivery of antigen to antigen-presenting cells or the lymphatic system; more than one antigen may be encapsulated, facilitating the design of a formulation that can immunize an individual against more than one peptide or against several epitopes in a single injection; and improved patient compliance. In addition, controlled release systems may reduce the number of immunogen doses required for optimal vaccination to a single injection.

Microspheres are particularly suited as controlled release immunogen carriers for two reasons: (1) particles greater than 10 µm in diameter are capable of providing a long-term persistence of antigen at the site of injection which may be necessary for a sustained high-level antibody immune response and (2) microparticles in the size range of 1-10 µm are readily phagocytosed by macrophages (Eldridge et al., 1989, Adv. Exp. Med. Biol. 251:192202; Tabata et al., 1988, Biomaterials 9:356-362; J. Biomed Mater Res. 22:837-858) leading to direct intracellular delivery of antigen to antigen-presenting cells.

Microsphere phagocytosis by macrophages may be increased by altering the surface characteristics, as microspheres with hydrophobic surfaces are generally more readily phagocytosed than those with hydrophilic surfaces (Tabata et al., 1988, Biomaterials 9:356-362; Tabata et al., 1990, Crit. Rev. Ther Drug Carrier Syst. 7:121-148).

Among the advantages of using polymer microspheres for immunogen delivery is the ability to control the time following administration at which the antigen is released. This capability allows the fabrication of a single-injection formulation that releases multiple "pulses" of the immunogen or immunogen at predetermined times following administration (Gilley et al., 1992, In: Proc. Int'l. Symp. Control. Rel. Bioact. Mater, Controlled Release Society, Orlando, pp. 110-111). Antigen release kinetics from polymer microspheres can be controlled to a great extent by the simple manipulation of such variables as polymer composition and molecular weight, the weight ratio of immunogen to polymer (i.e., the immunogen loading), and microsphere size (Hanes et al., In: Reproductive Immunology, 1995, R. Bronson et al., eds, Blackwell. Oxford).

Formulations that contain a combination of both smaller (1-10 µm) and larger (20-50 µm) microspheres may produce higher and longer-lasting responses compared to the administration of immunogen encapsulated in microspheres with diameters exclusively in one range or the other. (Eldridge et al., 1991a, Mol. Immunol. 28:287-294; and Keegan et al. (42). In one study, tetanus toxoid (TT)-containing microspheres were tailored to produce a strong priming antigen dose released over the first few days after injection followed by two "boosting" doses released after 1 and 3 months, respectively, in order to mimic conventional vaccination schedules (Gander et al., supra).

Microencapsulation of the mAb2 (product of hybridoma HB11301) described above, and therefore, by extension, of the present peptides, is particularly useful for achieving oral or mucosal immunization. One advantage of such a formulation observed by the present inventors was the induction of dendritic cell (DC) maturation. Thus, pulsing of immature bone marrow-derived mononuclear cells with this preparation influenced their mature DC phenotype. After cells were incubated with GM-CSF for 5-7 days, they were pulsed with either 1.2 or 12 µg/ml of mAb2 in microspheres for 24 hrs. Cells were stained for DC marker CD11c and mature DC marker CD86. The percent of double-positive DCs increased with microsphere pulsing compared to unpulsed cells or cells stimulated with LPS. UV-inactivated chlamydial EB had a similar effect on DC maturation markers and is consistent with the understanding that a particulate antigen has this effect on DC's.

The most widely used polymers for vaccine microencapsulation have been the polyesters based on lactic and glycolic acid. These polymers have several advantages, including extensive data on their in vitro and in vivo degradation rates (Lewis, 1990, In: Biodegradable Polymers as Drug Delivery Systems (Chasin and Langer, eds.), Dekker, New York, pp. 1-41; Tice and Tabibi, 1992, In: Treatise on Controlled Drug Delivery (A. Kydonieus, ed.), Dekker, New York, pp. 315-39, and FDA approval for a number of clinical applications in humans such as surgical sutures (Gilding et al., 1979, Polymer 20:1459-1464; Schneider, 1972, U.S. Pat. No. 3,636,956) and a 30-day microsphere-based controlled delivery system for leuprolide acetate (Lupron Depot) (Okada et al., 1991, Pharm. Res. 8:787-791; Keegan et al., supra; Panyam et al., supra).

Several alternatives to the lactide/glycolide polyesters include biodegradable polymers that degrade to give molecules with adjuvant properties, and may prove particularly useful as carriers of more weakly immunogenic antigens. Because of the know adjuvanticity of L-tyrosine derivatives (Wheeler et al, 1982, Int. Arch. Allergy Appl. Immunol. 69:113-119; Wheeler et al., 1984, Int. Arch. Allergy Appl. Immunol. 75:294-299), a polymer based on a dityrosine derivative was synthesized by Langer and colleagues (Kohn et al., 1986, Biomaterials 7:176-82) and studied using as a model antigen bovine serum albumin, BSA (Kohn et al., 1986, J. Immunol. Methods 95:31-38). Biodegradable poly (CTTH iminocarbonate) was selected since its primary degradation product N-benzyloxycarbonyl-L-tyrosyl-L-tyrosine hexyl ester (CTTH), was found to be as potent an adjuvant as complete Freund's (CFA) and muramyl dipeptide (MDP).

Because of its inherent propensity to be phagocytosed by macrophages (Tabata et al., 1986, J. Bioact. Compat. Polym. 1:32-46) and its extensive use in pharmaceutical and medical applications, gelatin is a useful polymer for vaccine microencapsulation (Tabata et al., 1993, in: Proc. Int. Symp. Control. Rel. Bioact. Mater, Controlled Release Society, Washington, D.C., pp. 392-393). Gelatin microspheres have also been used to encapsulate immunostimulators, such as MDP and interferon-α (Tabata et al., 1987, J Pharm Pharmacol. 39:698-704; 1989, Pharm. Res. 6:422-7). Microsphere-encapsulated MDP activates macrophages in much shorter periods than free MDP at concentrations approximately 2000 times lower. A combination of MDP and vaccine-containing gelatin microspheres may yield a very potent vaccine formulation.

Liposomes are often unstable in vivo, most likely because of their rapid destruction by macrophages and high-density lipoproteins (Schreier et al., 1987, J. Control. Rel. 5:187-92), and therefore provide only a brief antigen depot effect when injected subcutaneously or intramuscularly (Eppstein et al., 1985, Proc Natl Acad Sci USA 82:3688-92; Weiner et al., 1985, J. Pharm. Sci. 74:922-5). One approach to extending the in vivo lifetime of liposomes (Cohen et al., 1991, Proc Natl Acad Sci USA 88:10440-44) is use of alginate polymers to encapsulate immunogen-containing liposomes into microspheres, thereby protecting them from rapid destruction in vivo. Alginate NP were shown by one of the present inventors to readily enter infected cells and is another formulation intended herein. Enzymatically activated microencapsulated liposomes (MELs) that are capable of providing pulsatile immunogen release kinetics have also been prepared (Kibat et al., 1990, *FASEB J.* 4:2533-39). MELs are also expected to show increased stability as a carrier for oral/mucosal administration.

A variety of methods may be used to prepare immunogen-loaded polymer microspheres that are capable of a wide range of release patterns and durations. The method of choice usually is determined by the relative compatibility of the process conditions with the antigen (e.g., the method that results in the least loss of immunogenicity) and the polymer excipient used, combined with the ability of the method to produce appropriately sized microspheres.

Solvent evaporation techniques are popular because of their relative ease of preparation, amenability to scale-up, and because high encapsulation efficiencies can be attained. Of particular importance for immunogens that are sensitive to organic solvents may be the multiple emulsion technique (Cohen et al., 1991, *Pharm. Res.*, supra). Spray drying and film casing techniques have also been used to prepare monolithic polymer microspheres.

The present inventors and colleagues have shown that PLGA NP can be encapsulated in chitosan core shell particles. If peptides were loaded into either the NP or the CS particle, pulmonary delivery to immunize via the lungs could be used.

Microcapsules consist of an immunogen-loaded core surrounded by a thin polymer membrane and, as a result, are often referred to as "reservoir" systems.

Carrier and immunogen stability during device development, storage, and in vivo depoting are a matter for concern. Polypeptide antigens may have fragile three-dimensional structures that are vital to immunogenicity. This 3D structure may be compromised or lost if the antigen is one that tends to denature or aggregate. Exposure to organic solvents, rehydration after lyophilization on exposure to moisture, or complex chemical interactions with the polymer excipient or other chemicals in the preparation of a controlled release device may result in loss or reduction of immunogenicity of peptide/protein-based vaccines. The following documents describe stabilization of complex antigens (Arakawa et al., 1993, *Adv. Drug Deliv. Rev.* 10: 1-28; Liu et al., 1991, *Biotechnol. Bioeng.* 37:177-184; Volin and Klibanov, 1989, In: *Protein Function: A Practical Approach* (T. E. Creighton, ed.). IRL Press, Oxford, pp. 1-24).

One preferred approach to the preparation of peptide-loaded polylactide (PLA) or PLGA micro- and/or nanoparticles follows. Biodegradable PLA or PLGA nanoparticles (NPs) loaded with the selected peptides is prepared using a modified version of the double emulsion solvent evaporation technique, in a procedure similar to that previously described by Li and co-workers (139). This approach has been demonstrated to be gentle enough to maintain the biological activity of peptides, and result in high loading efficiency. Briefly, an aqueous solution of the peptide is emulsified in dichloromethane containing the PLGA (using an ultrasonic homogenizer), thus forming the primary water-in-oil (w/o) emulsion. The prepared w/o emulsion is then emulsified in a second aqueous phase containing polyvinyl alcohol (PVA) as stabilizer, thus resulting in the multiple w/o/w emulsion. The double emulsion is later added into a large volume of aqueous solution of PVA, and stirred for several hours to evaporate the organic solvent. The resulting nanoparticles are then collected by centrifugation and washed (removing PVA) several times before lyophilization to remove the remaining water (139,140). The powder is kept at −80° C. until use. The concentration of peptide and polymer are varied so as to achieve a peptide concentration of 1-10 μg/mg polymer for oral delivery of approximately 10 μg peptide/ml per mouse. NPs are filter-sterilized before administration to mice or addition to cultured cells. Every effort to avoid contamination is desirable because endotoxin severely attenuates chlamydial viability. Optimal peptide loading concentrations for protective immunization are determined empirically, e.g., by comparing orally delivered peptide-NP to free peptide delivered subcutaneously. Parameters to which attention should be paid are those affecting the morphology (size and size distribution), loading efficiency and release profiles including the type of solvent and stabilizer, energy input and w/o ratio will be investigated in initial experiments (134, 135). NP in the 50-200 nm diameter are believed to be most effective for mucosal uptake (136, 137)).

Before immunization, each new preparation of peptide-NP is preferably tested for conserved immunogenicity by SC immunizations of 4-5 mice. Blood is collected before each immunization/boost for testing by ELISA. Known positive and negative control sera are included in the relevant ELISA.

An advantage of polymer microsphere formulations is that many polymers are stable at room temperature for extended periods of time if kept dry. For example, lactide/glycolide polyesters have been reported to be stable if kept dry and below about 40° C. (Aguado et al., 1992, *Immunobiology* 184:113-25). In addition, vaccine can be stored in the dry state within microsphere formulations, an important advantage considering susceptibility of some proteins to moisture-induced aggregation (Liu et al., supra).

The compositions preferably contain (1) an effective amount of the immunogen or immunogenic complex together with (2) a suitable amount of a carrier molecule or, optionally a carrier vehicle, and, if desired, (3) preservatives, buffers, and the like. Descriptions of formulations are found in Voller, A. et al., *New Trends and Developments in Vaccines*, University Park Press, Baltimore, Md., 1978).

In one embodiment, the immunogenic composition includes one or more cytokines such as IL-2, GM-CSF, IL-4 and the like. Proinflammatory chemokines may be added, e.g., interferon inducible protein 10 and MCP-3 (Biragyn A et al., 1999, *Nature Biotechnol.* 17:253-8). In general, it appears that any cytokine or chemokine that induces or promotes inflammatory responses, recruits antigen presenting cells (APC) and promotes targeting of APC for chemokine receptor-mediated uptake of the polypeptide antigen is useful in the present formulation.

As with all immunogenic compositions for eliciting immunity, the immunogenically effective amounts of the polypeptide complex of the invention must be determined empirically. Factors to be considered include the immunogenicity of the present peptides is whether or there will occur further complexing with, or covalent bonding to, an adjuvant or carrier protein or other carrier and the route of administration and the number of immunizing doses to be administered. Such factors are known in the vaccine art, and it is well within the skill of immunologists to make such determinations without undue experimentation.

The proportion of the peptide immunogen and adjuvant can be varied over a broad range so long as both are present in effective amounts. For example, aluminum hydroxide can be present in an amount of about 0.5% of the mixture ($Al_2O_3$ basis).

After formulation, the composition may be incorporated into a sterile container which is sealed and stored at low temperatures., for example 4° C. or −20° C. or −80° C. Alternatively, the material may be lyophilized which permits longer-term storage in a stabilized form.

The pharmaceutical preparations are made following conventional techniques of pharmaceutical chemistry. The pharmaceutical compositions may also contain minor amounts of nontoxic auxiliary substances such as wetting or emulsifying agents, pH buffering agents and so forth. The peptides/complexes are formulated using conventional pharmaceutically acceptable parenteral vehicles for administration by injection. These vehicles are nontoxic and therapeutic, and a number of formulations are set forth in Gennaro (*Remington's Pharmaceutical Sciences*, supra). Nonlimiting examples of excipients are water, saline, Ringer's solution, dextrose solution and Hank's balanced salt solution. Formulations according to the invention may also contain minor amounts of additives such as substances that maintain isotonicity, physiological pH, and stability. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension. Optionally, a suspension may contain stabilizers.

The peptides and other useful compositions of the invention are preferably formulated in purified form substantially free of aggregates and other protein materials, preferably at concentrations of about 1.0 ng/ml to 100 mg/ml.

Virus, Bacteriophage or Bacteria as Immunogenic Carriers

In a further variation, the immunogenic peptide or conjugate of the present invention, can be presented by a virus or a bacterium as part of an immunogenic composition. A nucleic acid encoding the immunogenic peptide is incorporated into a genome or episome of the virus or bacteria. Optionally, the nucleic acid is incorporated in such a manner that the immunogenic peptide is expressed as a secreted protein or as a fusion protein with an outer surface protein of a virus or a transmembrane protein of a bacterium so that the peptide is displayed. Viruses or bacteria used in such methods should be nonpathogenic or attenuated. Suitable viruses include adenovirus, HSV, Venezuelan equine encephalitis virus and other alpha viruses, vesicular stomatitis virus and other rhabdoviruses, vaccinia and fowl pox. Suitable bacteria include *Salmonella* and *Shigella*.

The display of short peptides such as those that comprise immunogenic epitopes fused to a phage surface also serve as a useful immunogen. Filamentous bacteriophages are excellent vehicles for the expression and presentation of foreign peptides in a variety of biological systems (Willis, E A et al., 1993, *Gene* 128:79-83; Meola, A. et al., 1995, *J. Immunol.* 154: 3162-72: Bastein, N et al., 1997, *Virology* 234:118-22). Administration of filamentous phages induces a strong immune response to the phage proteins in all animals tested, without any evidence of toxic effects. Phage proteins pIII and pVIII are proteins that have been often used for phage display. Furthermore, recombinant filamentous phage are used to produce a source of specific peptides, e.g., for use as antigens. An important advantage of this approach over chemical synthesis is the fact that the products obtained are the result of the biological fidelity of translational machinery and are not subject to the 70-94% purity levels common in the solid-phase synthesis of peptides. The phage presents an easily renewable source of the peptide, as additional material can be produced by growth of bacterial cultures. Genetically engineered filamentous phages thus serve as a means of obtaining both the peptide and an immunogenic carrier for antibody production without necessitating the use of an adjuvant. See, also, Frenkel, D et al., 2000, *Proc Natl Acad Sci USA* 97:11455-59).

Immunization with phage displayed peptides typically requires $10^{10}$ to $10^{12}$ phage particles per injection. A method such as that described by Yip, Y L et al., 2001, *Immunol Lett* 79:197-202) may be used. This method employs $10^{12}$ phages/ 100 µl for ip immunization of mice; similar phage doses are appropriate for immunization of rabbits.

Production of phages in *E. coli* cells routinely generates $10^{13}$ phages per 0.5-1.0 liters of culture medium. Production of adequate amounts of phage displayed m2-peptide for the intended pilot study is therefore straightforward. $gp120_{BaL}$ is commercially available, and gp120 or gp160 expression vectors and vaccinia expression vectors of BaL strain molecule are readily available.

Peptides can be displayed on filamentous phages on either the pIII protein (five copies per phage) or, on the pVIII protein (2700 copies per phage) (Yip et al., supra). The fth1 expression system displays peptides on pVIII protein in chimeric phages where recombinant pVIII proteins are incorporated in a majority of wild-type pVIII proteins, thereby generating a mosaic phage.

Preparations of a peptide or peptide conjugate exemplified here by the Pep1-Pep11, more specifically, by Pep4, 7, 8 and/or 10, are tested against (a) Ab1 (anti-GLXA antibody, or (b) one or more anti-anti-Id (Ab3 antibodies generated by immunization mAb2, or (c) *Chlamydia* organisms in culture.

If desired a variety of cross linkers can be screened to ensure that a compatible cross-linker is found that preserves the structure/antigenicity of a conjugated, cross-linked peptide immunogen without hindering its immunogenicity in vivo. For this, the peptide conjugate preparation is prepared in a Tris buffer, a phosphate buffer, or any other standard, compatible buffer, and reacted with various homobifunctional and heterobifunctional cross linking agents overnight on ice. The various peptides of the invention include various numbers of Asp or Arg residues with potential functional R groups for cross linking The abundance of free carboxyl groups should allows the use of carbodiimide-based cross linkers. Also Arg residues lend themselves cross-linkers such as p-azidophenyl glyoxal monohydrate (APG; Pierce Biotechnology Inc).

Other examples of useful bacteriophage vectors are Fuse 5 and f88, as well as phage-peptide libraries based on peptides of, for example 8-20 amino acids.

A library sample containing $10^9$ phage particles is subjected to three rounds of biopanning and amplification. See, for example, Frenkel, D et al., 1999, *J. Neuroimmunol.* 95:136-42. The selected phages are tested for their ability to bind to an anti-phage antibody by ELISA assays. Wells of microplates are coated with appropriate dilutions of a secondary antibody preparation, for example, rabbit anti-phage anti serum, and incubated overnight at 4° C. Positive phage clones are propagated, and their DNA is sequenced in the insert region.

Recombinant phage displaying the peptide of choice as fusion of protein VIII, are selected and produced in large quantities for immunization. For example a 2-ml overnight culture of a colony of an appropriate *E. coli* strain or mutant is grown at 37° C. in 2YT medium, for example, containing tetracycline. An aliquot of this preculture is used to subculture 1 liter of 2YT/tet containing 2 mM isopropyl-D-thiogalactoside. After 16 h of incubation at 37° C., the culture is centrifuged at 7,500×g for 30 min, and the supernatant with infectious phages is precipitated at 4° C. for 2 h by the addition of 0.15 volume of a solution containing polyethylene glycol-8000 and concentrated NaCl. After centrifugation, the phage pellet is resuspended in PBS and centrifuged again for bacteria contamination release; the supernatant is re-precipitated and resuspended in PBS and the phage concentration is estimated spectrophotometrically (1 OD unit at 269 nm represents $10^{11}$ phage/ml).

A phage preparation is preferably inactivated by UV before use in immunization. See, for example, Galfre, G et al., 1997, *Vaccine* 15:1276-85.

Dendritic Polymers/Dendrimers.

This embodiment is based on the knowledge in the art that a multiple antigen peptide carrying a multiplicity of epitopes induces superior immune responses compared to responses following immunization with corresponding equal amounts of monovalent epitopes The present invention is intended to broadly encompass antigenic products carrying multiple copies of the peptides of the present invention an in a multiple antigen peptide system.

The present dendritic polymers are antigenic product according to the present based on dendritic polymer in which an antigens/epitope or epitopes are covalently bound to the branches that radiate from a core molecule. These dendritic polymers are characterized by higher concentrations of functional groups per unit of molecular volume than ordinary polymers. Generally, they are based upon two or more identical branches originating from a core molecule having at least two functional groups. Such polymers have been described by Denkewalter et al. (U.S. Pat. No. 4,289,872)) and Tomalia et al. (U.S. Pats. Nos. 4,599,400 and 4,507,466). Other polymers of this class were described by Erickson in U.S. Pat. No. 4,515,920. See, also, Solomon, US Patent Publication 2005/0053575.

The polymers are often referred to as dendritic polymers because their structure may be symbolized as a tree with a core trunk and several branches. Unlike a tree, however, the branches in dendritic polymers are substantially identical.

This dendrite system has been termed the "multiple antigen peptide system" (MAPS), which is the commonly used name for a combination antigen/antigen carrier that is composed of two or more, usually identical, antigenic molecules covalently attached to a dendritic core which is composed of principal units which are at least bifunctional/difunctional. Each bifunctional unit in a branch provides a base for added growth.

The dendritic core of a multiple antigen peptide system can be composed of lysine molecules. For example, a lysine is attached via peptide bonds through each of its amino groups to two additional lysines. This second generation molecule has four free amino groups each of which can be covalently linked to an additional lysine to form a third generation molecule with eight free amino groups. A peptide may be attached to each of these free groups to form an octavalent multiple peptide antigen (MAP). The process can be repeated to form fourth or even higher generations of molecules. With each generation, the number of free amino groups increases geometrically and can be represented by $2^n$, where n is the number of the generation. Alternatively, the second generation molecule having four free amino groups can be used to form a tetravalent MAP with four peptides covalently linked to the core. Many other molecules, including, e.g., the amino acids Asp and Glu, both of which have two carboxyl groups and one amino group to produce poly-Asp or poly-Glu with $2_n$ free carboxyl groups, can be used to form the dendritic core of MAPS.

The term "dendritic polymer" or "dendrimer" is sometimes used herein to define a product of the invention. The term includes carrier molecules which are sufficiently large to be regarded as polymers as well as those which may contain as few as three monomers.

The chemistry for synthesizing dendritic polymers is known and available. With amino acids the chemistry for blocking functional groups which should not react and then removing the blocking groups when it is desired that the functional groups should react has been described in detail in numerous patents and scientific publications. The dendritic polymers and the entire MAP can be produced on a resin as in Merrifield synthesis and then removed from the polymer. Tomalia (supra) utilized ammonia or ethylenediamine as the core molecule. In this procedure, the core molecule is reacted with an acrylate ester by Michael addition and the ester groups removed by hydrolysis. The resulting first generation molecules contain three free carboxyl groups in the case of ammonia and four free carboxyl groups when ethylenediamine is employed. Tomalia and colleagues (see below) extended the dendritic polymer with ethylenediamine followed by another acrylic ester monomer, an repeats the sequence until the desired molecular weight was attained. It is readily apparent to one skilled in the art, that each branch of the dendritic polymer can be lengthened by any of a number of selected procedures. For example, each branch can be extended by multiple reactions with Lys molecules.

Erickson (supra) utilized the classic Merrifield technique in which a polypeptide of substantially any desired molecular weight is grown from a solid resin support. As the technique is utilized for the preparation of dendritic polymers, the linking molecule which joins the polymer to the resin support is trifunctional. One of the functional groups is involved in the linkage to the resin, the other two functional groups serve as the starting point for the growth of the polymer. The polymer is removed from the resin when the desired molecular weight has been obtained. One standard cleavage procedure is treatment with liquid hydrogen fluoride at 0° C. for one hour. Another, and more satisfactory procedure, is to utilize a complex of hydrogen fluoride and dimethylsulfide (HF:DMF) as described (Tam et al., 1983, *J Amer Chem Soc* 105:6442) to minimize side reactions and loss of peptide.

In one example, Denkewalter et al. (supra) utilized Lys as the core molecule. The amino groups of the core molecule are blocked by conversion to urethane groups. The carboxyl group is blocked by reaction with benzhydrylamine. Hydrolysis of the urethane groups generates a benzhydrylamide of lysine with two free amino groups which serve as the starting points for the growth of the dendritic polymer.

This brief discussion of three of the available procedures for producing dendritic polymers should be adequate those skilled in the art to depart from these general teachings and teaches the skilled artisan the salient features of the polymers, such as the provision of a large number of available functional groups in a small molecular volume. The result is that a high concentration of epitopes in a small volume can be attained by joining the epitopes/antigen to those available functional groups. The resulting product contains a high proportion of the epitopes on a relatively small carrier, (the antigen:carrier ratio is quite high). This contrasts with other, conventional products used for formulating vaccines which typically comprise a small amount of antigen on a large amount of carrier.

Other important features of the dendritic polymer as an immunogenic carrier are that the precise structure is known; there are no "antigenic" contaminants or those that irritate tissue or provoke other undesirable reactions. The precise concentration of the peptide known; and is symmetrically distributed on the carrier; and the carrier can be utilized as a base for more than one peptide or complex so that multivalent immunogens or vaccines can be produced. See, for example, Parag-Kolhe, P et al., 2006, *Biomaterials* 27:660-9.

When the MAPS is to be employed to produce a vaccine or immunogenic composition, it is preferred that the core molecule of the dendrimer be a naturally occurring amino acid such as Lys so that it can be properly metabolized. However, non-natural amino acids, even if not α-amino acids, can be employed. The amino acids used in building the core molecule can be in either the D or L-form.

More details about the chemistry and pharmaceutical use of dendritic polymers can be found in Tomalia D A et al., 2007, *Biochem Soc Trans*. 35:61-7; Braun C S et al., 2005, *J Pharm Sci*. 94:423-36; Svenson S et al., 2005, *Adv Drug Deliv Rev*. 57:2106-29 and U.S. Pat. Nos. 4,289,872; 4,558,120; 4,376,861; 4,568,737; 4,507,466; 4,587,329; 4,515,920; 4,599,400; 4,517,122; and 4,600,535.

A resin-bound dendritic polymer can be employed in the practice of this invention. Such preparations may be obtained commercially from a number of suppliers (e.g., Advanced Chem Tech, Inc. Louisville, Ky.). The polymer may be cleaved from the resin using HF:DMS as a preferred agent. The dendritic poly-Lys built from a Gly linker originally joined through a benzyl linker to the resin. Other linkers such as Ala can be employed or the linker may be omitted, or linker molecules can be utilized.

Additional Sources of Peptide or Immunogens mAb2 may be expressed in *Nicotiana* plants, e.g., *Nicotiana benthamiana*, primarily in the leaves but also in any plant part, e.g., a root shoot, a flower or a plant cell (see, for example, U.S. Pat. No. 7,084,256). Similarly, the present peptides may be fused to viral particles, or viral coat proteins for use as immunogens or their production in plants. For description of producing peptide fusions in plants, for example, as viral coat protein fusions that are useful in vaccine applications. See, for example, U.S. Pat. Nos. 7,033,835, 6,660,500, and 5,977,438; Smith M L et al., 2006, *Virology* 348:475-88. Vaccine uses are described in U.S. Pat. No. 7,084,256; McCormick A A et al., 1999, *Proc Natl Acad Sci USA*, 96:703-8 and McCormick A A et al., 2008, *Proc Natl Acad Sci USA* 105:10131-6. A plant-produced immunogen comprising the present peptides can be formulated by encapsulation in VLP or microspheres as describe above. For additional discussion of plant vaccines, see Thanavala Y et al., 2006, *Expert Rev Vaccines* 5:249-60.

Doses and Routes of Immunization

A preferred effective dose for treating a subject in need of the present treatment, preferably a human, is an amount of up to about 100 milligrams of active compound per kilogram of body weight. A typical single dosage of the peptide or peptide conjugate or complex is between about 1 μg and about 100 mg/kg body weight, and preferably from about 10 μg to about 50 mg/kg body weight. A total daily dosage in the range of about 0.1 milligrams to about 7 grams is preferred for intramuscular (I.M.) or SC administration.

The foregoing ranges are, however, suggestive, as the number of variables in an individual treatment regime is large, and considerable excursions from these preferred values are expected. As is evident to those skilled in the art, the dosage of an immunogenic composition may be higher than the dosage of the compound used to treat infection (i.e., limit viral spread). Not only the effective dose but also the effective frequency of administration is determined by the intended use, and can be established by those of skill without undue experimentation. The total dose required for each treatment may be administered by multiple doses or in a single dose. The peptide complex may be administered alone or in conjunction with other therapeutics directed to the treatment of the disease or condition.

Pharmaceutically acceptable acid addition salts of certain compounds of the invention containing a basic group are formed where appropriate with strong or moderately strong, non-toxic, organic or inorganic acids by methods known to the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts. Pharmaceutically acceptable base addition salts of compounds of the invention containing an acidic group are prepared by known methods from organic and inorganic bases and include, for example, nontoxic alkali metal and alkaline earth bases, such as calcium, sodium, potassium and ammonium hydroxide; and nontoxic organic bases such as triethylamine, butylamine, piperazine, and tri(hydroxymethyl)methylamine.

The compounds of the invention, as well as the pharmaceutically acceptable salts thereof, may be incorporated into convenient dosage forms, such as capsules, impregnated wafers, tablets or preferably injectable preparations. Solid or liquid pharmaceutically acceptable carriers may be employed.

The present invention is useful to protect against or treat chlamydial infections of the eye, genital tract, lung or heart. Other anatomic sites/tissue which would be protected include synovial tissues of any joint, the central nervous system, the gastrointestinal tract, etc. Chlamydial infection primarily on mucosal surfaces: conjunctival, genital, respiratory, and neonatal occurring primarily on mucosal surfaces.

Preferably, the compounds of the invention are administered systemically, e.g., by injection or infusion. Administration may be by any known route, preferably intravenous, subcutaneous, intramuscular or intraperitoneal. Other acceptable routes include intranasal, intradermal, intrathecal (into an organ sheath), etc. Most preferred routes for the present invention are oral and/or topically to mucosal sites, to achieve local, mucosal protection of the mouth, pharynx and alimentary canal, eyes/conjunctiva, or the genital tract, and lung, and, indirectly, the heart, central nervous system, synovial tissues.

Mouse Models of *C. trachomatis* Infection

The present inventors have used two mouse models in which they demonstrated the efficacy of vaccination using the earlier mAb2 vaccine ((26,27)). See also U.S. Pat. Nos. 5,656, 271 and 5,840,297). These references are all incorporated by reference in their entirety.

Mice are challenged with a human biovar of *C trachomatis* (K or E serovars for urogenital infections; C or B serovars for ocular infection).

Groups of 4-8 mice are "masked" as to pretreatment before challenge with live elementary bodies (EB). At weekly intervals through at least 4 wks, vaginal (or conjunctival) swabs are collected for isolation culture and direct fluorescence antibody staining for EB.

For example, *C. trachomatis* serovar C (TW-3) elementary bodies 5000 IFU/20 μl are inoculated onto each eye of the recipient mouse which has been immunized with an immunogen according to the present invention or a control immunogen (e.g., unrelated or scrambled peptide).

While clinical disease was most evident with repeated infection (daily, repeated weekly or once weekly), even a single inoculation of infectious *Chlamydia* induced eyelid thickening and exudate formation. Histopathologically, intensity of inflammatory mononuclear infiltrate, loss of goblet cells, and appearance of exudate were dose-dependent. The mean histopathologic disease score at day 12-14 was 6.8.+−.0.8 compared to 0+0 for normal tissue.

On the day before the inoculation and on day 7, 10, 14, 21, 28 and 35 thereafter, both conjunctiva are swabbed. The area included the inferior tarsus and formix, the lateral formix, the superior tarsus and formix, and the medial formix. The conjunctival swabs are immediately immersed in collection medium and disrupted for two minutes by vortex and kept on ice until culture.

Figure 17:
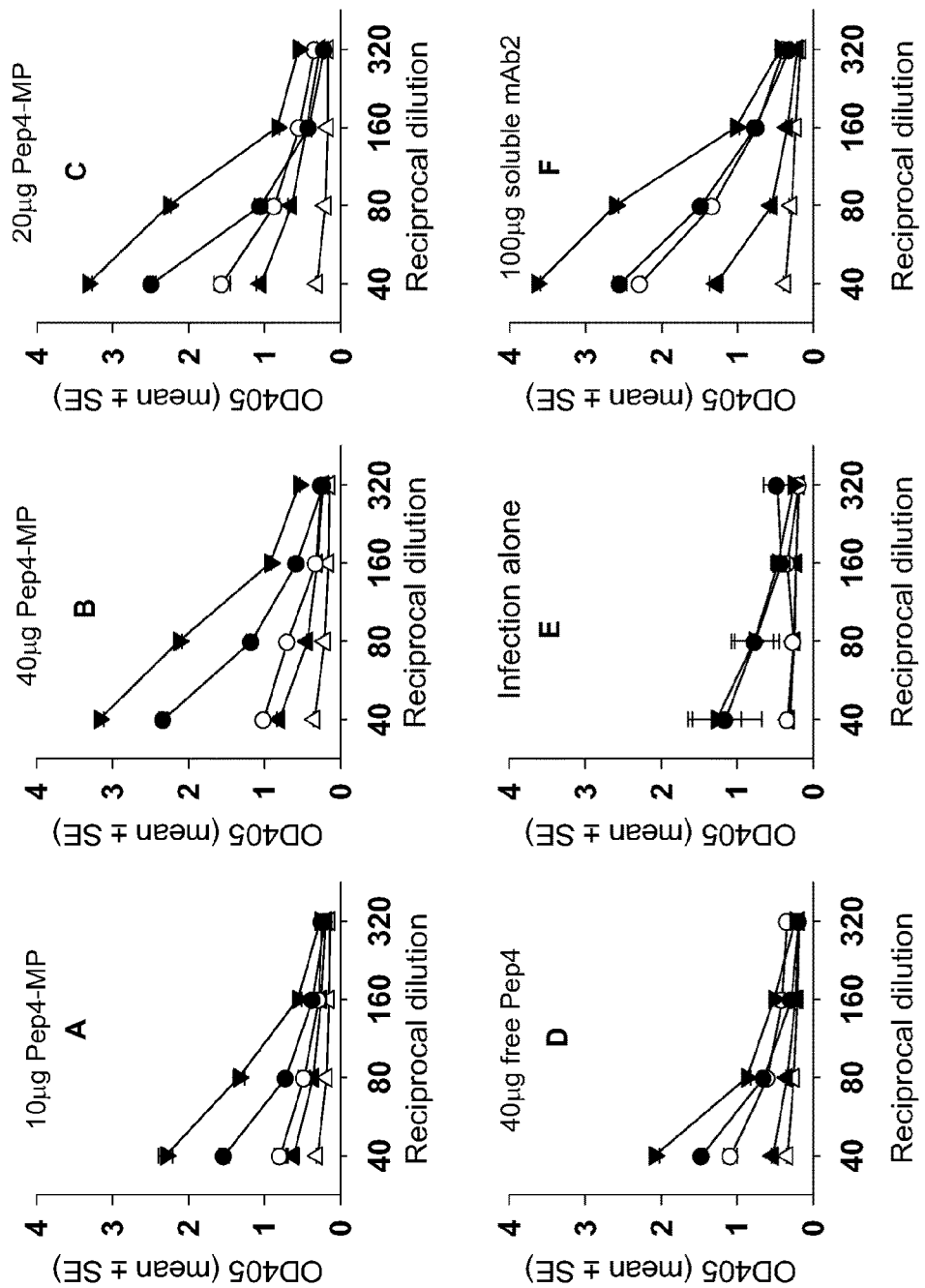

A typical microbiologic time course obtained with conjunctival swabs from 10 BALB/c mice is shown in FIG. 17 of U.S. Pat. No. 5,656,271 (supra).

Example V below provides results of immunizations with the present peptides in these models.

As indicated above, genital infections with *Chlamydia* predispose to development of a significant proportion of reactive arthritis cases; viable, metabolically active organisms are present in these patients' synovium. The immunogenic compositions of the present invention (peptide, polypeptide or DNA) may be used in a method for preventing or treating arthritis in subjects in need thereof, when the arthritis is associated with or caused by *chlamydia*.

Having now generally described the invention, the same will be more readily understood through reference to the following examples which are provided by way of illustration, and are not intended to be limiting of the present invention, unless specified.

EXAMPLE I

Peptides of Both Categories that Mimic GLXA are Immunogenic in Mice

Mice were immunized with Pep4, 7, 8, and 10 (100 pg/dose) delivered subcutaneously (SC) in complete Freund's adjuvant (CFA), then given two boosts in incomplete Freund's adjuvant (IFA). An additional group of mice received the combination of Pep4 and Pep7 as these were suspected of being the stronger immunogens of the group. A positive control group received soluble mAb2 in adjuvant. A negative control group received the diluent (phosphate buffered saline/PBS in adjuvant. This method also serves as an initial positive control for alternative formulations of peptide immunogens, e.g., in nanoparticles.

Blood was collected prior to immunizations and prior to the two boosts. Sera were tested in ELISA. The ELISA method used in the present examples, in which many if not all the parameters and conditions may be varied or modified in ways that are completely conventional in the art, is described below.
1. 96 well plates (Immulon HBX4) were coated with 50 µl of diluted antigen (peptides at 1 µg/well made in carbonate buffer) and incubated overnight at 4° C.
2. Unbound antigen was removed by flicking the contents of the plate into a sink without further washing.
3. Non-specific binding was blocked or prevented by adding 300 µL/well of 4% BSA/PBS-Tween 20 (0.05%). This was allowed to incubate for 2 hour at room temperature.
4. The plates were washed once with PBS-Tween 20 (0.05%) and 50 µl of primary antibody was added per well at appropriate dilutions. When using serum, the starting dilution was 1:40 and was further diluted by doublings to 1:80, 1:160, and 1:320 (or higher as desired). Plates were incubated for 1 hour at 37° C.
5. Plates were washed three times with PBS-Tween (0.05%) as above and 100 µl of secondary antibody was added per well at appropriate dilutions. For alkaline phosphatase-conjugated goat anti-mouse IgG-AP, a dilution of 1:500 was used here. Plates were incubated for 1 hour at 37° C.
6. Plates were again washed three times as above and 200 µl of substrate solution for Alkaline phosphatase (p-nitro phenyl phosphate or pNPP) was added at a concentration of 5 mg/ml. The color reaction was read in an automated microplate reader at a frequency of 405 mm and the absorbance (or optical density) was registered (referred to as $A_{405}$ or $OD_{405}$)

Figure 3:
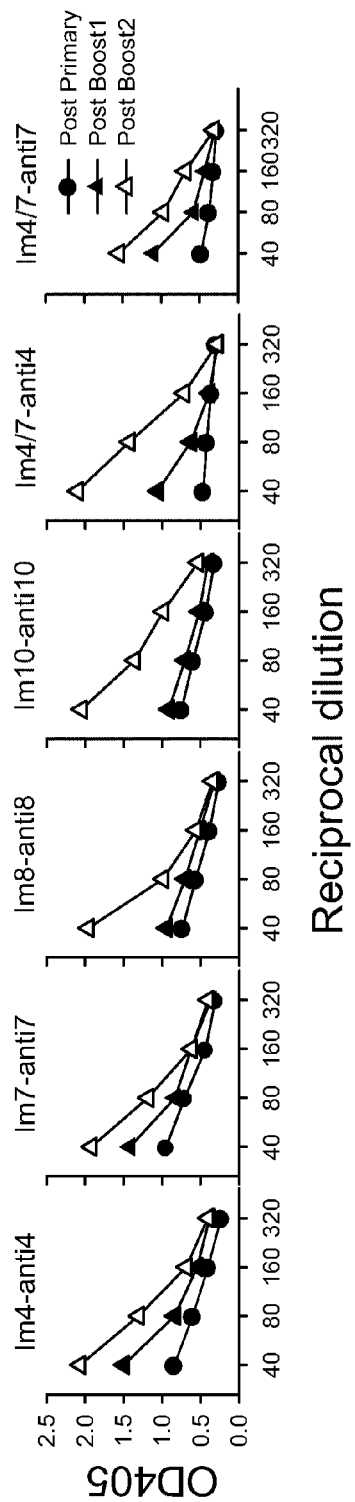

Several important observations were made in these tests against the 4 peptides: (a) all 4 peptides were immunogenic and induced increasing anti-peptide responses with subsequent boosts in all mice (except in one non-responder) (FIG. 3). It is seen that each group of mice exhibited increasing antibody responses to the respective immunizing peptides, (n) is indicated for each group. See also FIG. 16A-16B

Figure 4:
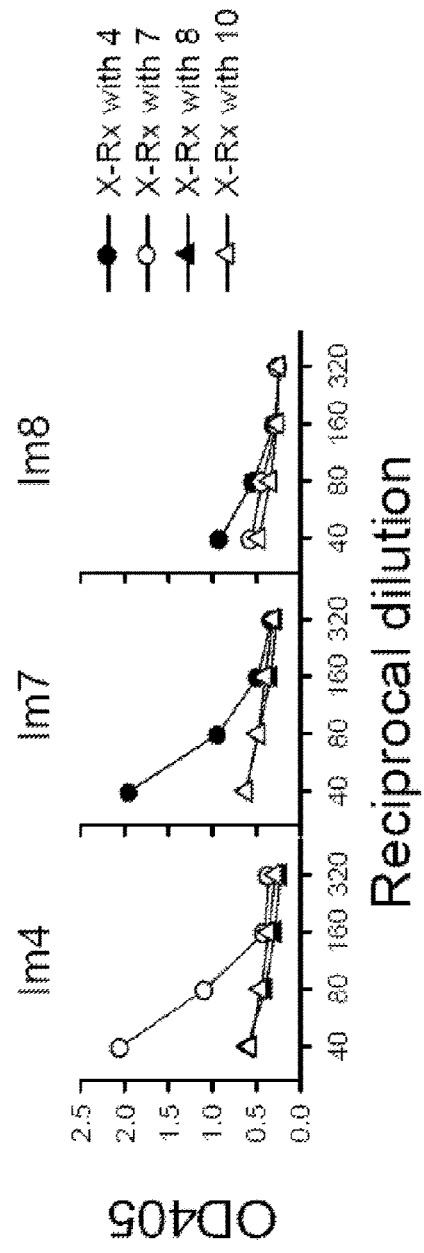
Figure 5:
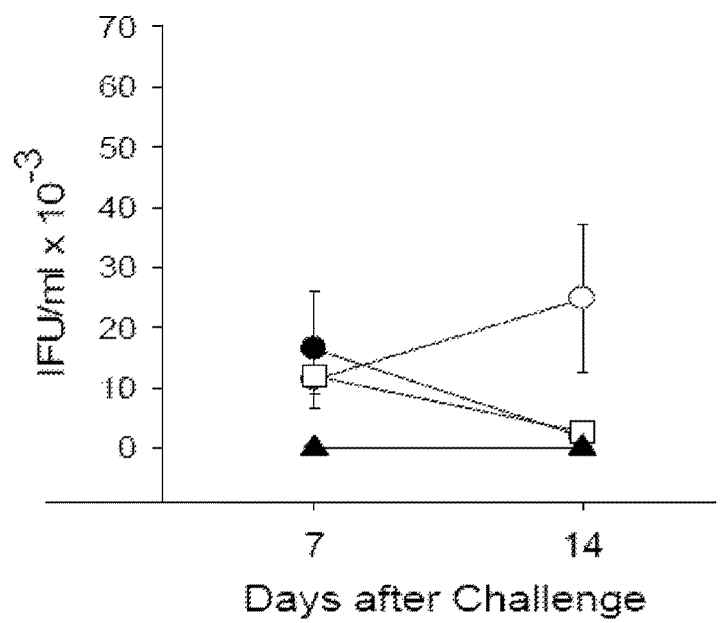
Figure 6:
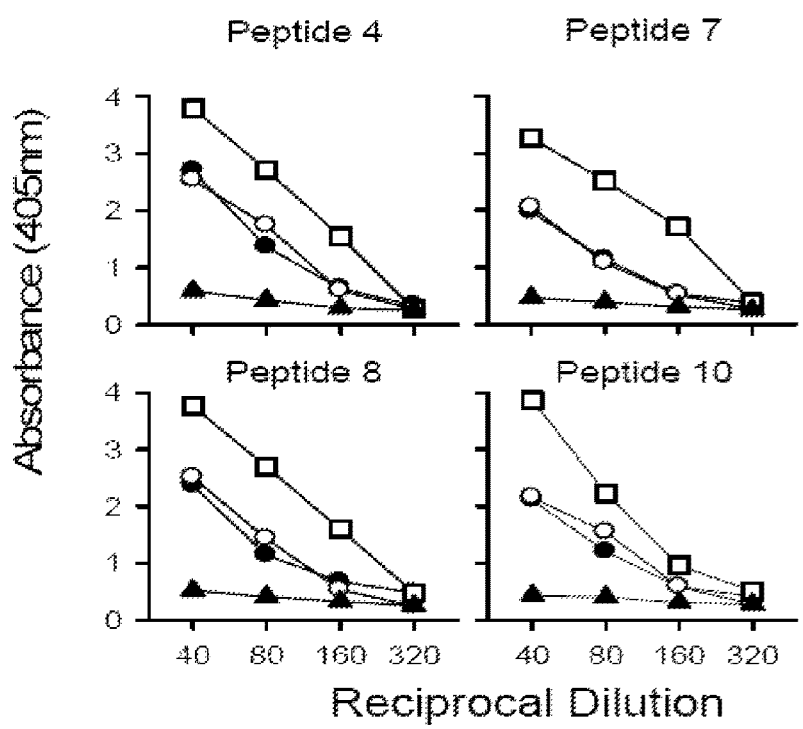
Figure 7:
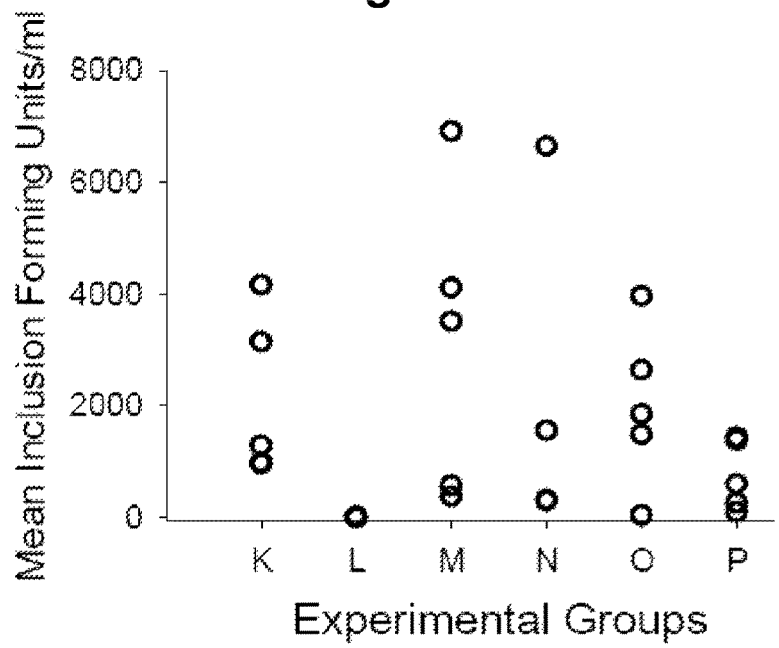
Figure 8:
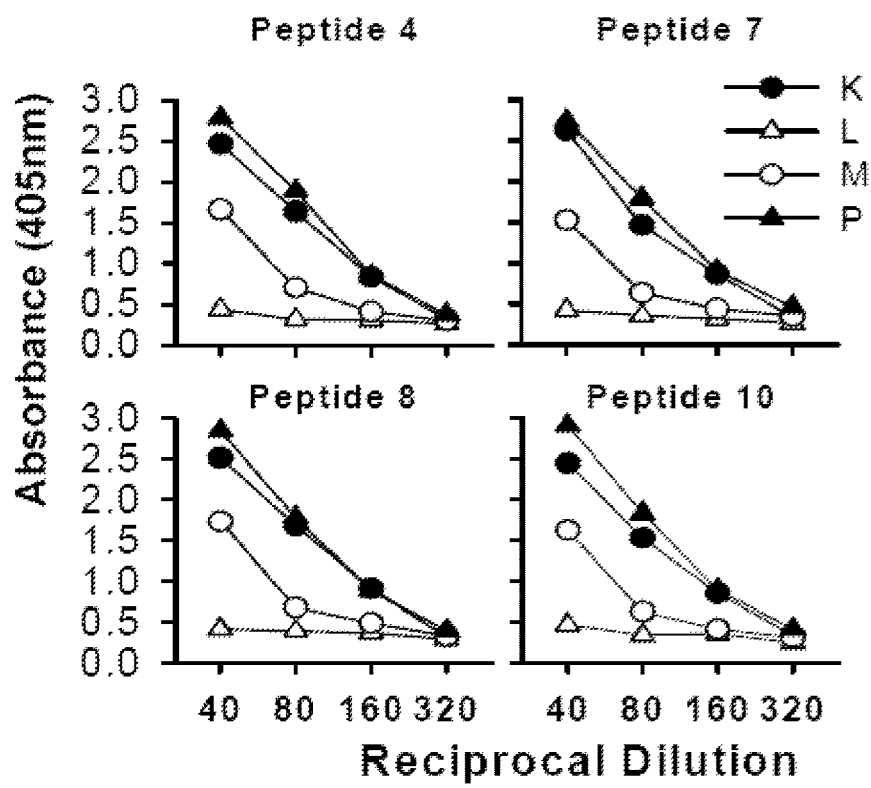

FIG. 4 shows cross-reactivity patterns between peptides. Each of the three panels shows the Ab responses against all four peptides in subjects immunized with a single peptide (Pep 4, 7 or 8) Abs raised against Pep4 cross reacted with Pep7 and vice versa. Both of these are category #1 peptides. Abs raised against Pep8 did not cross-react with either of Peps 4, 7 or 10. That supports the notion that CDR1 and CDR3 of mAb2 are antigenically distinct.

EXAMPLE II

Protective Effects of Immunization with Peptide Immunogens

In one experiment, immuno-incompetent SCID mice received adoptive transfer of spleen cells from syngeneic mAb2-immunized donor mice and were challenged with the K serovar (strain) of *C. trachomatis* 2000 TCID50 (~$10^7$ IFU/30 µl topically vaginally; mice were pretreated with Depo-Provera at 7 and 3 days before challenge to enhance infectivity by human biovars. Results are shown in FIG. 5. Immunodeficient mice which received mAb2-immune lymphocytes were significantly protected from the infectious challenge, manifest as reduced shedding of the bacteria).

Sera from the cell donor mice (which were immunized directly with the earlier vaccine candidate (mAb2 in microspheres)) were tested for reactivity with the peptide immunogens of the present invention in ELISA (as above). These results are shown in FIG. 6, panels B-E).

The animals immunized with whole mAb2 showed dramatic reactivity against the peptides, and this correlated with demonstrated protection and anti-GLXA responses. Also shown in the figs is the reactivity of anti-mAb2 sera with *C trachomatis* infected cells.

It should be noted that infection alone of mice receiving control, non-immune spleen cells also induced a measurable antibody responses to the peptides. This confirms an important point: epitopes against which Abs developed (induced by whole mAb2 and present in the indicated peptides of this invention) are present on the intact, infecting organism.

Sera from these groups of mice were tested by ELISA for reactivity against the four peptide immunogens (Pep4, 7, 8 and 10 (FIG. 6). Recipients of unfractionated immune spleen cells that included T cells (+T) developed the strongest antibody responses. Recipients of T cell depleted (−T) spleen cells (from which T cells were removed by treatment with anti-T cell antibodies such as anti-Thy-1 and complement) had anti-peptide responses similar to recipients of normal cells. As expected, the latter group, which was infected, developed Ab to the peptides since chlamydial organism bear these epitopes.

EXAMPLE III

Immunogenic Peptides Serve Protective Form of Chlamydial Antigenic Epitopes that can be Administered as Nanoparticles Studies were done to confirm the feasibility of oral/mucosal delivery of the present immunogens in nanoparticles by testing sera from animals immunized with the whole mAb2 formulation for their reactivity against four of the present peptides. Mice were immunized with microencapsulated mAb2 three times at 2-3 wk intervals (see table below) and challenged intravaginally with *C trachomatis* E serovar (2000 TCID50/30 μl). Vaginal swabs were collected for isolation culture or direct fluorescent antibody (DFA) staining of vaginal smears at weekly intervals. At the termination of the experiment, blood and tissues were collected. Serum from these terminal bleeds were tested in the peptide ELISA.

Results are shown in FIGS. 7 and 8. FIG. 7 shows the shedding (detected by in vitro culture) of bacteria from immunized animals.

Mice were directly immunized with mAb2-microspheres by the subcutaneous (SC) or oral (PO) routes or in combinations using the following regimens (Table 4; as labeled in the Figure). Despite variability in shedding at day 14 post-challenge, oral-only delivery of the earlier mAb2 vaccine (Group P) had the strongest effect in reducing vaginal shedding of organism (FIG. 7).

Sera from subjects immunized exclusively via the SC route (Group K) or the oral route (Group P) were compared to non-immunized subjects which were infected (Group M) and non-immunized, uninfected controls (Group L) for Abs against the four peptides (n=4-5/grp).

TABLE 4

| Group (n = 5) | Immunization | Infection (E serovar) |
|---|---|---|
| K | SC × 3 | Yes |
| L | None | No |
| M | None | Yes |
| N | PO, SC × 2 | Yes |
| O | SC, PO × 2 | Yes |
| P | PO × 3 | Yes |

The ELISA results in FIG. 8 show that infection alone induced anti-peptide antibody responses (group M, -○-). SC and oral delivery of the microencapsulated-mAb2 both induced anti-peptide Ab responses. Uninfected controls were negative. Pre-immunization sera tested at the same dilutions were all negative, and, indeed, the absorbance values of those samples were subtracted from the values of Groups K-P in any given experiment.

These observations were significant since the mice were never exposed to the peptide immunogens per se, and moreover, were challenged with different chlamydial serovars (K serovar in the case of FIG. 5 discussed above, and E serovar in the study shown in FIGS. 7 and 8.

EXAMPLE IV

Peptide-Induced *Chlamydia*-Specific Antibody Responses that Recognize Elementary Bodies (EB) In Situ Sera obtained after the second boost and prior to exposure to whole organism (from the study described in Example III), and which were positive against the peptides in ELISA, were found to recognize *C trachomatis*-infected cells. This was shown using indirect immunofluorescence. Pre-bleeds from the same mice were totally negative by immunostaining (not shown).

We have deduced novel peptides which represent two or more epitopes/homologs of a genus-specific chlamydial antigen. These have no apparent homology to human or vertebrate proteins, nor to chlamydial proteins/antigens.

HEp2 cells were infected with *C. trachomatis* were subjected to cytocentrifugation to deposit them onto microscope slides. After fixation (MeOH) they were stained with sera (1:40 dilution) from mice immunized with the indicated peptides or with soluble mAb2. The binding of the antibodies to the cells was detected using a fluorescent (FITC-labeled) secondary Ab, an anti-mouse IgG. Results appear in FIGS. 9A-F.

Pre-bleeds from the same mice were completely negative (not shown). Arrows point to distinct differences in targets of the immune sera.

Sera from subjects immunized with Pep4, Pep7 or both (A-C, respectively), both of which are category #1 peptides, recognized EB and metabolically active, non-infectious reticulate bodies (RB).

Sera from subjects immunized with Pep8 and 10 (FIGS. 9D and 9E), category 2 peptides corresponding to sequences in CDR1 and CDR2 of mAb2 also recognized targets in the inclusion matrix and membrane similar to mAb2-immune sera (F). Specificity of these antisera seemed to vary when comparing phage derived mAb1 peptides and mAb2 CDR regions of Pep 8 and Pep 10 based on the structures targeted for the two groups of peptides (Pep 4, Pep 7 derived from mAb1; Pep 8 and Pep 10 represent CDR1 and CDR3 of the mAb2 heavy chain, respectively).

EXAMPLE V

Reduced Microbial Load in Mice Immunized with Peptides

Using the murine models described above, the present inventors immunized mice with one of the four peptides (Pep4, 7, 8 or 10) administered three times at 100 μg doses. Results of direct fluorescent antibody (DFA) staining are summarized for days 7 and 14 post-challenge in FIGS. 10-11.

The results indicate that immunization with of Pep4, Pep4+Pep7, or Pep8 reduced bacterial shedding measured by DFA staining. Immunization with Pep4 also reduced DFA scores, although immunization with peptide 7 alone did not. In contrast, the combination of the two peptides (Pep4 & Pep7) reduced DFA scores markedly.

Although the DFA test detects the bacteria, it does not provide information about their viability. However, it is generally accepted that reduced shedding correlates with reduced culture positivity.

These results show that the mixture of Pep4 and Pep7 represent together a protective antigenic epitope that is recognized by mAb1. It is fully expected that other combinations of two or more of the immunogenic peptides described herein will demonstrate enhanced immunogenicity and protection compared to individual peptides.

Based on the inventors' and their colleagues' prior results showing more effective protective immunity with oral delivery of encapsulated whole mAb2 vaccine, the present invention provides oral/mucosal administration of the present peptides, alone or in combination, encapsulated in microparticles or nanoparticles to achieve enhanced protective immunity.

EXAMPLE VI

Analysis of Peptide Immunogen Encapsulated in PLGA

Pep4 was encapsulated in PLGA nanoparticles (NPs) using the modified version of the double emulsion solvent evaporation technique described above (by Li and co-workers (139)).

Figure 12:
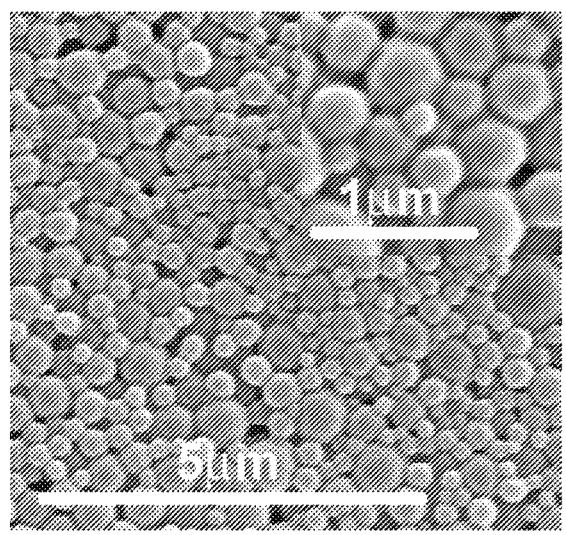
Figure 13A:
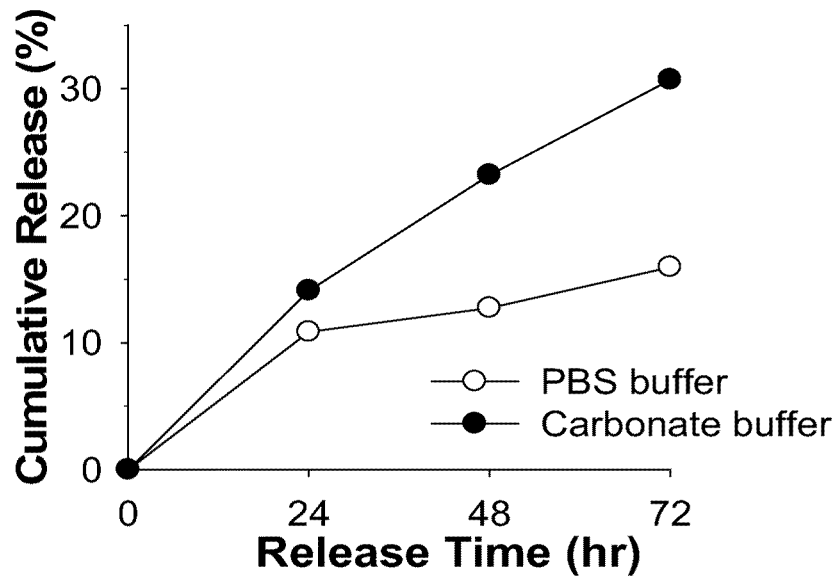

Encapsulation efficiency was found to be 38.8%, with a final concentration of 7.8 µg peptide per mg PLGA. FIG. 12 shows an example of the morphology of the NPs. FIGS. 13A and B show peptide release profiles of 5 mg NP. FIG. 13A shows the release determined by reverse phase (RP)HPLC of NP's in PBS and carbonate buffer. The rate of release was about 3 µg/ml/day). (See also Example X, below, especially FIG. 19A-B for release from PLA).

Figure 13B:
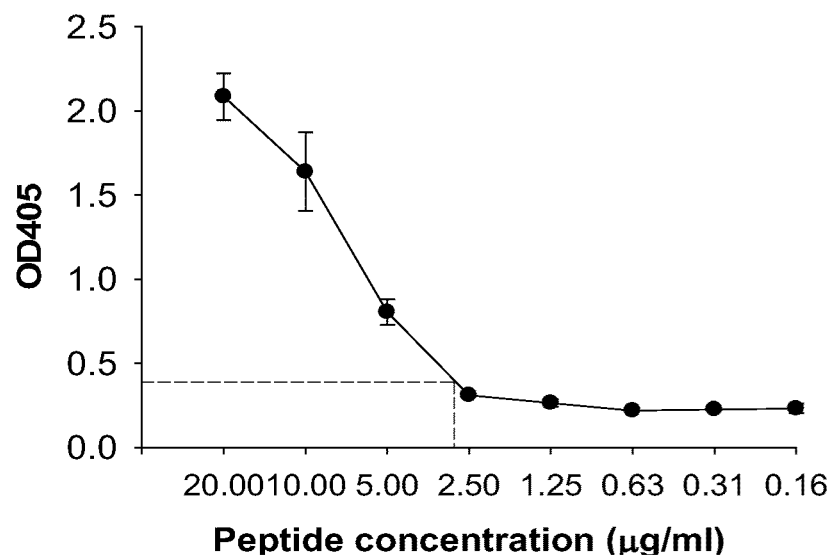

The samples in the carbonate buffer where also examined immunochemically in an ELISA. Results in FIG. 13B showed a release of about 3.8 µg/ml/day based on the standard curve with Pep4 and anti-Pep4 antiserum, in line with the HPLC results These results demonstrate encapsulation of significant amounts of the active immunogenic peptide within the NPs and the capacity for controlled release of the peptide which maintains an intact (non-denatured) state as recognized by specific antibodies. Encapsulation efficiency, release profile and particle morphology can be modified and improved by varying the preparation parameters, according to known methods.

EXAMPLE VII

Anti-Peptide Antisera React with Cells Persistently Infected with C trachomatis

Sera which were shown above to stain acutely infected cells in vitro were tested for reactivity with persistently infected cells (as induced by Penicillin G (PenG)). Activity was examined in 4-well chamber slides in samples in which PenG was added at $t_0$ (1 hr after addition of inoculum) or 18 hrs later ($t_{18}$). Cells were fixed 48 hr post-infection. Each serum sample was tested at $t_0$ and $t_{18}$ on PenG-treated cells and on control cells not treated with PenG on the slides.

Sera from all treatment groups immunized with Pep4, Pep7, Pep4+Pep7, Pep8 or Pep10 were tested in 3 separate experiments. Results for Pep4, Pep7 and: Pep4+Pep7 on infected McCoy cells (heterodiploid mouse fibroblasts; 148) are shown in FIG. 14A-F. FIGS. 14A-C show cells at $t_0$. and FIGS. 14D-F show parallel treatment groups at $t_{18}$. Insets in FIGS. 14D-F show representative "control" infected cells (no PenG) from the same experiment. Similar results to those described here were obtained with human epithelial cells (HEp20. Note 3 large aberrant RBs (aRB) at $t_0$ PenG, vs. larger inclusions containing multiple aRB at $t_{18}$ PenG.

These results indicate that these peptides induce antibody responses that recognize persistently infected cells, which is a basis for treatment of persistent infection with the present peptide immunogens. This is believed to be the first example of an anti-chlamydial immunogen (vaccine candidate) inducing such responses that permit induction of such strong, genus-wide protective immunity against *Chlamydia*.

EXAMPLE VIII

Sera from Patients with Documented Genital Chlamydial Infections Have Anti-Peptide Antibodies To investigate the relationship between anti-peptide immunity and human infection, coded ("de-identified") human sera from patients with known genital tract chlamydial infection and antibodies to chlamydial polymorphic membrane proteins (Pmp) (e.g., Grimwood, J et al., 2001, *Infect. Immunity* 69:2383-9) were tested in ELISA against Pep4, Pep7, Pep8 and Pep10 and control "irrelevant" peptides with anti-Human IgG detecting reagents. Sera were tested for their ability to bind (and stain) *C. trachomatis*-infected (48 hr) HEp2 cells by immunohistochemistry (IHC) using the same methods as above except that an anti-human IgG conjugated to a fluorescent dye (either FITC or Alexa dye 488) was used to detect human serum reactivity. Results are shown in Table 5.

Responses to irrelevant peptides were uniformly negative (not shown). Uninfected cells were not stained. With increased exposures to Chlamydiae, the seroreactivity to the peptides (as well as to Pmps) increased, as demonstrated in Group 2 above. Undocumented or persistent infections may account for anti-peptide reactivity in sera of Group 1 and Group 3 patients.

The association of positive anti-peptide ELISA, Pmp reactivity and staining of infected cells (IHC) of sera from patients with exposure(s) to *Chlamydia* demonstrate the importance of the present peptides to anti-chlamydial immunity and the utility such peptides as anti-*Chlamydia* immunogens and in vaccines.

TABLE 5

| Group (n) | Current Infection | # Infections | anti-Pmp Reactivity | Number Positive (peptides recognized) | Reactivity > in IHC | |
|---|---|---|---|---|---|---|
| 1 | None | 0 | Neg | 3/5 (≥3 peptides) | 4/5 | + |
| (5) | | | | 2/5 (1 peptide, each) | 1/5 | +++ |
| 2 | All | 1-3 | Pos | 5/5 (4 peptides) | 4/5 | +++ |
| (5) | | | | | 1/5 | ++ |
| 3 | None | 0 | Pos | 2/2 (1 peptide_ | 2/2 | + or ++ |
| (2) | | | | | | |

IHC: immunohistochemistry; + represents faint staining, ++ represents intermediate staining; +++ represents bright staining.

EXAMPLE IX

Gross Anatomical Observations of Peptide Immunized Subjects

Examination of tissues in the reproductive regions of immunized female mice showed that peptide immunization reduced inflammation.

Genital tracts were exposed at necropsy ~28 days post-challenge to score inflammatory changes (and then removed for histological analysis). Results are shown in FIG. 15. The left panel shows intense inflammation of very purple uterine horns (ovaries difficult to see) in a control animal receiving only adjuvant. None of the animals immunized with peptides showed such intense inflammation. Representative examples for recipients of Peptides 4 and 7 are shown in the center and right panels, respectively. Yellow arrows point to uterine horns (which are further demarcated with dashed lines). It is evident that the peptide immunogens reduced the gross pathology of the genital tract even weeks after challenge. This has been reproduced in a second experiment in which control mice received an irrelevant peptide instead of Peptides 4 or 7. Based on what is known in the art from other contexts, the histopathological results are expected to be consistent with these gross anatomical observations.

EXAMPLE X

Immunization with Free vs. Microencapsulated Peptides

Additional studies were conducted to evaluate and compare the effects of immunization with the present peptides in free vs. microencapsulated form in PLA microparticles (MPs). Results are shown in FIGS. 17, 18A-18F and 19A-19B. FIG. 17 shows results in whereas FIGS. 18A-18F shows DFA results in infected (challenged) mice.) Animals were immunized subcutaneously with various doses of the free Pep4 or encapsulated (Pep4-MP) form.

Mice were immunized subcutaneously 3 times (primary, 1st first boost at day 14, $2^{nd}$ boost at day 28) according to a schedule shown below with the indicated peptide antigen or soluble mAb2 polypeptide or were control animals that were infected but not immunized (relevant for FIG. 18A-F). Free Pep4 peptide was tested at the 40 μg dose, whereas Pep4-MP was tested at 10, 20 and 40 μg doses. Blood was collected before each immunization and at the end of the experiment (day +28). The number of subjects (n) in each group is shown in FIG. 17.

Immunization and Bleeding Schedule:

| DAY | |
|---|---|
| −42 | Prebleed before first immunization (Δ in ELISA), Mice were then primed. |
| −28 | Bleed 14 d. after primary immunization (▲ in ELISA). Mice were then given $1^{st}$ boost |
| −14 | Bleed 14 d. after $1^{st}$ boost (28 d. after primary) (○ in ELISA). Mice were then given $2^{nd}$ boost. |
| 0 | Bleed 14 d. after $2^{nd}$ boost (42 d. after primary) (● in ELISA) (no further boosts) Mice were challenged with live chlamydia |
| +7, +14, +21, +28: | Vaginal swabs were collected (weekly) after challenge |
| +28 | Terminal bleed and day of sacrifice (▼ in ELISA). |

FIG. 18 shows results of DFA staining of the vaginal swabs obtained as described above. This assay detects organisms present in vaginal smears. Statistically significant differences (wherein p is <0.05 or lower using Student's t test) are shown in Table 6. Results not appearing in this table (whether the variable is day after immunization, dose or form of antigen, etc.) were not statistically different from their controls.

TABLE 6

Significant Difference in DFA detection of chlamydial load in vaginal swabs (see FIG. 18)

| | Day after Challenge | | | | | | | | | | |
|---|---|---|---|---|---|---|---|---|---|---|---|
| | 14 | | | 22 | | | | | 28 | | |
| | Antigen | | | | | | | | | | |
| | Pep4-MP | | | Pep4-MP | | | Free Pep4 | sol. mAb2 | Pep4-MP | | |
| | Dose (μg) | | | | | | | | | | |
| | 10 | 20 | 40 | 10 | 20 | 40 | 40 | 100 | 10 | 20 | 40 |
| p value | <0.05 | <0.05 | <0.05 | <0.01 | <0.05 | <0.05 | <0.01 | <0.01 | <0.05 | <0.01 | <0.05 |

Pep4-MP = Pep4 in PLA microparticles; Sol. mAb2 = soluble mAb2; P values obtained using Student's t test compared to controls.

It was concluded from these studies that Pep4 delivered in microparticles significantly reduces bacterial load after infectious vaginal challenge in a dose-dependent manner. This outcome correlates with stronger immune responses (shown in ELISA where the anti-Pep4 antibody responses were also significantly greater when the antigen was delivered in microparticles. Therefore the protective effects are a result of the stronger immunity. (The ELISA results showed that immunizing with free Pep4 (at the 40 μg dosing) was not as immunogenic as encapsulated Pep4 at equal or lower doses.)

Figure 9:
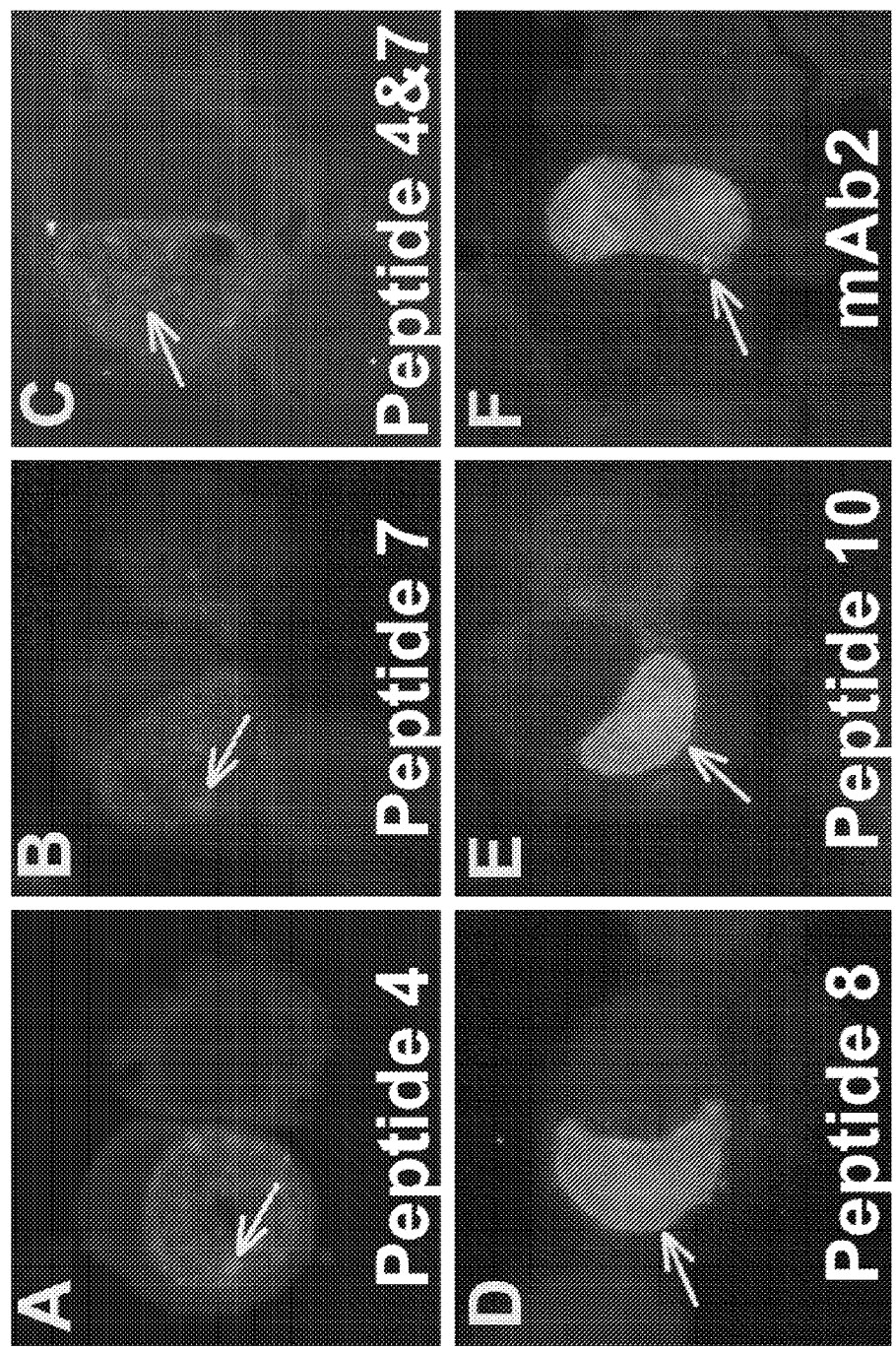
Figure 10:
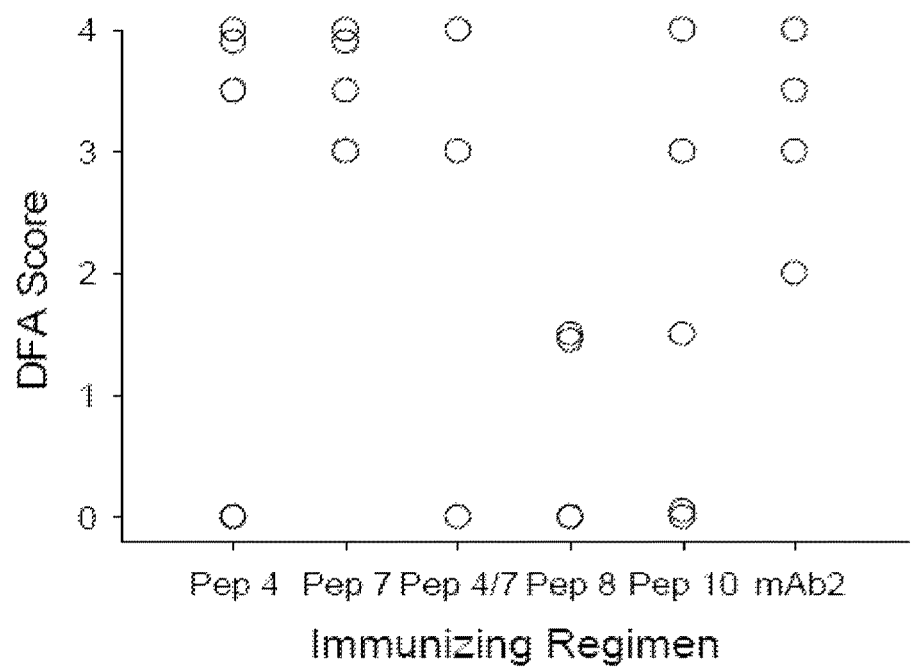
Figure 11:
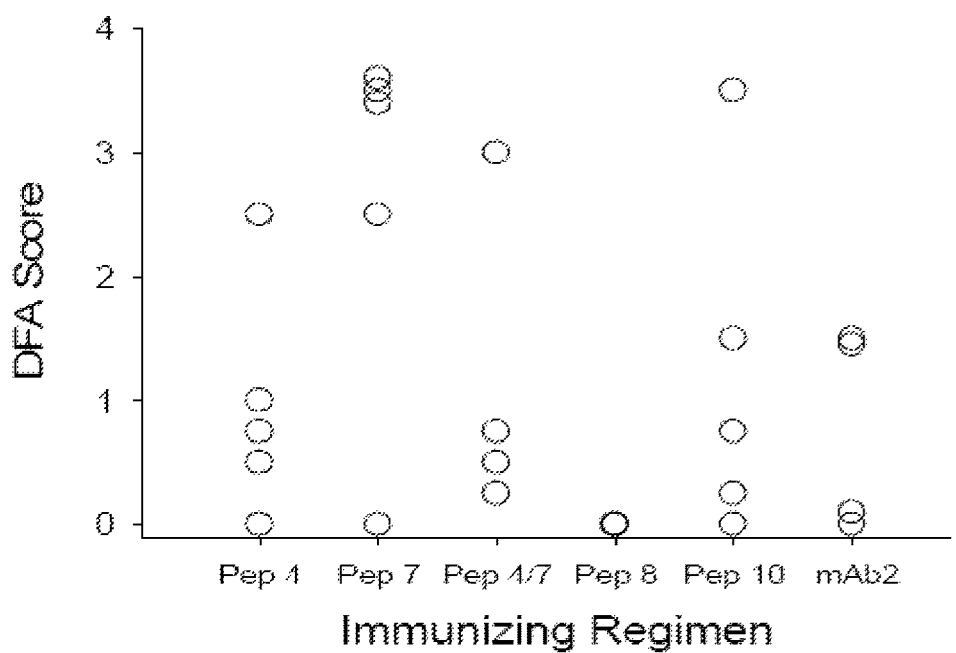

In a preferred embodiment, an encapsulated combination of two or more of the present peptides (whether individually encapsulated and the MP's mixed, or whether co-encapsulated, is used to induce immunity and protection (as shown for the combination of Pep4 and Pep7 in Example IV (see FIG. 9C)

Studies comparing the immunologic and protective effect 20 μg Pep4-MP using subcutaneous vs. oral administration will show that oral immunization is also effective in inducing ant-Pep4 antibodies, which also bind specifically to *Chlamydia*-infected vs. non-infected cells by the DFA. Therefore, oral immunization with the peptides of the present invention when encapsulated in microparticles, as well as nanoparticles, is an effective means to induce protective immunity against *Chlamydia*. The results using intact mAb2 showed a 10-25-fold improvement in immunization and protection if the encapsulated mAb2 (6-10 μg/dose) were delivered orally compared to subcutaneously as 100 μg of soluble mAb2.

Studies to confirm and analyze the release of immunogenic peptides from encapsulated formulations (in PLA) as used above were conducted. Results are shown in FIGS. 19A-B. Cumulative peptide release rates of two different encapsulated preparations of Pep 4 were calculated by performing HPLC on samples of supernatant collected over time; leftover samples were used to assay Pep 4 by ELISA. The release rates of the peptide were similar in the two preparations. The first preparation of Pep4-MP in FIG. 19A ("Release-1") was used for the experiments described above. Both preparations will also induce immunity when delivered by oral administration.

EXAMPLE XI

Correlation of PCR (for *Chlamydia*) and Immunological Analysis of Human Samples Human sera were tested by PCR for expression of several chlamydial genes, by IHC against *C. trachomatis*-infected cells and by ELISA against several of the peptides of the present invention. Results are shown in Table 7 (below) which include results from PCR-studies for presence of DNA encoding the chlamydial Major Outer Membrane Protein (MOMP) in human peripheral blood mononuclear cells (PBMC) (which are primarily lymphocytes and monocytes) and cervical swabs Also shown is IHC staining of *C. trachomatis*-infected human HEp2 cells and binding of antibodies in the patient samples to four peptides of the present invention (Pep4, 7, 8, and 10) in ELISA.

Table 7 shows that 9/24 samples were PCR-positive (by any of the PCR assays) and were positive for IHC staining and ELISA (at 1:40 and 1:80 dilutions of sera, the majority were positive at both). 13 of 24 samples were PCR-positive (any assay) and were positive in IHC staining and/or ELISA. 11 of 24 samples were PCR-positive in assays for MOMP or the chlamydial plasmid (the plasmid is not carried by all chlamydial strains) but were positive in IHC and/or ELISA (not all samples tested by ELISA).

It is evident that 17/24 sera from were from subjects documented to have chlamydial infections on the basis of PCR-positivity These sera of infected individuals bound to and resulted in staining of *C. trachomatis*-infected cells and positive ELISA results with the four peptides (albeit with different titers and intensities of staining and ELISA.

Therefore patients with confirmed *Chlamydia* infection produce antibodies against peptides of the present invention, further supporting the expectation that, in addition to the animal studies, these peptides are effective for diagnosis as well as for human immunization when administered in an immunogenic composition (i.e., administered with appropriate adjuvants or other immunostimulatory moieties, encapsulated as micro- or nano-particles, etc.). If a patient's serum contains antibodies recognizing whole chlamydial organism in either the EB or RB stage, there will be antibodies which also recognize all 4 peptides, strengthening the notion that these peptides will serve as appropriate vaccine and diagnostic antigens.

TABLE 7

PCR and Immunoreactivity of Human Serum Samples

| Sample # | PCR for MOMP (PBMC) | PCR for MOMP (Cervix swabs) | PCR for Chlamyd Plasmid | Staining results | Staining localization Inclusion association | ELISA 1:40 on 4 peptides Scale: 1+-3+ | | | | |
|---|---|---|---|---|---|---|---|---|---|---|
| | | | | | | 4 | 7 | 8 | 10 | Mean |
| 1 | +/+ | +/+ | +/+ | 3+ | RB memb, EB, matrix material | 2 | 1.5 | 2 | 2 | 1.9 |
| 2 | −/−/+/+ | −/−/+/+ | n/d | 1+ | EB, RB, not inclusion memb, except picture 1 | 0.75 | 1 | 1 | 1 | 0.9 |
| 3 | −/−/+/+ | −/−/− | − | 3+ | Inclusion memb proof, EB, RB, matrix | 2.5 | 2.5 | 2.5 | 2.5 | 2.5 |
| 4 | −/+/+/+ | −/−/−/− | n/d | 1+ | EB circles inside inclusion | | | | | |
| 5 | − | −/+ | n/d | ± | Very faint but "real" | 2 | 2 | 2 | 1.5 | 1.9 |
| 6 | − | −/− | n/d | 1+ | "Bitten out" inclusion, inclusion memb | | | | | |
| 7 | +/+ | −/− | − | − to ± | Very faint | 0.75 | 0.75 | 1 | 1 | 0.9 |
| 8 | +/+/+ | +/−/− | n/d | 3+ | Very bright! EB circles Inclusion memb | 3 | 3 | 3 | 3 | 3 |
| 9 | − | −/− | −/−/− | 2+ | Real +, inclusion memb and EB, hazy inside | 3 | 3 | 3 | 3 | 3 |
| 10 | − | −/− | n/d | 1+ | Definite +, refer to slide #25 empty | 3 | 2 | 2 | 2 | 2.3 |
| 11 | +/+ | +/+ | − | ± to 1+ | Very faint, EB probably only, RB not convinced | | | | | |
| 12 | +/+ | −/− | n/d | 2+ | Hazy, particles | 2 | 1.5 | 2 | 2 | 1.9 |
| 13 | − | −/− | −/−/− | ± | Very faint but real | 2 | 2 | 2 | 2 | 2 |
| 14 | | | | n/d | Negative control | | | | | |
| 15 | | | | + | Positive control | | | | | |
| 16 | +/+/− | −/− | n/d | 2+ | EB/RB, possible inclusion membrane | 2 | 1.5 | 1.5 | 1 | 1.5 |
| 17 | +/+ | − | n/d | 1+ | Faint, hazy, EB; possible inclusion membrane | | | | | |
| 18 | − | −/− | n/d | 2+ | uncertain | 2.5 | 3 | 3 | 2 | 2.6 |
| 19 | −/−/+/+ | −/−/−/− | n/d | ± | Faint, particles stained, no inclusion memb | | | | | |
| 20 | − | −/−/− | −/− | 1+ | Very faint staining | | | | | |
| 21 | − | −/−/− | n/d | 1+ | Faint; possible memb staining RBs | 1.5 | 2 | 3 | 3 | 2.1 |

TABLE 7-continued

PCR and Immunoreactivity of Human Serum Samples

| Sample # | PCR for MOMP (PBMC) | PCR for MOMP (Cervix swabs) | PCR for Chlamyd Plasmid | Staining results | Staining localization Inclusion association | ELISA 1:40 on 4 peptides Scale: 1+-3+ | | | | |
|---|---|---|---|---|---|---|---|---|---|---|
| | | | | | | 4 | 7 | 8 | 10 | Mean |
| 22 | +/−/+/+ | −/−/−/− | n/d | 2+ | Inclusion memb plus EB/RB | 1.5 | 1.5 | 1.5 | 2 | 1.6 |
| 23 | − | −/−/− | −/− | 2+ | True staining | 2 | 1.5 | 1.5 | 1 | 1.5 |
| 24 | − | −/− | n/d | ± to 1+ | Hazy | 3 | 1.5 | 2 | 2 | 2.1? |
| 25 | − | −/−/− | −/− | 1+ | Faint but real, empty portion | x | x | x | x | x |
| 26 | − | −/−/− | −/− | 1+ | Not inclusion memb, EB/RB, "bitten out" inclusion | 2 | 2 | 2 | 1.5 | 1.9 |

The PCR for MOMP is nested. For more information about MOMP-PCR used here, see, MOMP PCR: B. Dutilh et al., Res Microbial. 1989, 140:7-16; P. Rodriguez et al., J. Clin Micro. 1991, 29: 1132-36. For plasmid PCR, see, S. Bas et al., Arthritis Rheum. 1995, 38:005-13 (incorporated by reference in their entirety).

The multiple entries (+,−, etc.) in the PCR columns represent independent PCR tests carried out by different lab personnel. Positive and negative PCR are dictated by careful controls that exclude false positives and negatives; thus positive PCR is robust Negative cervical swabs means that there no current infection (or that the infection ascended from the cervix and a vaginal swab would not detect shed organism).

Positive "staining" and the presence of any numbers representing ELISA reactivity also suggest prior infection, or ascended infection. Positive antibody staining of infected cells in the face of negative PCR results suggests the existence of prior (but not current) infection. ELISA results are completely concordant with staining results. Dissimilar ELISA values against 4 peptides seems to correlate with weaker immunostaining.

DOCUMENTS CITED BY NUMBER

1. Honey, E., Templeton, A. (2002) Prevention of pelvic inflammatory disease by the control of C. trachomatis infection. Int. J Gynaecol. Obstet. 78, 257
2. Wiesenfeld, H. C., Hillier, S. L., Krohn, M. A., Amortegui, A. J., Heine, R. P., Landers, D. V., Sweet, R. L. (2002) Lower genital tract infection and endometritis: insight into subclinical pelvic inflammatory disease. Obstet. Gynecol. 100, 456-463
3. (2002) CDC and Prevention. Screening tests to detect C trachomatis and N gonorreheae infections-2002. MMWR 51, 1-3
4. Ho, J. L., He, S. H., Hu, A. R., Geng, J. Y., Basile, F. G., Almeida, M. G. B., Saito, A. Y., Laurence, J., Johnson, W. D. (1995) Neutrophils from human HIV-seronegative donors induce HIV replication from HIV-infected patients mononuclear cells and cell lines—an in vitro model of HIV transmission facilitated by Chlamydia trachomatis. J. Exp. Med. 181, 1493-1505
5. Schachter, J., Grossman, M., Sweet, R. L., et al. (1986) Prospective study of perinatal transmission of Chlamydia trachomatis. J. Amer. Med. Assoc. 255, 3374-3377
6. Rapoza, P. A., Quinn, T. C., Kiessling, L. A., Taylor, H. R. (1986) Epidemiology of neonatal conjunctivitis. Ophthalmology. 93, 456-461
7. Dreses-Werringloer, U., Padubrin, I., Jurgens-Saathoff, B., Hudson, A. P., Zeidler, H., Kohler, L. (2000) Persistence of Chlamydia trachomatis is induced by ciprofloxacin and ofloxacin in vitro, Antimicrob. Agents Chemother. 44, 3288-3297
8. Wyrick, P. B., Knight, S. T. (2004) Pre-exposure of infected human endometrial epithelial cells to penicillin in vitro renders Chlamydia trachomatis refractory to azithromycin. J. Antimicrob. Chemother. 54, 79-85
9. Su, H., Morrison, R., Messer, R., Whitmire, W., Hughes, S., Caldwell, H. D. (1999) The effect of doxycycline treatment on the development of protective immunity in a murine model of chlamydial genital infection. J Infect Dis 180, 1252-1258
10. Gerard, H. C., Kohler, L., Branigan, P. J., Zeidler, H., Schumacher, H. R., Hudson, A. P. (1998) Viability and gene expression in Chlamydia trachomatis during persistent infection of cultured human monocytes. Med. Microbiol Immunol (Berl) 187, 115-120
11. Schumacher, H. R., Jr., Magge, S., Cherian, P. V., Sleckman, J., Rothfuss, S., Clayburne, G., Sieck, M. (1988) Light and electron microscopic studies on the synovial membrane in Reiter's syndrome Immunocytochemical identification of chlamydial antigen in patients with early disease. Arthrit Rheum 31, 937-946
12. Bavoil, P. M., Wyrick, P. B. (eds.) (2007) Chlamydia: Genomics and Pathogenesis. Horizon Press, Inc., Norwich, UK
13. Abu el-Asrar, A. M., Geboes, K., Tabbara, K. F., al Kharashi, S. A., Missotten, L., Desmet, V. (1998) Immunopathogenesis of conjunctival scarring in trachoma. Eye 12, 453-460
14. Heggie, A. D., Lass, J. H. (1994) Principles and practice of ophthalmology: Basic sciences. Saunders, Philadelphia.
15. Saikku, P. (1997) Chlamydia pneumoniae and atherosclerosis—an update. Scan. J. Infect Dis.—Suppl 104, 53-56
16. Wong, Y., Ward, M. E. (1999) Chlamydia pneumoniae and atherosclerosis. J Clin. Pathol. 52, 398-399
17. Balin, B. J., Gerard, H. C., Arking, E. J., Appelt, D. M., Branigan, P. J., Abrams, J. T., Whittum-Hudson, J. A., Hudson, A. P. (1998) Identification and localization of Chlamydia pneumoniae in the Alzheimer's brain. Med Microbiol Immunol (Berl) 187, 23-42
18. Mahony, J., Woulfe, J., Munoz, D., Chong, S., Browning, D., Smieja, M. Chlamydia pneumoniae in the Alzheimer's brain-is DNA detection hampered by low copy number? Proc. Fourth Eur. Chlamydia Research Meeting, Aug. 2000 4, 275. 2000
19. Sriram, S., Mitchell, W., Stratton, C. (1998) Multiple sclerosis associated with Chlamydia pneumoniae infection of the CNS. Neurology 50, 571-572
20. Stratton, C. W., Sriram, S. (2003) Association of Chlamydia pneumoniae with central nervous system disease. Microbes Infect. 5, 1249-1253

21. Henry, C. H., Hudson, A. P., Gerard, H. C., Franco, P. F., Wolford, L. M. (1999) Identification of *Chlamydia trachomatis* in the human temperomandibular joint. *J. Oral Maxillofac. Surg.* 57, 683-688

22. Henry, C. H., Hughes, C. V., Gerard, H. C., Hudson, A. P., Wolford, L. M. (2000) Reactive arthritis: preliminary microbiologic analysis of the human temperomandibular joint. *J Oral Maxillofac. Surg.* 58, 1137-1142

23. Henry, C H., Whittum-Hudson, J A., Tull, G T, Wolford, L M. (2008) Reactive arthritis and internal derangement of the temperomandibular joint. *Oral Surg Oral Med Oral Pathol Oral Radiol Endod.* 105:698-701

24. Zhang, Q., Powers, E. T., Nieva, J., Huff, M. E., Dendle, M. A., Bieschke, J., Glabe, C. G., Eschenmoser, A., Wentworth, P., Jr., Lerner, R. A., Kelly, J. W. (2004) Metabolite-initiated protein misfolding may trigger Alzheimer's disease. *Proc. Natl. Acad. Sci. USA* 101, 4752-4757

25. Grimes, J. E., Wyrick, P. B. (1995) Chlamydiosis (Ornithosis). In *Diseases of Poultry* pp. 311-25

26. Whittum-Hudson, J. A., An, L.-L., MacDonald, A. B., Prendergast, R. A., Saltzman, W. M. (1996) Oral immunization with an anti-idiotypic antibody to the exoglycolipid antigen protects against experimental *Chlamydia trachomatis* infection. *Nat Med.* 2, 1116-1121

27. Whittum-Hudson, J. A., Rudy, D., Gerard, H., Vora, G., Davis, E., Haller, P. K., Prattis, S. M., Hudson, A. P., Saltzman, W. M., Stuart, E. S. (2001) The anti-Idiotypic antibody to chlamydial glycolipid exoantigen (GLXA) protects mice against genital infection with a human biovar of *Chlamydia trachomatis*. *Vaccine* 19, 4061-4071

28. Bharatwaj, B., Anbalagan, A., Wu, L., Whittum-Hudson, J. A., da Rocha, S. R. P. (2007) Towards novel inhalation formulations for the delivery of therapeutic molecules for chlamydial respiratory infections. ENANTBio abstract.

29. Bharatwaj, B., Wu, L., Whittum-Hudson, J. A., da Rocha, S. R. P. A Trojan horse approach for the non-invasive delivery of nanotherapeutics to and through the lungs. AIChE submitted. 2008.

30. Whittum-Hudson, J. A., Panyam, J., Kannan, R. M., Hudson, A. Nanotechnology Approaches to In Vitro and In Vivo Studies of an Intracellular Bacterium, *Chlamydia trachomatis*. ENANTBio poster, 2007

31. Amidi, M., Romeijn, S. G., Borchard, G., Junginger, H. E., Hennink, W. E., Jiskoot, W. (2006) Preparation and characterization of protein-loaded N-trimethyl chitosan nanoparticles as nasal delivery system. *J. Control. Rel.* 111, 107-116

32. Borges, O., Borchard, G., Verhoef, J. C., de Sousa, A., Junginger, H. E. (2005) Preparation of coated nanoparticles for a new mucosal vaccine delivery system. *Int. J. Pharmaceut* 299, 155-166

33. Elamanchili, P., Diwan, M., Cao, M., Samuel, J. (2004) Characterization of poly(D,L-lactic-co-glycolic acid) based nanoparticulate system for enhanced delivery of antigens to dendritic cells. *Vaccine* 22, 2406-2412

34. Jain, K. K. (2006) Nanoparticles as targeting ligands. *Trends in Biotechnology* 24, 143-145

35. Patnaik, S., Aggarwal, A., Nimesh, S., Goel, A., Ganguli, M., Saini, N., Singh, Y., Gupta, K. C. (2006) PEI-alginate nanocomposites as efficient in vitro gene transfection agents. *J Control Rel* 114, 398-409

36. Shen, H., Ackerman, A. L., Cody, V., Giodini, A., Hinson, E. R., Cresswell, P., Edelson, R. L., Saltzman, W. M., Hanlon, D. J. (2006) Enhanced and prolonged cross-presentation following endosomal escape of exogenous antigens encapsulated in biodegradable nanoparticles. *Immunology* 117, 78-88

37. Borges, O., Cordeiro-da-Silva, A., Romeijn, S. G., Amidi, M., de Sousa, A., Borchard, G., Junginger, H. E. (2006) Uptake studies in rat Peyer's patches, cytotoxicity and release studies of alginate coated chitosan nanoparticles for mucosal vaccination. *J. Control. Rel.* 114, 348-358

38. Desai, M. P., Labhasetwar, V., Amidon, G. L., Levy, R. J. (1996) Gastrointestinal uptake of biodegradable microparticles: effect of particle size. *Pharm. Res.* 13, 1838-1845

39. Jiang, W., Kim, B. Y. S., Rutka, J. T., Chan, W. C. W. (2008) Nanoparticle-mediated cellular response is size-dependent. *Nat. Nanotech.* 3, 145-150

40. Tabata, Y., Inoue, Y., Ikada, Y. (1996) Size effect on systemic and mucosal immune responses induced by oral administration of biodegradable microspheres. *Vaccine* 14, 1677-1685

41. Win, K. Y., Feng, S. S. (2005) Effects of particle size and surface coating on cellular uptake of polymeric nanoparticles for oral delivery of anticancer drugs. *Biomaterials* 26, 2713-2722

42. Keegan, M. E., Whittum-Hudson, J. A., Mark Saltzman, W. (2003) Biomimetic design in microparticulate vaccines. *Biomaterials* 24, 4435-4443

43. Lopez-Requena, A., o, de Acosta, C. M., Moreno, E., Gonzalez, M., Puchades, Y., Talayera, A., Vispo, N. S., Vazquez, A. M., Perez, R. (2007) Gangliosides, Ab1 and Ab2 antibodies: I. Towards a molecular dissection of an idiotype-anti-idiotype system. *Mol. Immunol.* 44, 423-433

44. Lopez-Requena, A., Rodriguez, M., de Acosta, C. M., Moreno, E., Puchades, Y., Gonzalez, M., Talayera, A., Valle, A., Hernandez, T., Vazquez, A. M., Perez, R. (2007) Gangliosides, Ab1 and Ab2 antibodies: II. Light versus heavy chain: An idiotype-anti-idiotype case study. *Mol. Immunol.* 44, 1015-1028

45. Noel, D., Bernardi, T., Navarro-Teulon, I., Marin, M., Martinetto, J. P., Ducancel, F., Mani, J. C., Pau, B., Piechaczyk, M., iard-Piechaczyk, M. (1996) Analysis of the individual contributions of immunoglobulin heavy and light chains to the binding of antigen using cell transfection and plasmon resonance analysis. *J. Immunol. Meth.* 193, 177-187

46. Batteiger, B. E., Rank, R. G., Bavoil, P. M., Soderberg, L. S. F. (1993) Partial protection against genital reinfection by immunization of guinea pigs with isolated outer membrane proteins of the chlamydial agent guinea pig inclusion conjunctivitis. *J. Gen. Micro.* 139, 2965-2972

47. Dong-Ji, Z., Yang, X., Shen, C., Lu, H., Murdin, A., Brunham, R. C. (2000) Priming with *Chlamydia trachomatis* major outer membrane protein (MOMP) DNA followed by MOMP ISCOM boosting enhances protection and is associated with increased immunoglobulin A and Th1 cellular immune response, *Infect Immun* 68, 3074-3078

48. Wizel, B., Starcher, B. C., Samten, B., Chroneos, Z., Barnes, P. F., Dzuris, J., Higashimoto, Y., Appella, E., Sette, A. (2002) Multiple *Chlamydia pneumoniae* Antigens Prime CD8+ Tc1 Responses That Inhibit Intracellular Growth of This Vacuolar Pathogen. *J Immunol* 169, 2524-2535

49. Igietseme, J. U., Murdin, A. (2000) Induction of protective immunity against *Chlamydia trachomatis* genital infection by a vaccine based on major outer membrane protein-lipophilic immune response-stimulating complexes. *Infect. Immun* 68, 6798-6806

50. Pal, S., Theodor, I., Peterson, E. M., de la Maza, L. M. (1997) Immunization with an acellular vaccine consisting of the outer membrane complex of *Chlamydia trachomatis* induces protection against a genital challenge. *Infect. Immun.* 65, 3361-3369
51. Dawson, C., Jawetz, E., Hanna, L., Rose, L., Wood, T. R., Thygeson, P. (1966) Experimental inclusion conjunctivitis in man. II. Partial resistance to reinfection. *Am. J. Epidemiol.* 84, 411-425
52. Igietseme, J. U., Black, C. M., Caldwell, H. D. (2002) *Chlamydia* vaccines: strategies and status. *BioDrugs* 16, 19-35
53. Taylor, H. R., Johnson, S. L., Prendergast, R. A., Schachter, J., Dawson, C. R., Silverstein, A. M. (1982) An animal model of trachoma II. The importance of repeated reinfection. *Invest. Ophthalmol. Vis. Sci.* 23, 507-515
54. Morrison, R. P. (1990) Immune responses to *Chlamydia* are protective and pathogenetic. In Chlamydial infections (Bowie, W. R., Caldwell, H. D., Jones, R. P., Mardh, P.-A., Ridgway, G. L., Schachter, J., Stamm, W. E., and Ward, M. E., eds) pp. 163-172, Cambridge Univ. Press, Cambridge
55. Morrison, R. P., Lyng, K., Caldwell, H. D. (1989) Chlamydial disease pathogenesis. Ocular hypersensitivity elicited by a genus-specific 57-kD protein. *J. Exp. Med.* 169, 663-675
56. Taylor, H. R., Johnson, S. L., Schachter, J., Caldwell, H. D., Prendergast, R. A. (1987) Pathogenesis of trachoma: the stimulus for inflammation. *J. Immunol.* 138, 3023-3027
57. Taylor, H. R., Maclean, I. W., Brunham, R. C., Pal, S., Whittum-Hudson, J. (1990) Chlamydial heat shock proteins and trachoma. *Infect. Immun.* 58, 3061-3063
58. Rank, R. G., Dascher, C., Bowlin, A. K., Bavoil, P. M. (1995) Systemic immunization with Hsp60 alters the development of chlamydial ocular disease. *Invest. Ophthalmol. Vis. Sci.* 36, 1344-1351
59. Shaw, J., Grund, V., Durling, L., Crane, D., Caldwell, H. D. (2002) Dendritic cells pulsed with a recombinant chlamydial major outer membrane protein antigen elicit a CD4(+) type 2 rather than type 1 immune response that is not protective. *Infect Immun.* 70, 1097-1105
60. Su, H., Messer, R., Whitmire, W., Fischer, E., Portis, J. C., Caldwell, H. D. (1998) Vaccination against chlamydial genital tract infection after immunization with dendritic cells pulsed ex vivo with nonviable Chlamydiae. *J. Exp. Med.* 188, 809-818
61. He, Q., Moore, T. T., Eko, F. O., Lyn, D., Ananaba, G. A., Martin, A., Singh, S., James, L., Stiles, J., Black, C. M., Igietseme, J. U. (2005) Molecular basis for the potency of IL-10-deficient dendritic cells as a highly efficient APC system for activating Th1 response. *J Immunol* 174, 4860-4869
62. Moore, T., Ekworomadu, C. O., Eko, F. O., MacMillan, L., Ramey, K., Ananaba, G. A., Patrickson, J. W., Nagappan, P. R., Lyn, D., Black, C. M., Igietseme, J. U. (2003) Fc Receptor-mediated antibody regulation of T cell immunity against intracellular pathogens. *J. Infect. Dis.* 188, 617-624
63. Anderson, C. F., Mosser, D. M. (2002) Biasing immune responses by directing antigen to macrophage Fc {gamma} receptors. *J. Immunol.* 168, 3697-3701
64. Casadevall, A., Pirofski, L. A. (2003) Antibody-mediated regulation of cellular immunity and the inflammatory response. *Tr. Immunol.* 24, 474-478
65. Campos, M., Pal, S., O'Brien, T. P., Taylor, H. R., Prendergast, R. A., Whittum-Hudson, J. A. (1995) A chlamydial major outer membrane protein extract as a trachoma vaccine candidate. *Invest. Ophthalmol. Vis. Sci.* 36, 1477-1491
66. Sharma, J., Bosnic, A. M., Piper, J. M., Zhong, G. (2004) Human Antibody Responses to a *Chlamydia*-Secreted Protease Factor. *Infect. Immun.* 72, 7164-7171
67. Brade, L., Nurminen, M., Makela, P. H., Brade, H. (1985) Antigenic properties of *Chlamydia trachomatis* lipopolysaccharide. *Infect. Immun.* 48, 569-572
68. Stuart, E. S., MacDonald, A. B. (1982) Isolation of a possible group determinant of *Chlamydia trachomatis*. In Chlamydial Infections (Mardh, P.-A. and et al., eds) pp. 57-60, Elsevier Biomedical, NY
69. Stuart, E. S., MacDonald, A. B. (1984) Identification of two fatty acids in a group determinant of *Chlamydia trachomatis*. *Curr. Microbiol.* 11, 123-128
70. Stuart, E. S., Tirrell, S. M., MacDonald, A. B. (1987) Characterization of an antigen secreted by chlamydial infected cell culture. *Immunology* 61, 527-533
71. Stuart, E. S., Troidle, K. M., MacDonald, A. B. (1994) Chlamydial glycolipid antigen: extracellular accumulation, biological activity, and antibody recognition. *Curr. Microbiol.* 28, 85-90
72. Stuart, E. S., Wyrick, P. B., Choong, J., Stoler, S. B., MacDonald, A. B. (1991) Examination of chlamydial glycolipid with monoclonal antibodies: cellular distribution and epitope binding. *Immunology* 74, 740-747
73. Tirrell, S. M., Stuart, E. S., MacDonald, A. B. (1986) Heterogeneity among chlamydial genus specific LPS and exoglycolipid. In Chlamydial infections (Oriel, D., Ridgeway, G. L., Schachter, J., Taylor-Robinson, D., and Ward, M. E., eds) pp. 126-128, Cambridge Univ. Press, Cambridge
74. Vora, G., Stuart, E. S. (2003) A role for the glycolipid exoantigen (glxa) in chlamydial infectivity. *Curr. Micro.* 46, 217-223
75. Kinnunen, A., Molander, P., Morrison, R., Lehtinen, M., Karttunen, R., Tiitinen, A., Paavonen, J., Surcel, H. M. (2002) Chlamydial heat shock protein 60-specific T cells in inflamed salpingeal tissue. *Fertil. Steril.* 77, 162-166
76. Knight, S. C., Iqball, S., Woods, C., Stagg, A., Ward, M. E., Tuffrey, M. (1995) A peptide of *Chlamydia trachomatis* shown to be a primary T-cell epitope in vitro induces cell-mediated immunity in vivo. *Immunology* 85, 8-15
77. Loomis, W. P., Starnbach, M. N. (2002) T cell responses to *Chlamydia trachomatis*. *Curr. Opin. Microbiol.* 5, 87-91
78. Loomis, W. P., Starnbach, M. N. (2006) *Chlamydia trachomatis* infection alters the development of memory CD8+ T cells. *J Immunol* 177, 4021-4027
79. Morrison, R. P., Caldwell, H. D. (2002) Immunity to Murine Chlamydial Genital Infection. *Infect. Immun.* 70, 2741-2751
80. Starnbach, M. N., Loomis, W. P., Ovendale, P., Regan, D., Hess, B., Alderson, M. R., Fling, S. P. (2003) An inclusion membrane protein from *Chlamydia trachomatis* enters the MHC class I pathway and stimulates a CD8+ T cell response. *J. Immunol.* 171, 4742-4749
81. Follmann, F., Olsen, A. W., Jensen, K. T., Hansen, P. R., Andersen, P., Theisen, M. (2008) Antigenic profiling of a *Chlamydia trachomatis* gene-expression library. *J Infect Dis* 197, 897-905
82. Barker, C. J., Beagley, K. W., Hafner, L. M., Timms, P. (2008) In silico identification and in vivo analysis of a novel T-cell antigen from *Chlamydia*, NrdB. *Vaccine* 26, 1285-1296
83. Karunakaran, K. P., Rey-Ladino, J., Stoynov, N., Berg, K., Shen, C., Jiang, X., Gabel, B. R., Yu, H., Foster, L. J., Brunham, R. C. (2008) Immunoproteomic discovery of novel T cell antigens from the obligate intracellular pathogen *Chlamydia*. *J Immunol* 180, 2459-2465
84. Belay, T., Eko, F. O., Ananaba, G. A., Bowers, S., Moore, T., Lyn, D., Igietseme, J. U. (2002) Chemokine and chemokine receptor dynamics during genital chlamydial infection. *Infect. Immun.* 70, 844-850
85. Darville, T., Andrews, C. W., Jr., Sikes, J. D., Fraley, P. L., Rank, R. G. (2001) Early local cytokine profiles in strains of mice with different outcomes from chlamydial genital tract infection. *Infect Immun* 69, 3556-3561s. *Infect Immun* 68, 3074-3078
86. Maxion, H. K., Kelly, K. A. (2002) Chemokine expression patterns differ within anatomically distinct regions of the genital tract during *Chlamydia trachomatis* infection. *Infect Immun.* 70, 1538-1546
87. Williams, D. M., Grubbs, B. G., Pack, E., Kelly, K., Rank, R. G. (1997) Humoral and cellular immunity in secondary infection due to murine *Chlamydia trachomatis*. *Infect. Immun.* 65, 2876-2882
88. Yang, X., Hayglass, K. T., Brunham, R. C. (1996) Genetically determined differences in IL-10 and IFN-gamma responses correlate with clearance of *Chlamydia trachomatis* mouse pneumonitis infection. *J. Immunol.* 156, 4338-4344
89. Afonso, L. C. C., Scharton, T. M., Vieira, L. W., Wysocka, M., Trinchieri, G., Scott, P. (1994) The adjuvant effect of interleukin-12 in a vaccine against *Leishmania major*. *Science* 263, 235-240
90. Lebman, D. A., Coffman, R. L. (1994) Cytokines in the mucosal immune system. In *Handbook of mucosal immunology* (Ogra, P. L. e. al., ed) pp. 243-250, Academic Press, Inc., New York
91. Wynn, T. A., Eltoum, I., Cheever, A. W., Lewis, F. A., Gause, W. C., Scher, A. (1993) Analysis of cytokine mRNA expression during primary granuloma formation induced by eggs of *Schistosoma mansoni*. *J. Immunol.* 151, 1430-1440
92. Williams, D. M., Grubbs, B. G., Darville, T., Kelly, K., Rank, R. G. (1998) A role for interleukin-6 in host defense against murine *Chlamydia trachomatis* infection. *Infect Immun* 66, 4564-4567
93. Morrison, R. P., Feilzer, K., Tumas, D. B. (1996) Gene knockout mice establish a primary protective role for major histocompatibility complex class II-restricted responses in *Chlamydia trachomatis* genital tract infection. *Infect. Immun.* 63, 4661-4668
94. Kelso, A. (1995) Th1 and Th2 subsets: paradigms lost? *Immunol. Today* 16, 374-379
95. McGuirk, P., Mills, K. H. G. (2002) Pathogen-specific regulatory T cells provoke a shift in the Th1/Th2 paradigm in immunity to infectious diseases. *Tr. Immunol.* 23, 450-455
96. Ojcius, D. M., Gachelin, G., Dautry-Varsat, A. (1996) Presentation of antigens derived from microorganisms residing in host-cell vacuoles. *Tr. Microbiol.* 4, 53-59
97. Fling, S. P., Sutherland, R. A., Steele, L. N., Hess, B., D'Orazio, S. E., Maisonneuve, J. F., Lampe, M. F., Probst, P., Starnbach, M. N. (2001) CD8+ T cells recognize an inclusion membrane-associated protein from the vacuolar pathogen *Chlamydia trachomatis*. *Proc. Natl. Acad. Sci. U.S.A.* 98, 1160-1165
98. Rasmussen, S. J., Timms, P., Beatty, P. R., Stephens, R. S. (1996) Cytotoxic-T-lymphocyte-mediated cytolysis of L cells persistently infected with *Chlamydia* spp. *Infect. Immun.* 64, 1944-1949
99. Starnbach, M. N., Bevan, M. J., Lampe, M. F. (1995) Murine cytotoxic T lymphocytes induced following *Chlamydia trachomatis* intraperitoneal or genital tract infection respond to cells infected with multiple serovars. *Infect. Immun.* 63, 3527-3530
100. Beutler, A. M., Hudson, A. P., Whittum-Hudson, J. A., Salameh, W. S., Gerard, H. C., Branigan, P. J., Schumacher, H. R. (1997) *C trachomatis* can persist in joint tissue after antibiotic treatment in chronic Reiter's syndrome/reactive arthritis. *J. Clin. Rheumatol.* 3, 125-130
101. Gerard, H. C., Branigan, P. J., Schumacher, H. R., Hudson, A. P. (1998) Synovial *Chlamydia trachomatis* in patients with reactive arthritis/Reiter's syndrome are viable but show aberrant gene expression. *J. Rheumatol.* 25, 734-742
102. Hammer, M., Nettelnbreker, E., Hopf, S., Schmitz, E., Porschke, K., Zeidler, H. (1992) Chlamydial rRNA in the joints of patients with *Chlamydia*-induced arthritis and undifferentiated arthritis. *Clin. Exp. Rheumatol.* 10, 63-66
103. Hannu, T., Puolakkainen, M., Leirisalo-Repo, M. (1999) *Chlamydia pneumoniae* as a triggering infection in reactive arthritis. *Rheumatology (Oxford)* 38, 411-414
104. (no citation)
105. Holland, S. M., Hudson, A. P., Bobo, L., Whittum-Hudson, J. A., Viscidi, R. P., Quinn, T. C., Taylor, H. R. (1992). Demonstration of chlamydial RNA and DNA during a culture-negative state. *Infect. Immun.* 60:2040-2047
106. Keat, A., Dixey, J., Soonex, C., Thomas, B., Osdorne, M., Taylor-Robinson, D. (1987) *C trachomatis* and reactive arthritis: the missing link. Lancet 1, 72-74
107. Nanagara, R., Li, F., Beutler, A., Hudson, A., Schumacher, H. R., Jr. (1995) Alteration of *Chlamydia trachomatis* biologic behavior in synovial membranes. Suppression of surface antigen production in reactive arthritis and Reiter's syndrome. *Arthritis Rheum.* 38, 1410-1417
108. Inman, R. D., Whittum-Hudson, J. A., Schumacher, H. R., Hudson, A. P. (2000) *Chlamydia* and associated arthritis. *Curr. Opin. Rheumatol.* 12, 254-262
109. Whittum-Hudson, J. A., Gerard, H. C., Schumacher, H. R., Jr., Hudson, A. P. (2008) Pathogenesis of *Chlamydia*-Associated Arthritis. In *Chlamydia* Genomics and Pathogenesis (Bavoil, P. M. and Wyrick, P. B., eds) pp. 475-504, Horizon Bioscience, Norfolk, UK
110. Norton, W. L., Lewis, D., Ziff, M. (1966) Light and electron microscopic observation on the synovitis of Reiter's disease. *Arthrit. Rheum.* 9, 747-757
111. (no citation)
112. Schachter, J., Barnes, M. G., Jones, J. P., Jr., Engleman, E. P., Meyer, K. F. (1966) Isolation of bedsoniae from the joints of patients with Reiter's syndrome. *Proc. Soc. Exp. Biol. Med.* 122, 283-285
113. Gerard, H. C., Branigan, P. J., Balsara, G. R., Heath, C., Minassian, S. S., Hudson, A. P. (1998) Viability of *Chlamydia trachomatis* in fallopian tubes of patients with ectopic pregnancy. *Fertil. Steril.* 70, 945-948
114. Gerard, H. C., Schumacher, H. R., El Gabalawy, H., Goldbach-Mansky, R., Hudson, A. P. (2000) *Chlamydia pneumoniae* present in the human synovium are viable and metabolically active. *Microb. Pathog.* 29, 17-24
115. Hudson, A. P., McEntee, C. M., Reacher, M., Whittum-Hudson, J. A., Taylor, H. R. (1992) Inapparent ocular infection by *Chlamydia trachomatis* in experimental and human trachoma. *Curr. Eye Res.* 11, 279-283
116. Hogan, R. J., Mathews, S. A., Mukhopadhyay, S., Summersgill, J. T., Timms, P. (2004) Chlamydial persistence: beyond the biphasic paradigm. *Infect. Immun* 72: 1843-1855
117. Campbell, L. A., O'Brien, E. R., Cappuccio, A. L., et al. (1995) Detection of *Chlamydia pneumoniae* TWAR in human coronary atherectomy tissues. *J. Infect. Dis.* 172, 585-588

118. Gerard, H. C., Freise, J., Wang, Z., Roberts, G., Rudy, D., Opatz, B., Kohler, L., Zeidler, H., Schumacher, H. R., Whittum-Hudson, J. A., Hudson, A. P. (2002) *Chlamydia trachomatis* genes whose products are related to energy metabolism are expressed differentially in active vs. persistent infection. *Microb. Infect.* 4, 13-22

119. Mahony, J. B., Luinstra, K. E., Sellors, J. W., Jang, D., Chemesky, M. A. (1992) Confirmatory polymerase chain reaction testing for *Chlamydia trachomatis* in first-void urine from asymptomatic and symptomatic men. *J. Clin. Microbiol.* 30, 2241-2245

120. Ostergaard, L., Traulsen, J., Birkelund, S., Christiansen, G. (1991) Evaluation of urogenital *Chlamydia trachomatis* infections by cell culture and the polymerase chain reaction using a closed system. *Eur. J. Clin. Microbiol. Infect. Dis.* 10, 1057-1061

121. Rahman, M. U., Cheema, M. A., Schumacher, H. R., Hudson, A. P. (1992) Molecular evidence for the presence of *Chlamydia* in the synovium of patients with Reiter's syndrome. *Arthritis Rheum.* 35, 521-529

122. Wordsworth, B. P., Hughes, R. A., Allan, I., Keat, A. C., Bell, J. I. (1990) Chlamydial DNA is absent from the joints of patients with sexually acquired reactive arthritis. *Br. J. Rheumatol.* 29, 208-210

123. Gerard, H. C., Whittum-Hudson, J. A., Schumacher, H. R., Hudson, A. P. (2004) Differential expression of three *Chlamydia trachomatis* hsp60-encoding genes in active vs persistent infection. *Microb. Pathog.* 36, 35-39

124. Whittum-Hudson, J. A., Gerard, H. C., Clayburne, G., Schumacher, H. R., Hudson, A. P. (1999) A non-invasive murine model of *Chlamydia*-induced reactive arthritis. *Rev. Rhum. [Engl. Ed.]* 66, 50S-56S 125. Whittum-Hudson, J. A., O'Brien, T. P., Prendergast, J. A. (1995) Murine model of ocular infection by a human biovar of *Chlamydia trachomatis*. *Invest. Ophthalmol. Vis. Sci.* 36, 1976-1987

126. Whittum-Hudson, J. A., Rao, J. P., Hudson, A. P. (2000) Competitive PCR shows vaccination reduces chlamydial DNA in synovium. *Arthrit. Rheum.* 43 (Suppl), 5174

127. Moazed, T. C., Kuo, C. C., Grayston, J. T., Campbell, L. A. (1998) Evidence of systemic dissemination of *Chlamydia pneumoniae* via macrophages in the mouse. *J. Infect. Dis.* 177, 1322-1325

128. Hough, A. J., Jr., Rank, R. G. (1988) Induction of arthritis in C57B1/6 mice by chlamydial antigen. Effect of prior immunization or infection. *Am. J. Pathol.* 130, 163-172

129. Gerard, H. C., Lu, L., Schumacher, H. R., Clayburne, G., Whittum-Hudson, J. A., Rank, R. G., Hudson, A. P. Time course and pathologic consequences of dissemination of *Chlamydia* to the joint following genital infection in a guinea pig model of reactive arthritis. ASM Abstracts 1999 General Meeting, 53. 1999

130. Inman, R. D., Chiu, B. (1998) Synoviocyte-packaged *Chlamydia trachomatis* induces a chronic aseptic arthritis. *J. Clin. Invest.* 102, 1776-1782

131. Smith, G. P., Petrenko, V. A. (1997) Phage Display. *Chem. Rev* 97, 391-410

132. Giudicelli, V., Chaume, D., Lefranc, M. P. (2004) IMGT/V-QUEST, an integrated software program for immunoglobulin and T cell receptor V-J and V-D-J rearrangement analysis. *Nucl. Acids. Res.* 32, W435-W440

133. Zhang, G. L., Srinivasan, K. N., Veeramani, A., August, J., Brusic, V. (2005) PREDBALB/c: a system for the prediction of peptide binding to H2$^d$ molecules, a haplotype of the BALB/c mouse. *Nucl. Acids. Res.* 33, W180-W183

134. Bala, I., Hariharan, S., Kumar, M. N. V. R. (2004) PLGA nanoparticles in drug delivery: The state of the art. *Cri. Rev. Therapeutic Drug Carrier Sys.* 21, 387-422

135. Garti, N. (1997) Double emulsions—scope, limitations and new achievements. *Colloids and Surfaces*, A 123-124, 233-246

136. Desai, M. P., Labhasetwar, V., Amidon, G. L., Levy, R. J. (1996) Gastrointestinal uptake of biodegradable microparticles: effect of particle size. *Pharm. Res.* 13, 1838-1845

137. Manolova, V., Flace, A., Bauer, M., Schwarz, K., Saudan, P., Bachmann, M. F. (2008) Nanoparticles target distinct dendritic cell populations according to their size. *Eur. J. Iimmunol* 38, 1404-1413

138. Freytag, L. C., Clements, J. D. (2005) Mucosal adjuvants. *Vaccine* 23, 1804-1813

139. Li, H., Tran, V. V., Hu, Y., Saltzman, W. M., Barnstable, C. J., Tombran-Tink, J. (2006) A PEDF N-terminal peptide protects the retina from ischemic injury when delivered in PLGA nanospheres. *Exp. Eye Res.* 83, 824-833

140. Liu, J., Zhang, S. M., Chen, P. P., Cheng, L., Zhou, W., Tang, W. X., Chen, Z. W., Ke, C. M. (2007) Controlled release of insulin from PLGA nanoparticles embedded within PVA hydrogels. *Journal of Materials Science: Materials in Medicine* 18, 2205-2210

141. Fahmy T M, Demento S L, Caplan M J, Mellman I, Saltzman W M (2008) Design opportunities for actively targeted nanoparticle vaccines. Nanomed. 3:343-55

142. Yang Y F and Thanavala Y (1995) A comparison of the antibody and T cell response elicited by internal image and noninternal image anti-idiotypes, Clin Immunol Immunopathol. 75:154-8;

143. Rajadhyaksha M, Yang Y F and Thanavala Y (1995) Immunological evaluation of three generations of anti-idiotype vaccine: study of B and T cell responses following priming with anti-idiotype, anti-idiotype peptide and its MAP structure, Vaccine. 13:1421-6

144. Westerink M A, Smithson S L, Hutchins W A, Widera G (2001) Development and characterization of anti-idiotype based peptide and DNA vaccines which mimic the capsular polysaccharide of *Neisseria meningitidis* serogroup C, Int Rev Immunol 20:251-61.

145. Taylor H R and Prendergast RA (1987) Attempted oral immunization with chlamydial lipopolysaccharide subunit vaccine. Invest. Ophthalmol. Vis. Sci. 28:1722-26.

146. Brunham R C and M Rekart, Centers for Disease Control and Prevention Workshop, April, 2008

147. Hua S., Morrison R., Messer R., Whitmire W., Hughes S., and H. D. Caldwell (1999). The effect of doxycycline treatment on the development of protective immunity in a murine model of chlamydial genital infection. J Infect Dis 180:1252-8

148. Ripa, K. T., and P.-A. Mairdh (1977) New, simplified culture technique for *Chlamydia trachomatis*, In: D Hobson and K K Holmes (eds), Nongonococcal urethritis and related infections. American Society for Microbiology, Washington, D.C., p 323-327

The references cited and listed above are all incorporated by reference in their entirety herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. An isolated immunogenic peptide of at least about 10 amino acids and not longer than about 30 amino acids, which peptide mimics immunologically the structure of *chlamydia* genus-specific glycolipid exoantigen (GLXA) and binds to an anti-GLXA antibody, and/or when the peptide is administered to a mammalian subject in an adequate amount and in immunogenic form, it induces a protective antibody response that is measurable in:

an immunoassay that measures binding to *chlamydia* organisms of multiple chlamydial species; and/or an immunoassay or biological assay that measures inhibition of function growth or survival of said *Chlamydia* organisms, wherein the peptide comprises:

(a) Pep1, SEQ ID NO:1;

(b) Pep2, SEQ ID NO:2;

(c) Pep4, SEQ ID NO:4;

(d) Pep5, SEQ ID NO:5;

(e) Pep6, SEQ ID NO:6;
(f) Pep7, SEQ ID NO:7;
(g) Pep8, SEQ ID NO:8;
(h) Pep9, SEQ ID NO:9;
(i) Pep10, SEQ ID NO:10;
(j) Pep14, SEQ ID NO:14.

2. The immunogenic peptide of claim 1 wherein the anti-GLXA antibody to which the peptide binds is a monoclonal antibody (mAb) produced by a hybridoma cell line deposited in the ATCC as accession number HB-11300.

3. An immunogenic peptide that consists of
(a) one of the peptides (a)-(j) of claim 1;
(b) Pep 12, SEQ ID 12; or
(c) Pep 13, SEQ ID 13.

4. An immunogenic cyclic peptide comprising
(i) the immunogenic peptide (a)-(1) of claim 1.

5. The immunogenic cyclic peptide of claim 4, the linear sequence of which is selected from the group consisting of
SEQ ID NO:15; SEQ ID NO:16; SEQ ID NO:18; SEQ ID NO:19; SEQ ID NO:20; SEQ ID NO:21;
SEQ ID NO:22; SEQ ID NO:23; SEQ ID NO:24; SEQ ID NO:25; SEQ ID NO:29; SEQ ID NO:30;
SEQ ID NO:31; SEQ ID NO:32, SEQ ID NO:34; SEQ ID NO:35; SEQ ID NO:36; SEQ ID NO:37; SEQ ID NO:45; SEQ ID NO:46; SEQ ID NO:48; SEQ ID NO:49; SEQ ID NO:50; SEQ ID NO:51;
SEQ ID NO:38; SEQ ID NO:39; SEQ ID NO:40; SEQ ID NO:44; SEQ ID NO:52; SEQ ID NO:53; SEQ ID NO:54; and SEQ ID NO:58.

6. An immunogenic linear peptide oligomer or multimer that comprises between about two and about 20 repeats of the same or different peptides of claim 1, or Pep3 (SEQ ID NO:3), Pep11 (SEQ ID NO:11), Pep12 (SEQ ID NO:12) or Pep13 (SEQ ID NO:13),
wherein, when the oligomer or multimer comprises Pep3 (SEQ ID NO:3), Pep11 (SEQ ID NO:11), Pep12 (SEQ ID NO:12) or Pep13 (SEQ ID NO:13), the oligomer or multimer also includes at least one of peptides (a)-(j) from claim 1.

7. The peptide oligomer or multimer of claim 6 that comprises one or more linkers, each between any two adjacent repeating units of said peptide.

8. The peptide oligomer or multimer of claim 6 that is cyclized.

9. An immunogenic tandem oligomeric peptide that comprises two or three repeats of the peptide of claim 1 linked in tandem.

10. Pep11 (SEQ ID NO:11) or Pep12 (SEQ ID NO:12) or Pep13 (SEQ ID NO:13) is covalently linked to said functional groups.

11. An immunogenic composition comprising:
(a) the immunogenic peptide of claim 1 or Pep3 (SEQ ID NO:3), Pep11 (SEQ ID NO:11), Pep12 (SEQ ID NO:12) or Pep13 (SEQ ID NO:13); and
(b) an immunologically and pharmaceutically acceptable carrier or excipient, wherein, when (a) is Pep11 (SEQ ID NO:11), Pep3 (SEQ ID NO:3), Pep12 (SEQ ID NO:12) or Pep13 (SEQ ID NO:13),
(i) the peptide is linked or conjugated to an immunogenic carrier molecule, or
(ii) the composition further comprises an adjuvant, an immunostimulatory protein different from said peptide or a CpG oligonucleotide.

12. The immunogenic composition of claim 11 that further comprises microspheres, microparticles or nanoparticles comprising a solid matrix formed of a pharmaceutically acceptable polymer which microspheres, microparticles or nanoparticles comprise said peptide.

13. The immunogenic composition of claim 11 wherein the peptide is in the form of a linear oligomer or multimer.

14. The immunogenic composition of claim 11, wherein the peptide is linked to a filamentous bacteriophage.

15. The immunogenic composition of claim 11 that further comprises an adjuvant, an immunostimulatory protein different from said immunogenic peptide, or a CpG oligonucleotide.

16. A method of immunizing a mammalian subject against *Chlamydia* infection which comprises administering to said subject an effective immunogenic amount of the peptide of claim 1 or peptide Pep3 (SEQ ID NO:3), Pep11 (SEQ ID NO:11), Pep12 (SEQ ID NO:12) or Pep13 (SEQ ID NO:13) resulting in a chlamydial antigen GLXA-specific antibody response that is *Chlamydia* genus-specific.

17. A method of immunizing a mammalian subject against *Chlamydia* infection which comprises administering to said subject an effective immunogenic amount of the peptide of claim 6, resulting in a chlamydial antigen GLXA-specific antibody response that is *Chlamydia* genus-specific.

18. A method of immunizing a mammalian subject against *Chlamydia* infection which comprises administering to said subject an effective immunogenic amount of the composition of claim 11, resulting in a chlamydial antigen GLXA-specific antibody response that is *Chlamydia* genus-specific.

19. The method of claim 16 wherein the antibody response is a neutralizing antibody response that prevents or inhibits infectivity, growth, spread of, or pathogenesis by, said *Chlamydia* in said subject.

20. The method of claim 19 wherein the subject is a human.

21. An immunogenic composition comprising
(a) the immunogenic peptide of claim 5 or peptide Pep3 (SEQ ID NO:3) or Pep11 (SEQ ID NO:11); and
(b) an immunologically and pharmaceutically acceptable carrier or excipient, wherein, when (a) is Pep11 (SEQ ID NO:11) or Pep3 (SEQ ID NO:3),
(i) the peptide is linked or conjugated to an immunogenic carrier molecule, or
(ii) the composition further comprises an adjuvant, an immunostimulatory protein different from said peptide or a CpG oligonucleotide.

22. The immunogenic composition of claim 21 that further comprises microspheres, microparticles or nanoparticles comprising a solid matrix formed of a pharmaceutically acceptable polymer which microspheres, microparticles or nanoparticles comprise said peptide.

23. A method of immunizing a mammalian subject against *Chlamydia* infection which comprises administering to said subject an effective immunogenic amount of the peptide of claim 3 resulting in a chlamydial antigen GLXA-specific antibody response that is *Chlamydia* genus-specific.

24. A method of immunizing a mammalian subject against *Chlamydia* infection which comprises administering to said subject an effective immunogenic amount of the composition of claim 21, resulting in a chlamydial antigen GLXA-specific antibody response that is *Chlamydia* genus-specific.

25. The method of claim 24 wherein the antibody response is a neutralizing antibody response that prevents or inhibits infectivity, growth, spread of, or pathogenesis by, said *Chlamydia* in said subject.

26. The method of claim 25 wherein the subject is a human.

* * * * *

SEQUENCE LISTING

<160> NUMBER OF SEQ ID NOS: 63

<210> SEQ ID NO 1
<211> LENGTH: 12
<212> TYPE: PRT
<213> ORGANISM: Artificial Sequence
<220> FEATURE:
<223> OTHER INFORMATION: Synthetic

<400> SEQUENCE: 1

Ser Phe Phe Thr Pro Gly Leu Thr Arg Ala Pro Ser
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic

<400> SEQUENCE: 2

Leu Thr Ser His Asn Pro Thr Thr Arg Ser Tyr Glu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

Leu Val Ser Lys Pro Tyr Ser Leu Thr Lys Gly Ile
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic

<400> SEQUENCE: 4

Ala Phe Pro Gln Phe Arg Ser Ala Thr Leu Leu Leu
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5

Ser Ser Pro Ser Thr Asn Gln Tyr Ser Gly Leu Ser
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic

<400> SEQUENCE: 6

Ser Met Thr Glu Ser Arg Phe His Pro Leu Ser Leu

<210> SEQ ID NO 7
<211> LENGTH: 12
<212> TYPE: PRT
<213> ORGANISM: Artificial Sequence
<220> FEATURE:
<223> OTHER INFORMATION: Synthetic

<400> SEQUENCE: 7

His Ala Leu Met Pro Ala Thr Ala Val Ala Ser Leu
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic

<400> SEQUENCE: 8

Gly Tyr Thr Phe Thr Asp Tyr Ser Met His
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic

<400> SEQUENCE: 9

Cys Ile Ser Thr Glu Thr Gly Glu Ser Thr Tyr
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic

<400> SEQUENCE: 10

Arg Tyr Asp Val Gly Gly Asp His Tyr Tyr Phe Thr Met Asp
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic

<400> SEQUENCE: 11

His Thr Gln Asn Met Arg Met Tyr Glu Pro Trp Phe
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12

Ser Glu Ser Val Asp Ser Tyr Gly Asn Ser Phe Met
1               5                   10

```
<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Tyr Arg Ala Ser Asn Leu Glu Ser Gly
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

Cys Gln Gln Asn Asn Glu Asp Pro Trp Thr Phe
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic

<400> SEQUENCE: 15

Cys Ser Phe Phe Thr Pro Gly Leu Thr Arg Ala Pro Ser Cys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic

<400> SEQUENCE: 16

Cys Leu Thr Ser His Asn Pro Thr Thr Arg Ser Tyr Glu Cys
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic

<400> SEQUENCE: 17

Cys Leu Val Ser Lys Pro Tyr Ser Leu Thr Lys Gly Ile Cys
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic

<400> SEQUENCE: 18

Cys Ala Phe Pro Gln Phe Arg Ser Ala Thr Leu Leu Leu Cys
1               5                   10

<210> SEQ ID NO 19
```

```
<211> LENGTH: 14
<212> TYPE: PRT
<213> ORGANISM: Artificial Sequence
<220> FEATURE:
<223> OTHER INFORMATION: Synthetic

<400> SEQUENCE: 19

Cys Ser Ser Pro Ser Thr Asn Gln Tyr Ser Gly Leu Ser Cys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetic

<400> SEQUENCE: 20

Cys Ser Met Thr Glu Ser Arg Phe His Pro Leu Ser Leu Cys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic

<400> SEQUENCE: 21

Cys His Ala Leu Met Pro Ala Thr Ala Val Ala Ser Leu Cys
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic

<400> SEQUENCE: 22

Cys Gly Tyr Thr Phe Thr Asp Tyr Ser Met His Cys
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic

<400> SEQUENCE: 23

Cys Cys Ile Ser Thr Glu Thr Gly Glu Ser Thr Tyr Cys
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic

<400> SEQUENCE: 24

Cys Ile Ser Thr Glu Thr Gly Glu Ser Thr Tyr Cys
1               5                   10

<210> SEQ ID NO 25
<211> LENGTH: 17
<212> TYPE: PRT
```

```
<213> ORGANISM: Artificial Sequence
<220> FEATURE:
<223> OTHER INFORMATION: Synthetic

<400> SEQUENCE: 25

Cys Arg Tyr Asp Val Gly Gly Asp His Tyr Tyr Phe Thr Met Asp Tyr
1               5                   10                  15

Cys

<210> SEQ ID NO 26
<211> LENGTH: 14
<212> TYPE: PRT
<213> ORGANISM: Artificial Sequence
<220> FEATURE:
<223> OTHER INFORMATION: Synthetic

<400> SEQUENCE: 26

Cys His Thr Gln Asn Met Arg Met Tyr Glu Pro Trp Phe Cys
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic

<400> SEQUENCE: 27

Cys Ser Glu Ser Val Asp Ser Tyr Gly Asn Ser Phe Met Cys
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic

<400> SEQUENCE: 28

Cys Tyr Arg Ala Ser Asn Leu Glu Ser Gly Cys
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic

<400> SEQUENCE: 29

Cys Gln Gln Asn Asn Glu Asp Pro Trp Thr Phe Cys
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic

<400> SEQUENCE: 30

Cys Cys Gln Gln Asn Asn Glu Asp Pro Trp Thr Phe Cys
1               5                   10

<210> SEQ ID NO 31
<211> LENGTH: 14
<212> TYPE: PRT
```

```
<213> ORGANISM: Artificial Sequence
<220> FEATURE:
<223> OTHER INFORMATION: Synthetic

<400> SEQUENCE: 31

Glu Ser Phe Phe Thr Pro Gly Leu Thr Arg Ala Pro Ser Lys
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic

<400> SEQUENCE: 32

Glu Leu Thr Ser His Asn Pro Thr Thr Arg Ser Tyr Glu Lys
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic

<400> SEQUENCE: 33

Glu Leu Val Ser Lys Pro Tyr Ser Leu Thr Lys Gly Ile Lys
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic

<400> SEQUENCE: 34

Glu Ala Phe Pro Gln Phe Arg Ser Ala Thr Leu Leu Leu Lys
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic

<400> SEQUENCE: 35

Glu Ser Ser Pro Ser Thr Asn Gln Tyr Ser Gly Leu Ser Lys
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic

<400> SEQUENCE: 36

Glu Ser Met Thr Glu Ser Arg Phe His Pro Leu Ser Leu Lys
1               5                   10

<210> SEQ ID NO 37
<211> LENGTH: 14
<212> TYPE: PRT
<213> ORGANISM: Artificial Sequence
<220> FEATURE:
```

<223> OTHER INFORMATION: Synthetic

<400> SEQUENCE: 37

Glu His Ala Leu Met Pro Ala Thr Ala Val Ala Ser Leu Lys
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic

<400> SEQUENCE: 38

Glu Gly Tyr Thr Phe Thr Asp Tyr Ser Met His Lys
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthetic

<400> SEQUENCE: 39

Glu Cys Ile Ser Thr Glu Thr Gly Glu Ser Thr Tyr Lys
1               5                   10

<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40

Glu Arg Tyr Asp Val Gly Gly Asp His Tyr Tyr Phe Thr Met Asp Tyr
1               5                   10                  15

Lys

<210> SEQ ID NO 41
<211> LENGTH: 14
<212> TYPE: PRT
<213> ORGANISM: Artificial Sequence
<220> FEATURE:
<223> OTHER INFORMATION: Synthetic

<400> SEQUENCE: 41

Glu His Thr Gln Asn Met Arg Met Tyr Glu Pro Trp Phe Lys
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Synthetic

<400> SEQUENCE: 42

Glu Ser Glu Ser Val Asp Ser Tyr Gly Asn Ser Phe Met Lys
1               5                   10

<210> SEQ ID NO 43
<211> LENGTH: 11
<212> TYPE: PRT
<213> ORGANISM: Artificial Sequence
<220> FEATURE:

<223> OTHER INFORMATION: Synthetic

<400> SEQUENCE: 43

Glu Tyr Arg Ala Ser Asn Leu Glu Ser Gly Lys
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetic

<400> SEQUENCE: 44

Glu Cys Gln Gln Asn Asn Glu Asp Pro Trp Thr Phe Lys
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Synthetic

<400> SEQUENCE: 45

Lys Ser Phe Phe Thr Pro Gly Leu Thr Arg Ala Pro Ser Glu
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Synthetic

<400> SEQUENCE: 46

Lys Leu Thr Ser His Asn Pro Thr Thr Arg Ser Tyr Glu Glu
1               5                   10

<210> SEQ ID NO 47
<211> LENGTH: 15
<212> TYPE: PRT
<213> ORGANISM: Artificial Sequence
<220> FEATURE:
<223> OTHER INFORMATION: Synthetic

<400> SEQUENCE: 47

Lys Leu Val Ser Lys Pro Tyr Ser Leu Thr Lys Gly Ile Cys Glu
1               5                   10                  15

<210> SEQ ID NO 48
<211> LENGTH: 14
<212> TYPE: PRT
<213> ORGANISM: Artificial Sequence
<220> FEATURE:
<223> OTHER INFORMATION: Synthetic

<400> SEQUENCE: 48

Lys Ala Phe Pro Gln Phe Arg Ser Ala Thr Leu Leu Leu Glu
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Synthetic

```
<400> SEQUENCE: 49

Lys Ser Ser Pro Ser Thr Asn Gln Tyr Ser Gly Leu Ser Glu
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Synthetic

<400> SEQUENCE: 50

Lys Ser Met Thr Glu Ser Arg Phe His Pro Leu Ser Leu Glu
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Synthetic

<400> SEQUENCE: 51

Lys His Ala Leu Met Pro Ala Thr Ala Val Ala Ser Leu Glu
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic

<400> SEQUENCE: 52

Lys Gly Tyr Thr Phe Thr Asp Tyr Ser Met His Glu
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthetic

<400> SEQUENCE: 53

Lys Cys Ile Ser Thr Glu Thr Gly Glu Ser Thr Tyr Glu
1               5                   10

<210> SEQ ID NO 54
<211> LENGTH: 17
<212> TYPE: PRT
<213> ORGANISM: Artificial Sequence
<220> FEATURE:
<223> OTHER INFORMATION: Synthetic

<400> SEQUENCE: 54

Lys Arg Tyr Asp Val Gly Gly Asp His Tyr Tyr Phe Thr Met Asp Tyr
1               5                   10                  15

Glu

<210> SEQ ID NO 55
<211> LENGTH: 14
<212> TYPE: PRT
<213> ORGANISM: Artificial Sequence
<220> FEATURE:
<223> OTHER INFORMATION: Synthetic
```

<400> SEQUENCE: 55

Lys His Thr Gln Asn Met Arg Met Tyr Glu Pro Trp Phe Glu
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Synthetic

<400> SEQUENCE: 56

Lys Ser Glu Ser Val Asp Ser Tyr Gly Asn Ser Phe Met Glu
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Synthetic

<400> SEQUENCE: 57

Lys Cys Gln Gln Asn Asn Glu Asp Pro Trp Thr Phe Glu
1               5                   10

<210> SEQ ID NO 58
<211> LENGTH: 411
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(411)

<400> SEQUENCE: 58

```
att caa gta cag ctg gag gag tct gga cct gaa ctg agg aag cct gga        48
Ile Gln Val Gln Leu Glu Glu Ser Gly Pro Glu Leu Arg Lys Pro Gly
1               5                   10                  15 gag gca gtc aag atc tcc tgc aag act tct ggt tat acc ttc aca gac        96
Glu Ala Val Lys Ile Ser Cys Lys Thr Ser Gly Tyr Thr Phe Thr Asp
            20                  25                  30 tat tca atg cac tgg gtg aag cag gct cca gga aag ggt tta aag tgg      144
Tyr Ser Met His Trp Val Lys Gln Ala Pro Gly Lys Gly Leu Lys Trp
        35                  40                  45 atg ggc tgc ata agc act gag act ggt gag tca aca tat gca gat gac      192
Met Gly Cys Ile Ser Thr Glu Thr Gly Glu Ser Thr Tyr Ala Asp Asp
    50                  55                  60 ttc aag gga cgg ttt gcc ttc tct ttg gaa acc tct gcc agc aca gcc      240
Phe Lys Gly Arg Phe Ala Phe Ser Leu Glu Thr Ser Ala Ser Thr Ala
65                  70                  75                  80 tat ttg cag atc aac aac ctc aaa gat gag gac acg gct aca tat ttc      288
Tyr Leu Gln Ile Asn Asn Leu Lys Asp Glu Asp Thr Ala Thr Tyr Phe
                85                  90                  95 tgt gct aga agg tac gac gtc gga ggc gat cat tac tac ttt act atg      336
Cys Ala Arg Arg Tyr Asp Val Gly Gly Asp His Tyr Tyr Phe Thr Met
            100                 105                 110 gac tac tgg ggt caa gga acc tca gtc acc gtc tcc tca gcc aaa acg      384
Asp Tyr Trp Gly Gln Gly Thr Ser Val Thr Val Ser Ser Ala Lys Thr
        115                 120                 125 aca ccc cca tcg tct ata atc act agt                                   411
Thr Pro Pro Ser Ser Ile Ile Thr Ser
    130                 135
```

<210> SEQ ID NO 59
<211> LENGTH: 137
<212> TYPE: PRT
<213> ORGANISM: Artificial Sequence
<220> FEATURE:
<223> OTHER INFORMATION: Synthetic Construct

<400> SEQUENCE: 59

```
Ile Gln Val Gln Leu Glu Glu Ser Gly Pro Glu Leu Arg Lys Pro Gly
1               5                   10                  15
Glu Ala Val Lys Ile Ser Cys Lys Thr Ser Gly Tyr Thr Phe Thr Asp
            20                  25                  30
Tyr Ser Met His Trp Val Lys Gln Ala Pro Gly Lys Gly Leu Lys Trp
        35                  40                  45
Met Gly Cys Ile Ser Thr Glu Thr Gly Glu Ser Thr Tyr Ala Asp Asp
    50                  55                  60
Phe Lys Gly Arg Phe Ala Phe Ser Leu Glu Thr Ser Ala Ser Thr Ala
65                  70                  75                  80
Tyr Leu Gln Ile Asn Asn Leu Lys Asp Glu Asp Thr Ala Thr Tyr Phe
                85                  90                  95
Cys Ala Arg Arg Tyr Asp Val Gly Gly Asp His Tyr Tyr Phe Thr Met
            100                 105                 110
Asp Tyr Trp Gly Gln Gly Thr Ser Val Thr Val Ser Ser Ala Lys Thr
        115                 120                 125
Thr Pro Pro Ser Ser Ile Ile Thr Ser
    130                 135
```

<210> SEQ ID NO 60
<211> LENGTH: 387
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(387)

<400> SEQUENCE: 60

```
gat tgg gag ctc gac att gtg atc aca cag act aca gtt tct ttg gct      48
Asp Trp Glu Leu Asp Ile Val Ile Thr Gln Thr Thr Val Ser Leu Ala
1               5                   10                  15 gtg tct cta ggg cag agg gcc acc atg tcc tgc aga gcc agt gaa agt      96
Val Ser Leu Gly Gln Arg Ala Thr Met Ser Cys Arg Ala Ser Glu Ser
            20                  25                  30 gtt gat agt tat ggc aat agt ttt atg tac tgg ttc cag cag aaa cca     144
Val Asp Ser Tyr Gly Asn Ser Phe Met Tyr Trp Phe Gln Gln Lys Pro
        35                  40                  45 gga cag cca ccc aaa ctc ctc atc tat cgt gca tcc aat cta gaa tct     192
Gly Gln Pro Pro Lys Leu Leu Ile Tyr Arg Ala Ser Asn Leu Glu Ser
    50                  55                  60 ggg gtc cct gcc agg ttc agt ggc agt ggg tct agg aca gac ttc atc     240
Gly Val Pro Ala Arg Phe Ser Gly Ser Gly Ser Arg Thr Asp Phe Ile
65                  70                  75                  80 ctc acc att gat cct gtg gag gct gat gat gct gct acc tat tac tgt     288
Leu Thr Ile Asp Pro Val Glu Ala Asp Asp Ala Ala Thr Tyr Tyr Cys
                85                  90                  95 cag caa aat aat gag gat ccg tgg acg ttc ggt gga ggc acc aag ctg     336
Gln Gln Asn Asn Glu Asp Pro Trp Thr Phe Gly Gly Gly Thr Lys Leu
            100                 105                 110 gaa atc aaa cgg gct gat gct gca cca act gta tcc gca tgc acc aat     384
Glu Ile Lys Arg Ala Asp Ala Ala Pro Thr Val Ser Ala Cys Thr Asn
```

```
                     115                 120                 125
cac                                                                         387
His <210> SEQ ID NO 61
<211> LENGTH: 129
<212> TYPE: PRT
<213> ORGANISM: Artificial Sequence
<220> FEATURE:
<223> OTHER INFORMATION: Synthetic Construct

<400> SEQUENCE: 61

Asp Trp Glu Leu Asp Ile Val Ile Thr Gln Thr Val Ser Leu Ala
1               5                   10                  15

Val Ser Leu Gly Gln Arg Ala Thr Met Ser Cys Arg Ala Ser Glu Ser
            20                  25                  30

Val Asp Ser Tyr Gly Asn Ser Phe Met Tyr Trp Phe Gln Gln Lys Pro
        35                  40                  45

Gly Gln Pro Pro Lys Leu Leu Ile Tyr Arg Ala Ser Asn Leu Glu Ser
    50                  55                  60

Gly Val Pro Ala Arg Phe Ser Gly Ser Gly Ser Arg Thr Asp Phe Ile
65                  70                  75                  80

Leu Thr Ile Asp Pro Val Glu Ala Asp Ala Ala Thr Tyr Tyr Cys
                85                  90                  95

Gln Gln Asn Asn Glu Asp Pro Trp Thr Phe Gly Gly Gly Thr Lys Leu
            100                 105                 110

Glu Ile Lys Arg Ala Asp Ala Ala Pro Thr Val Ser Ala Cys Thr Asn
        115                 120                 125

His

<210> SEQ ID NO 62
<211> LENGTH: 6
<212> TYPE: PRT
<213> ORGANISM: Artificial Sequence
<220> FEATURE:
<223> OTHER INFORMATION: Synthetic

<400> SEQUENCE: 62

Val Pro Arg Gly Ser Asp
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic

<400> SEQUENCE: 63

Asp Asp Lys Asp Trp His
1               5
```